(12) United States Patent
Freisen et al.

(10) Patent No.: US 6,399,636 B2
(45) Date of Patent: Jun. 4, 2002

(54) TRI-ARYL-SUBSTITUTED-ETHANE PDE4 INHIBITORS

(75) Inventors: Richard Freisen, Kirkland; Yves Ducharme, Montreal; Bernard Cote, Ile-Perrot; Marc Blouin, St. Lazare de Vaudreuil; Evelyn Martins, Vaudreuil; Daniel Guay, Notre-Dame de I'Ile Perrot; Pierre Hamel, Vimont-Laval; Mario Girard, St. Lazare; Richard Frenette, Laval; Sebastien Laliberte, Ile Perrot, all of (CA)

(73) Assignee: Merck Frosst Canada & Co., Kirkland (CA)

( * ) Notice: Subject to any disclaimer, the term of this patent is extended or adjusted under 35 U.S.C. 154(b) by 0 days.

(21) Appl. No.: 09/810,119

(22) Filed: Mar. 16, 2001

Related U.S. Application Data

(60) Provisional application No. 60/191,668, filed on Mar. 23, 2000.

(51) Int. Cl.$^7$ .................. A61K 31/4439; C07D 401/10
(52) U.S. Cl. ................... 514/333; 514/342; 546/256; 546/269.7
(58) Field of Search ................ 514/333, 342; 546/256, 269.7

(56) References Cited

U.S. PATENT DOCUMENTS

| | | | |
|---|---|---|---|
| 5,340,827 A | 8/1994 | Beeley et al. |
| 5,491,147 A | 2/1996 | Boyd et al. |
| 5,550,137 A | 8/1996 | Beeley et al. |
| 5,580,888 A | 12/1996 | Warrellow et al. |
| 5,608,070 A | 3/1997 | Alexander et al. |
| 5,622,977 A | 4/1997 | Warrellow et al. |
| 5,633,257 A | 5/1997 | Warrellow et al. |
| 5,679,712 A | 10/1997 | Schwark et al. |
| 5,693,672 A | 12/1997 | Weichert et al. |
| 5,710,160 A | 1/1998 | Guay et al. |
| 5,710,170 A | 1/1998 | Guay et al. |
| 5,736,297 A | 4/1998 | Roeschert et al. |
| 5,739,144 A | 4/1998 | Warrellow et al. |
| 5,747,541 A | 5/1998 | Weichert et al. |
| 5,776,958 A | 7/1998 | Warrellow et al. |
| 5,780,477 A | 7/1998 | Head et al. |
| 5,780,478 A | 7/1998 | Alexander et al. |
| 5,786,354 A | 7/1998 | Warrellow et al. |
| 5,798,373 A | 8/1998 | Warrellow |
| 5,849,770 A | 12/1998 | Head et al. |
| 5,859,034 A | 1/1999 | Warrellow et al. |
| 5,866,593 A | 2/1999 | Warrellow et al. |
| 5,891,896 A | 4/1999 | Warrellow et al. |

FOREIGN PATENT DOCUMENTS

| | | |
|---|---|---|
| EP | 811610 | 12/1997 |
| WO | WO 94/22852 | 10/1994 |
| WO | WO 95/35283 | 12/1995 |
| WO | WO 96/00215 | 1/1996 |
| WO | WO 98/25883 | 6/1998 |
| WO | WO 99/50262 | 10/1999 |

OTHER PUBLICATIONS

C. Burnouf, et al., Ann. Rep. In Med. Chem., 33: 91–109 (1998).
S. B. Christensen, et al., J. Med. Chem., 41: 821–835 (1998).
A. H. Cook, et al., J. Chem. Soc., 413–417 (1943).
M. D. Houslay, et al., Adv. In Pharmacol., 44: 225–342 (1998).
B. Hughes, et al., Br. J. Pharmacol., 118: 1183–1191 (1996).
K. Manabe, et a., J. Am Chem., 114(17): 6940–6941 (1992).
K. Manabe, et al., J. Org. Chem. 58(24): 6692–6700 (1993).
K. Manabe, et al., J. Am. Chem. Soc., 115 (12): 5324–5325 (1993).
M. J. Perry, et al., Cell Biochem. Biophys., 29: 113–132 (1998).
D. Spina, et al., Adv. In. Pharmacol., 44: 33–89 (1998).

*Primary Examiner*—Patricia L. Morris
(74) *Attorney, Agent, or Firm*—Shu Muk Lee; David L. Rose

(57) ABSTRACT

Novel ethanes substituted with i) a phenyl, ii) a thiazole, and iii) a pyridyl moiety are PDE4 inhibitors.

17 Claims, No Drawings

TRI-ARYL-SUBSTITUTED-ETHANE PDE4 INHIBITORS

This application claims benefit of priority of U.S. provisional application Serial No. 60/191,668, filed Mar. 23, 2000.

BACKGROUND OF THE INVENTION

1. Field of the Invention

The present invention is directed to compounds that are tri-aryl substituted ethanes. In particular, this invention is directed to ethanes substituted with i) a phenyl, ii) a thiazole, and iii) a pyridyl moiety which are phosphodiesterase-4 inhibitors.

2. Related Background

Hormones are compounds that variously affect cellular activity. In many respects, hormones act as messengers to trigger specific cellular responses and activities. Many effects produced by hormones, however, are not caused by the singular effect of just the hormone. Instead, the hormone first binds to a receptor, thereby triggering the release of a second compound that goes on to affect the cellular activity. In this scenario, the hormone is known as the first messenger while the second compound is called the second messenger. Cyclic adenosine monophosphate (adenosine 3', 5'-cyclic monophosphate, "cAMP" or "cyclic AMP") is known as a second messenger for hormones including epinephrine, glucagon, calcitonin, corticotrophin, lipotropin, luteinizing hormone, norepinephrine, parathyroid hormone, thyroid-stimulating hormone, and vasopressin. Thus, cAMP mediates cellular responses to hormones. Cyclic AMP also mediates cellular responses to various neurotransmitters.

Phosphodiesterases ("PDE") are a family of enzymes that metabolize 3', 5' cyclic nucleotides to 5' nucleoside monophosphates, thereby terminating cAMP second messenger activity. A particular phosphodiesterase, phosphodiesterase-4 ("PDE4", also known as "PDE-IV"), which is a high affinity, cAMP specific, type IV PDE, has generated interest as potential targets for the development of novel anti-asthmatic and anti-inflammatory compounds. PDE4 is known to exist as at lease four isoenzymes, each of which is encoded by a distinct gene. Each of the four known PDE4 gene products is believed to play varying roles in allergic and/or inflammatory responses. Thus, it is believed that inhibition of PDE4, particularly the specific PDE4 isoforms that produce detrimental responses, can beneficially affect allergy and inflammation symptoms. It would be desirable to provide novel compounds and compositions that inhibit PDE4 activity.

Inhibition of PDE4 activity is believed effective for the treatment of osteoporosis by reducing bone loss. For example, Ken-ici Miyamoto et al., Biochem. Pharmacology, 54:613–617(1997) describes the effect of a PDE4 on bone loss. Therefore, it would be desirable to provide novel compounds and compositions that inhibit PDE4 activity.

A major concern with the use of PDE4 inhibitors is the side effect of emesis which has been observed for several candidate compounds as described in C. Burnouf et al., ("Burnouf"), *Ann. Rep. In Med. Chem.,* 33:91–109(1998). B. Hughes et al., *Br. J.Pharmacol.,* 118:1183–1191(1996); M. J. Perry et al., *Cell Biochem. Biophys.,* 29:113–132(1998); S. B. Christensen et al., *J.Med. Chem.,* 41:821–835(1998); and Burnouf describe the wide variation of the severity of the undesirable side effects exhibited by various compounds. As described in M. D. Houslay et al., *Adv. In Pharmacol.,* 44:225–342(1998) and D. Spina et al., *Adv. In Pharmacol.,* 44:33–89(1998), there is great interest and research of therapeutic PDE4 inhibitors.

U.S. Pat. Nos. 5,622,977, 5,710,160, 5,710,170, 5,798,373, 5,849,770, and International Patent Publication No. WO 99/50262 describe tri-substituted aryl derivative PDE IV inhibitors, including tri-aryl ethane derivatives.

Compounds that include ringed systems are described by various investigators as effective for a variety of therapies and utilities. For example, International Patent Publication No. WO 98/25883 describes ketobenzamides as calpain inhibitors, European Patent Publication No. EP 811610 and U.S. Pat. Nos. 5,679,712, 5,693,672 and 5,747,541 describe substituted benzoylguanidine sodium channel blockers, U.S. Pat. No. 5,736,297 describes ring systems useful as a photosensitive composition. International Patent Publication WO9422852 describes quinolines as PDE4 inhibitors.

U.S. Pat. Nos. 5,491,147, 5,608,070, 5,739,144, 5,776,958, 5,780,477, 5,786,354, 5,859,034, 5,866,593, 5,891,896, and International Patent Publication WO 95/35283 describe PDE4 inhibitors that are tri-substituted aryl or heteroaryl phenyl derivatives. U.S. Pat. No. 5,580,888 describes PDE4 inhibitors that are styryl derivatives. U.S. Pat. No. 5,550,137 describes PDE4 inhibitors that are phenylaminocarbonyl derivatives. U.S. Pat. No. 5,340,827 describes PDE4 inhibitors that are phenylcarboxamide compounds. U.S. Pat. No. 5,780,478 describes PDE4 inhibitors that are tetra-substituted phenyl derivatives. International Patent Publication WO 96/00215 describes substituted oxime derivatives useful as PDE4 inhibitors. U.S. Pat. No. 5,633,257 describes PDE4 inhibitors that are cyclo(alkyl and alkenyl)phenyl-alkenyl (aryl and heteroaryl) compounds.

However, there remains a need for novel compounds and compositions that therapeutically inhibit PDE4 with minimal side effects.

SUMMARY OF THE INVENTION

The present invention is directed to novel tri-aryl substituted ethanes. In particular, this invention is directed to ethanes substituted with i) a phenyl, ii) a thiazole, and iii) a pyridyl moiety which are phosphodiesterase-4 inhibitors. This invention also provides a pharmaceutical composition which includes an effective amount of the novel tri-aryl substituted ethanes and a pharmaceutically acceptable carrier. This invention further provides a method of treatment in mammals of, for example, asthma, chronic bronchitis, chronic obstructive pulmonary disease (COPD), eosinophilic granuloma, psoriasis and other benign or malignant proliferative skin diseases, endotoxic shock (and associated conditions such as laminitis and colic in horses), septic shock, ulcerative colitis, Crohn's disease, reperfusion injury of the myocardium and brain, inflammatory arthritis, chronic glomerulonephritis, atopic dermatitis, urticaria, adult respiratory distress syndrome, infant respiratory distress syndrome, chronic obstructive pulmonary disease in animals, diabetes insipidus, allergic rhinitis, allergic conjunctivitis, vernal conjunctivitis, arterial restenosis, ortheroscleorsis, atherosclerosis, neurogenic inflammation, pain, cough, rheumatoid arthritis, ankylosing spondylitis, transplant rejection and graft versus host disease, hypersecretion of gastric acid, bacterial, fungal or viral induced sepsis or septic shock, inflammation and cytokine-mediated chronic tissue degeneration, osteoarthritis, cancer, cachexia, muscle wasting, depression, memory impairment, tumour growth, cancerous invasion of normal tissues, osteoporosis, and bone loss by the administration of an effective amount of the novel ethanes substituted with i) a phenyl, ii) a thiazole, and iii) a pyridyl moiety which are phosphodiesterase-4 inhibitors.

DETAILED DESCRIPTION OF THE INVENTION

A compound of this invention is represented by Formula (I):

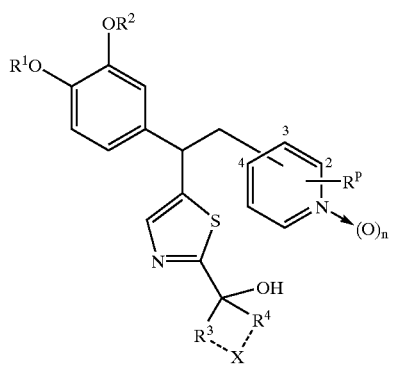

or a pharmaceutically acceptable salt thereof, wherein
$R^1$ is $C_{1-6}$alkyl or $C_{3-6}$cycloalkyl, optionally substituted with 1–4 independent halogen;
$R^2$ is $C_{1-6}$alkyl or $C_{3-6}$cycloalkyl, optionally substituted with 1–4 independent halogen;
$R^3$ is $C_{1-4}$alkyl, $C_{3-6}$cycloalkyl, heteroaryl, or phenyl, any of which optionally substituted independently with 1–4 independent halogen or $C_{1-6}$alkyl;
$R^4$ is H or $C_{1-4}$alkyl, said alkyl optionally substituted with 1–4 independent halogen;
$R^P$ is H, halogen, nitrile, or a $C_{1-6}$alkyl group, said alkyl optionally substituted with 1–4 independent halogen;
n is 0 or 1; and
when $R^3$ and $R^4$ are connected to each other through X, then $R^3$ and $R^4$ are each $C_1$alkyl, and X is $C_{0-4}$alkyl.

According to one aspect, a compound of this invention is represented by formula (I) or a pharmaceutically acceptable salt thereof, wherein
$R^1$ is $C_{1-6}$alkyl, optionally substituted with 1–4 independent halogen;
$R^2$ is $C_{1-6}$alkyl or $C_{3-6}$cycloalkyl, optionally substituted with 1–4 independent halogen;
$R^3$ is $C_{1-4}$alkyl, $C_{3-6}$cycloalkyl, heteroaryl, or phenyl, any of which optionally substituted independently with 1–4 independent halogen or $C_{1-6}$alkyl;
$R^4$ is H or $C_{1-4}$alkyl, said alkyl optionally substituted with 1–4 independent halogen;
$R^P$ is H, halogen, nitrile, or a $C_{1-6}$alkyl group, said alkyl optionally substituted with 1–4 independent halogen;
n is 0 or 1; and
when $R^3$ and $R^4$ are connected to each other through X, then $R^3$ and $R^4$ are each $C_1$alkyl, and X is $C_{0-4}$alkyl.

According to one embodiment of this aspect,
$R^1$ is $C_{1-6}$alkyl, optionally substituted with 1–4 independent halogen;
$R^2$ is $C_{1-6}$alkyl, optionally substituted with 1–4 independent halogen;
$R^3$ is $C_{1-4}$alkyl, $C_{3-6}$cycloalkyl, heteroaryl, or phenyl, any of which optionally substituted independently with 1–4 independent halogen or $C_{1-6}$alkyl;
$R^4$ is H or $C_{1-4}$alkyl, said alkyl optionally substituted with 1–4 independent halogen;
$R^P$ is H, halogen, nitrile, or a $C_{1-6}$alkyl group, said alkyl optionally substituted with 1–4 independent halogen;
n is 0 or 1; and
when $R^3$ and $R^4$ are connected to each other through X, then $R^3$ and $R^4$ are each $C_1$alkyl, and X is $C_{0-4}$alkyl.

According to another embodiment of this aspect,
$R^1$ is $C_{1-6}$alkyl, optionally substituted with 1–4 independent halogen;
$R^2$ is $C_{1-6}$alkyl, optionally substituted with 1–4 independent halogen;
$R^3$ is $C_{1-4}$alkyl, optionally substituted independently with 1–4 independent halogen or $C_{1-6}$alkyl;
$R^4$ is H or $C_{1-4}$alkyl, said alkyl optionally substituted with 1–4 independent halogen;
$R^P$ is H, halogen, nitrile, or a $C_{1-6}$alkyl group, said alkyl optionally substituted with 1–4 independent halogen; and
n is 0 or 1.

According to yet another embodiment of this aspect,
$R^1$ is $C_{1-6}$alkyl, optionally substituted with 1–4 independent halogen;
$R^2$ is $C_{1-6}$alkyl, optionally substituted with 1–4 independent halogen;
$R^3$ is $C_{3-6}$cycloalkyl, optionally substituted independently with 1–4 independent halogen or $C_{1-6}$alkyl;
$R^4$ is H or $C_{1-4}$alkyl, said alkyl optionally substituted with 1–4 independent halogen;
$R^P$ is H, halogen, nitrile, or a $C_{1-6}$alkyl group, said alkyl optionally substituted with 1–4 independent halogen; and
n is 0 or 1.

According to an embodiment of this aspect,
$R^1$ is $C_{1-6}$alkyl, optionally substituted with 1–4 independent halogen;
$R^2$ is $C_{1-6}$alkyl, optionally substituted with 1–4 independent halogen;
$R^3$ is heteroaryl, optionally substituted independently with 1–4 independent halogen or $C_{1-6}$alkyl;
$R^4$ is H or $C_{1-4}$alkyl, said alkyl optionally substituted with 1–4 independent halogen;
$R^P$ is H, halogen, nitrile, or a $C_{1-6}$alkyl group, said alkyl optionally substituted with 1–4 independent halogen; and
n is 0 or 1.

According to an embodiment of this aspect,
$R^1$ is $C_{1-6}$alkyl, optionally substituted with 1–4 independent halogen;
$R^2$ is $C_{1-6}$alkyl, optionally substituted with 1–4 independent halogen;
$R^3$ is phenyl, optionally substituted independently with 1–4 independent halogen or $C_{1-6}$alkyl;
$R^4$ is H or $C_{1-4}$alkyl, said alkyl optionally substituted with 1–4 independent halogen;
$R^P$ is H, halogen, nitrile, or a $C_{1-6}$alkyl group, said alkyl optionally substituted with 1–4 independent halogen; and
n is 0 or 1.

According to still another embodiment of this aspect,
$R^1$ is $C_{1-6}$alkyl, optionally substituted with 1–4 independent halogen;

$R^2$ is $C_{1-6}$alkyl, optionally substituted with 1–4 independent halogen;

$R^3$ and $R^4$ are connected to each other through X;

$R^3$ and $R^4$ are each $C_1$alkyl;

X is $C_{0-4}$alkyl;

$R^P$ is H, halogen, nitrile, or a $C_{1-6}$alkyl group, said alkyl optionally substituted with 1–4 independent halogen; and n is 0 or 1.

According to another embodiment of this aspect, $R^1$ is $C_{1-6}$alkyl, optionally substituted with 1–4 independent halogen;

$R^2$ is $C_{3-6}$cycloalkyl, optionally substituted with 14 independent halogen;

$R^3$ is $C_{1-4}$alkyl, $C_{3-6}$cycloalkyl, heteroaryl, or phenyl, any of which optionally substituted independently with 1–4 independent halogen or $C_{1-6}$alkyl;

$R^4$ is H or $C_{1-4}$alkyl, said alkyl optionally substituted with 1–4 independent halogen;

$R^P$ is H, halogen, nitrile, or a $C_{1-6}$alkyl group, said alkyl optionally substituted with 1–4 independent halogen;

n is 0 or 1; and when $R^3$ and $R^4$ are connected to each other through X, then $R^3$ and $R^4$ are each $C_1$alkyl, and X is $C_{0-4}$alkyl.

According to another embodiment of this aspect, $R^1$ is $C_{1-6}$alkyl, optionally substituted with 1–4 independent halogen;

$R^2$ is $C_{3-6}$cycloalkyl, optionally substituted with 1–4 independent halogen;

$R^3$ is $C_{1-4}$alkyl, optionally substituted independently with 1–4 independent halogen or $C_{1-6}$alkyl;

$R^4$ is H or $C_{1-4}$alkyl, said alkyl optionally substituted with 1–4 independent halogen;

$R^P$ is H, halogen, nitrile, or a $C_{1-6}$alkyl group, said alkyl optionally substituted with 1–4 independent halogen; and n is 0 or 1.

According to yet another embodiment of this aspect, $R^1$ is $C_{1-6}$alkyl, optionally substituted with 1–4 independent halogen;

$R^2$ is $C_{3-6}$cycloalkyl, optionally substituted with 1–4 independent halogen;

$R^3$ is $C_{3-6}$cycloalkyl, optionally substituted independently with 1–4 independent halogen or $C_{1-6}$alkyl;

$R^4$ is H or $C_{1-4}$alkyl, said alkyl optionally substituted with 1–4 independent halogen;

$R^P$ is H, halogen, nitrile, or a $C_{1-6}$alkyl group, said alkyl optionally substituted with 1–4 independent halogen; and n is 0 or 1.

According to an embodiment of this aspect, $R^1$ is $C_{1-6}$alkyl, optionally substituted with 1–4 independent halogen;

$R^2$ is $C_{3-6}$cycloalkyl, optionally substituted with 1–4 independent halogen;

$R^3$ is heteroaryl, optionally substituted independently with 1–4 independent halogen or $C_{1-6}$alkyl;

$R^4$ is H or $C_{1-4}$alkyl, said alkyl optionally substituted with 1–4 independent halogen;

$R^P$ is H, halogen, nitrile, or a $C_{1-6}$alkyl group, said alkyl optionally substituted with 1–4 independent halogen; and n is 0 or 1.

According to an embodiment of this aspect, $R^1$ is $C_{1-6}$alkyl, optionally substituted with 1–4 independent halogen;

$R^2$ is $C_{3-6}$cycloalkyl, optionally substituted with 1–4 independent halogen;

$R^3$ is phenyl, optionally substituted independently with 1–4 independent halogen or $C_{1-6}$alkyl;

$R^4$ is H or $C_{1-4}$alkyl, said alkyl optionally substituted with 1–4 independent halogen;

$R^P$ is H, halogen, nitrile, or a $C_{1-6}$alkyl group, said alkyl optionally substituted with 1–4 independent halogen; and n is 0 or 1.

According to still another embodiment of this aspect, $R^1$ is $C_{1-6}$alkyl, optionally substituted with 1–4 independent halogen;

$R^2$ is $C_{3-6}$cycloalkyl, optionally substituted with 1–4 independent halogen;

$R^3$ and $R^4$ are connected to each other through X;

$R^3$ and $R^4$ are each $C_1$alkyl;

X is $C_{0-4}$alkyl;

$R^P$ is H, halogen, nitrile, or a $C_{1-6}$alkyl group, said alkyl optionally substituted with 1–4 independent halogen; and n is 0 or 1.

As used herein, "alkyl" as well as other groups having the prefix "alk" such as, for example, alkoxy, alkanoyl, alkenyl, alkynyl and the like, means carbon chains which may be linear or branched or combinations thereof. Examples of alkyl groups include methyl, ethyl, propyl, isopropyl, butyl, sec- and tert-butyl, pentyl, hexyl, heptyl and the like. "Alkenyl", "alkynyl" and other like terms include carbon chains containing at least one unsaturated C—C bond.

The term "cycloalkyl" means carbocycles containing no heteroatoms, and includes mono-, bi- and tricyclic saturated carbocycles, as well as fused ring systems. Such fused ring systems can include one ring that is partially or fully unsaturated such as a benzene ring to form fused ring systems such as benzofused carbocycles. Cycloalkyl includes such fused ring systems as spirofused ring systems. Examples of cycloalkyl include cyclopropyl, cyclobutyl, cyclopentyl, cyclohexyl, decahydronaphthalene, adamantane, indanyl, indenyl, fluorenyl, 1,2,3,4-tetrahydronaphalene and the like. Similarly, "cycloalkenyl" means carbocycles containing no heteroatoms and at least one non-aromatic C—C double bond, and include mono-, bi- and tricyclic partially saturated carbocycles, as well as benzofused cycloalkenes. Examples of cycloalkenyl include cyclohexenyl, indenyl, and the like.

The term "aryl" means an aromatic substituent that is a single ring or multiple rings fused together. When formed of multiple rings, at least one of the constituent rings is aromatic. The preferred aryl substituents are phenyl and napthyl groups.

The term "cycloalkyloxy" unless specifically stated otherwise includes a cycloalkyl group connected by a short $C_1$–$C_2$alkyl length to the oxy connecting atom.

The term "$C_0$–$C_6$alkyl" includes alkyls containing 6, 5, 4, 3, 2, 1, or no carbon atoms. An alkyl with no carbon atoms is a hydrogen atom substituent.

The term "hetero" unless specifically stated otherwise includes one or more N, O, or S atoms. Heterocycloalkyl and heteroaryl are ring systems that contain one or more O, S, or N atoms in the ring, including mixtures of such atoms. The hetero atoms replace ring carbon atoms. Thus, for example, a heterocycloC$_5$alkyl is a five member ring containing from 5 to no carbon atoms. The term "heteroaryl" means an aryl group that has at least one heteroatom in the ring. The preferred heteroaryl groups are 5 and 6 member rings having 1–4 heteroatoms independently selected from N, O, or S.

The term "amine" unless specifically stated otherwise includes primary, secondary and tertiary amines.

The term "halogen" includes fluorine, chlorine, bromine and iodine atoms.

The term "optionally substituted" is intended to include both substituted and unsubstituted. Thus, for example, optionally substituted aryl could represent a pentafluorophenyl or a phenyl ring. Further, optionally substituted multiple moieties such as, for example, alkylaryl are intended to mean that the aryl and the aryl groups are optionally substituted. If only one of the multiple moieties is optionally substituted then it will be specifically recited such as "an alkylaryl, the aryl optionally substituted with halogen or hydroxyl."

Compounds described herein contain one or more double bonds and may thus give rise to cis/trans isomers as well as other conformational isomers. The present invention includes all such possible isomers as well as mixtures of such isomers.

Compounds described herein can contain one or more asymmetric centers and may thus give rise to diastereomers and optical isomers. The present invention includes all such possible diastereomers as well as their racemic mixtures, their substantially pure resolved enantiomers, all possible geometric isomers, and pharmaceutically acceptable salts thereof. The above Formula (I) is shown without a definitive stereochemistry at certain positions. The present invention includes all stereoisomers of Formula (I) and pharmaceutically acceptable salts thereof. Further, mixtures of stereoisomers as well as isolated specific stereoisomers are also included. During the course of the synthetic procedures used to prepare such compounds, or in using racemization or epimerization procedures known to those skilled in the art, the products of such procedures can be a mixture of stereoisomers.

The term "pharmaceutically acceptable salts" refers to salts prepared from pharmaceutically acceptable non-toxic bases or acids. When the compound of the present invention is acidic, its corresponding salt can be conveniently prepared from pharmaceutically acceptable non-toxic bases, including inorganic bases and organic bases. Salts derived from such inorganic bases include aluminum, ammonium, calcium, copper (ic and ous), ferric, ferrous, lithium, magnesium, manganese (ic and ous), potassium, sodium, zinc and the like salts. Particularly preferred are the ammonium, calcium, magnesium, potassium and sodium salts. Salts derived from pharmaceutically acceptable organic non-toxic bases include salts of primary, secondary, and tertiary amines, as well as cyclic amines and substituted amines such as naturally occurring and synthesized substituted amines. Other pharmaceutically acceptable organic non-toxic bases from which salts can be formed include ion exchange resins such as, for example, arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like.

When the compound of the present invention is basic, its corresponding salt can be conveniently prepared from pharmaceutically acceptable non-toxic acids, including inorganic and organic acids. Such acids include, for example, acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid and the like. Particularly preferred are citric, hydrobromic, hydrochloric, maleic, phosphoric, sulfuric, and tartaric acids.

The pharmaceutical compositions of the present invention comprise a compound represented by Formula (I) (or pharmaceutically acceptable salts thereof) as an active ingredient, a pharmaceutically acceptable carrier and optionally other therapeutic ingredients or adjuvants. Such additional therapeutic ingredients include, for example, i) Leukotriene receptor antagonists, ii) Leukotriene biosynthesis inhibitors, and iii) M2/M3 antagonists. The compositions include compositions suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions may be conveniently presented in unit dosage form and prepared by any of the methods well known in the art of pharmacy.

Creams, ointments, jellies, solutions, or suspensions containing the compound of Formula I can be employed for topical use. Mouth washes and gargles are included within the scope of topical use for the purposes of this invention.

Dosage levels from about 0.01 mg/kg to about 140 mg/kg of body weight per day are useful in the treatment of conditions such as asthma, chronic bronchitis, chronic obstructive pulmonary disease (COPD), eosinophilic granuloma, psoriasis and other benign or malignant proliferative skin diseases, endotoxic shock (and associated conditions such as laminitis and colic in horses), septic shock, ulcerative colitis, Crohn's disease, reperfusion injury of the myocardium and brain, inflammatory arthritis, chronic glomerulonephritis, atopic dermatitis, urticaria, adult respiratory distress syndrome, infant respiratory distress syndrome, chronic obstructive pulmonary disease in animals, diabetes insipidus, allergic rhinitis, allergic conjunctivitis, vernal conjunctivitis, arterial restenosis, ortherosclerosis, atherosclerosis, neurogenic inflammation, pain, cough, rheumatoid arthritis, ankylosing spondylitis, transplant rejection and graft versus host disease, hypersecretion of gastric acid, bacterial, fungal or viral induced sepsis or septic shock, inflammation and cytokine-mediated chronic tissue degeneration, osteoarthritis, cancer, cachexia, muscle wasting, depression, memory impairment, tumour growth and cancerous invasion of normal tissues which are responsive to PDE4 inhibition, or alternatively about 0.5 mg to about 7 g per patient per day. For example, inflammation may be effectively treated by the administration of from about 0.01 mg to 50 mg of the compound per kilogram of body weight per day, or alternatively about 0.5 g to about 3.5 g per patient per day. Further, it is understood that the PDE4 inhibiting compounds of this invention can be administered at prophylactically effective dosage levels to prevent the above-recited conditions.

The amount of active ingredient that may be combined with the carrier materials to produce a single dosage form will vary depending upon the host treated and the particular mode of administration. For example, a formulation intended for the oral administration to humans may conveniently contain from about 0.5 mg to about 5 g of active agent, compounded with an appropriate and convenient amount of carrier material which may vary from about 5 to about 95 percent of the total composition. Unit dosage forms will generally contain between from about 1 mg to about 500 mg of the active ingredient, typically 25 mg, 50 mg, 100 mg, 200 mg, 300 mg, 400 mg, 500 mg, 600 mg, 800 mg or 1000 mg.

It is understood, however, that the specific dose level for any particular patient will depend upon a variety of factors including the age, body weight, general health, sex, diet, time of administration, route of administration, rate of excretion, drug combination and the severity of the particular disease undergoing therapy.

In practice, the compounds represented by Formula (I), or pharmaceutically acceptable salts thereof, of this invention can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). Thus, the pharmaceutical compositions of the present invention can be presented as discrete units suitable for oral administration such as capsules, cachets or tablets each containing a predetermined amount of the active ingredient. Further, the compositions can be presented as a powder, as granules, as a solution, as a suspension in an aqueous liquid, as a non-aqueous liquid, as an oil-in-water emulsion or as a water-in-oil liquid emulsion. In addition to the common dosage forms set out above, the compound represented by Formula (I), or pharmaceutically acceptable salts thereof, may also be administered by controlled release means and/or delivery devices. The compositions may be prepared by any of the methods of pharmacy. In general, such methods include a step of bringing into association the active ingredient with the carrier that constitutes one or more necessary ingredients. In general, the compositions are prepared by uniformly and intimately admixing the active ingredient with liquid carriers or finely divided solid carriers or both. The product can then be conveniently shaped into the desired presentation.

Thus, the pharmaceutical compositions of this invention may include a pharmaceutically acceptable carrier and a compound or a pharmaceutically acceptable salt of Formula (I). The compounds of Formula (I), or pharmaceutically acceptable salts thereof, can also be included in pharmaceutical compositions in combination with one or more other therapeutically active compounds.

The pharmaceutical carrier employed can be, for example, a solid, liquid, or gas. Examples of solid carriers include lactose, terra alba, sucrose, talc, gelatin, agar, pectin, acacia, magnesium stearate, and stearic acid. Examples of liquid carriers are sugar syrup, peanut oil, olive oil, and water. Examples of gaseous carriers include carbon dioxide and nitrogen.

In preparing the compositions for oral dosage form, any convenient pharmaceutical media may be employed. For example, water, glycols, oils, alcohols, flavoring agents, preservatives, coloring agents and the like may be used to form oral liquid preparations such as suspensions, elixirs and solutions; while carriers such as starches, sugars, microcrystalline cellulose, diluents, granulating agents, lubricants, binders, disintegrating agents, and the like may be used to form oral solid preparations such as powders, capsules and tablets. Because of their ease of administration, tablets and capsules are the preferred oral dosage units whereby solid pharmaceutical carriers are employed. Optionally, tablets may be coated by standard aqueous or nonaqueous techniques A tablet containing the composition of this invention may be prepared by compression or molding, optionally with one or more accessory ingredients or adjuvants. Compressed tablets may be prepared by compressing, in a suitable machine, the active ingredient in a free-flowing form such as powder or granules, optionally mixed with a binder, lubricant, inert diluent, surface active or dispersing agent. Molded tablets maybe made by molding in a suitable machine, a mixture of the powdered compound moistened with an inert liquid diluent. Each tablet preferably contains from about 0.1 mg to about 500 mg of the active ingredient and each cachet or capsule preferably containing from about 0.1 mg to about 500 mg of the active ingredient.

Pharmaceutical compositions of the present invention suitable for parenteral administration may be prepared as solutions or suspensions of the active compounds in water. A suitable surfactant can be included such as, for example, hydroxypropylcellulose. Dispersions can also be prepared in glycerol, liquid polyethylene glycols, and mixtures thereof in oils. Further, a preservative can be included to prevent the detrimental growth of microorganisms.

Pharmaceutical compositions of the present invention suitable for injectable use include sterile aqueous solutions or dispersions. Furthermore, the compositions can be in the form of sterile powders for the extemporaneous preparation of such sterile injectable solutions or dispersions. In all cases, the final injectable form must be sterile and must be effectively fluid for easy syringability. The pharmaceutical compositions must be stable under the conditions of manufacture and storage; thus, preferably should be preserved against the contaminating action of microorganisms such as bacteria and fungi. The carrier can be a solvent or dispersion medium containing, for example, water, ethanol, polyol (e.g. glycerol, propylene glycol and liquid polyethylene glycol), vegetable oils, and suitable mixtures thereof.

Pharmaceutical compositions of the present invention can be in a form suitable for topical use such as, for example, an aerosol, cream, ointment, lotion, dusting powder, or the like. Further, the compositions can be in a form suitable for use in transdermal devices. These formulations may be prepared, utilizing a compound represented by Formula (I) of this invention, or pharmaceutically acceptable salts thereof, via conventional processing methods. As an example, a cream or ointment is prepared by mixing hydrophilic material and water, together with about 5 wt % to about 10 wt % of the compound, to produce a cream or ointment having a desired consistency.

Pharmaceutical compositions of this invention can be in a form suitable for rectal administration wherein the carrier is a solid. It is preferable that the mixture forms unit dose suppositories. Suitable carriers include cocoa butter and other materials commonly used in the art. The suppositories may be conveniently formed by first admixing the composition with the softened or melted carrier(s) followed by chilling and shaping in moulds.

In addition to the aforementioned carrier ingredients, the pharmaceutical formulations described above may include, as appropriate, one or more additional carrier ingredients such as diluents, buffers, flavoring agents, binders, surface-active agents, thickeners, lubricants, preservatives (including anti-oxidants) and the like. Furthermore, other adjuvants can be included to render the formulation isotonic with the blood of the intended recipient. Compositions containing a compound described by Formula (I), or pharmaceutically acceptable salts thereof, may also be prepared in powder or liquid concentrate form.

The compounds and pharmaceutical compositions of this invention have been found to exhibit biological activity as PDE4 inhibitors. Accordingly, another aspect of the invention is the treatment in mammals of, for example, asthma, chronic bronchitis, chronic obstructive pulmonary disease (COPD), eosinophilic granuloma, psoriasis and other benign or malignant proliferative skin diseases, endotoxic shock (and associated conditions such as laminitis and colic in horses), septic shock, ulcerative colitis, Crohn's disease, reperfusion injury of the myocardium and brain, inflammatory arthritis, chronic glomerulonephritis, atopic dermatitis, urticaria, adult respiratory distress syndrome, chronic obstructive pulmonary disease in animals, diabetes insipidus, allergic rhinitis, allergic conjunctivitis, vernal conjunctivitis, arterial restenosis, ortherosclerosis, atherosclerosis, neurogenic inflammation, pain, cough, rheumatoid arthritis, ankylosing spondylitis, transplant rejection and graft versus host disease, hypersecretion of gastric acid, bacterial, fungal or viral induced sepsis or septic shock, inflammation and cytokine-mediated chronic tissue degeneration, osteoarthritis, cancer, cachexia, muscle wasting, depression, memory impairment, tumour growth and cancerous invasion of normal tissues—maladies that are amenable to amelioration through inhibition of the PDE4 isoenzyme and the resulting elevated cCAMP levels—by the administration of an effective amount of the compounds of this invention. The term "mammals" includes humans, as well as other animals such as, for example, dogs, cats, horses, pigs, and cattle. Accordingly, it is understood that the treatment of mammals other than humans is the treatment of clinical correlating afflictions to those above recited examples that are human afflictions.

Further, as described above, the compound of this invention can be utilized in combination with other therapeutic compounds. In particular, the combinations of the PDE4 inhibiting compound of this invention can be advantageously used in combination with i) Leukotriene receptor antagonists, ii) Leukotriene biosynthesis inhibitors, or iii) M2/M3 antagonists.

Assays Demonstrating Biological Activity

LPS and FMLP-Induced TNF-α and LTB$_4$ Assays in Human Whole Blood

Whole blood provides a protein and cell-rich milieu appropriate for the study of biochemical efficacy of anti-inflammatory compounds such as PDE4-selective inhibitors. Normal non-stimulated human blood does not contain detectable levels of TNF-α and LTB$_4$. Upon stimulation with LPS, activated monocytes express and secrete TNF-α up to 8 hours and plasma levels remain stable for 24 hours. Published studies have shown that inhibition of TNF-α by increasing intracellular cAMP via PDE4 inhibition and/or enhanced adenylyl cyclase activity occurs at the transcriptional level. LTB$_4$ synthesis is also sensitive to levels of intracellular cAMP and can be completely inhibited by PDE4-selective inhibitors. As there is little LTB$_4$ produced during a 24 hour LPS stimulation of whole blood, an additional LPS stimulation followed by fMLP challenge of human whole blood is necessary for LTB$_4$ synthesis by activated neutrophils. Thus, by using the same blood sample, it is possible to evaluate the potency of a compound on two surrogate markers of PDE4 activity in the whole blood by the following procedure.

Fresh blood was collected in heparinized tubes by venipuncture from healthy human volunteers (male and female). These subjects had no apparent inflammatory conditions and had not taken any NSAIDs for at least 4 days prior to blood collection. 500 µL aliquots of blood were pre-incubated with either 2 µL of vehicle (DMSO) or 2 µL of test compound at varying concentrations for 15 minutes at 37° C. This was followed by the addition of either 10 µL vehicle (PBS) as blanks or 10 µL LPS (1 µg/mL final concentration, #L-2630 (Sigma Chemical Co., St.Louis, Mo.) from E. coli, serotype 0111:B4; diluted in 0.1% w/v BSA (in PBS)). After 24 hours of incubation at 37° C., another 10 µL of PBS (blank) or 10 µL of LPS (1 µg/mL final concentration) was added to blood and incubated for 30 minutes at 37° C. The blood was then challenged with either 10 µL of PBS (blank) or 10 µL of fMLP (1 µM final concentration, #F-3506 (Sigma); diluted in 1% w/v BSA (in PBS)) for 15 minutes at 37° C. The blood samples were centrifuged at 1500×g for 10 minutes at 4° C. to obtain plasma. A 50 µL aliquot of plasma was mixed with 200 µL methanol for protein precipitation and centrifuged as above. The supernatant was assayed for LTB$_4$ using an enzyme immunoassay kit (#520111 from Cayman Chemical Co., Ann Arbor, Mich.) according to the manufacturer's procedure. TNF-α was assayed in diluted plasma (in PBS) using an ELISA kit (Cistron Biotechnology, Pine Brook, N.J.) according to manufacturer's procedure. The IC$_{50}$ values of Examples 1–36 generally ranged from 0.01 µM to 20 µM.

Anti-Allergic Activity In Vivo

Compounds of the invention have been tested for effects on an IgE-mediated allergic pulmonary inflammation induced by inhalation of antigen by sensitized guinea pigs. Guinea pigs were initially sensitized to ovalbumin under mild cyclophosphamide-induced immunosuppression, by intraperitoneal injection of antigen in combinations with aluminum hydroxide and pertussis vaccine. Booster doses of antigen were given two and four weeks later. At six weeks, animals were challenged with aerosolized ovalbumin while under cover of an intraperitoneally administered antihistamine agent (mepyramine). After a further 48 h, bronchial alveolar lavages (BAL) were performed and the numbers of eosinophils and other leukocytes in the BAL fluids were counted. The lungs were also removed for histological examination for inflammatory damage. Administration of compounds of the Examples (0.001–10 mg/kg i.p. or p.o.), up to three times during the 48 h following antigen challenge, lead to a significant reduction in the eosinophilia and the accumulation of other inflammatory leukocytes. There was also less inflammatory damage in the lungs of animals treated with compounds of the Examples.

SPA Based PDE Activity Assay Protocol

Compounds which inhibit the hydrolysis of cAMP to AMP by the type-IV cAMP-specific phosphodiesterases were screened in a 96-well plate format as follows:

In a 96 well-plate at 30° C. was added the test compound (dissolved in 2 µL DMSO), 188 mL of substrate buffer containing [2,8-$^3$H] adenosine 3',5'-cyclic phosphate (cAMP, 100 nM to 50 µM), 10 mM MgCl$_2$, 1 mM EDTA, 50 mM Tris, pH 7.5. The reaction was initiated by the addition of 10 mL of human recombinant PDE4 (the amount was controlled so that ~10% product was formed in 10 min.). The reaction was stopped after 10 min. by the addition of 1 mg of PDE-SPA beads (Amersham Pharmacia Biotech, Inc., Piscataway, N.J.). The product AMP generated was quantified on a Wallac Microbeta® 96-well plate counter (EG&G Wallac Co., Gaithersburg, Md.). The signal in the absence of enzyme was defined as the background. 100% activity was defined as the signal detected in the presence of enzyme and DMSO with the background subtracted. Percentage of inhibition was calculated accordingly. IC$_{50}$ value was approximated with a non-linear regression fit using the standard 4-parameter/multiple binding sites equation from a ten point titration.

The $IC_{50}$ values of Examples 1–36 were determined with 100 nM cAMP using the purified GST fusion protein of the human recombinant phosphodiesterase IVa (met-248) produced from a baculovirus/Sf-9 expression system. The $IC_{50}$ values of Examples 1–36 generally ranged from 0.05 nm to 200 nm.

The examples that follow are intended as an illustration of certain preferred embodiments of the invention and no limitation of the invention is implied.

Unless specifically stated otherwise, the experimental procedures were performed under the following conditions. All operations were carried out at room or ambient temperature—that is, at a temperature in the range of 18–25° C. Evaporation of solvent was carried out using a rotary evaporator under reduced pressure (600–4000 pascals: 4.5–30 mm. Hg) with a bath temperature of up to 60° C. The course of reactions was followed by thin layer chromatography (TLC) and reaction times are given for illustration only. Melting points are uncorrected and 'd' indicates decomposition. The melting points given are those obtained for the materials prepared as described. Polymorphism may result in isolation of materials with different melting points in some preparations. The structure and purity of all final products were assured by at least one of the following techniques: TLC, mass spectrometry, nuclear magnetic resonance (NMR) spectrometry or microanalytical data. Yields are given for illustration only. When given, NMR data is in the form of delta (δ) values for major diagnostic protons, given in parts per million (ppm) relative to tetramethylsilane (TMS) as internal standard, determined at 300 MHz, 400 MHz or 500 MHz using the indicated solvent. Conventional abbreviations used for signal shape are: s. singlet; d. doublet; t. triplet; m. multiplet; br. broad; etc. In addition, "Ar" signifies an aromatic signal. Chemical symbols have their usual meanings; the following abbreviations have also been used: v (volume), w (weight), b.p. (boiling point), m.p. (melting point), L (liter(s)), mL (milliliters), g (gram(s)), mg (milligrams(s)), mol (moles), mmol (millimoles), eq (equivalent(s)).

Methods of Synthesis

The compounds of Formula (I) of the present invention can be prepared according to the synthetic routes outlined in Schemes 1 to 3 below and by following the methods described therein. It is obvious to one skilled in the art that resolution of compounds bearing stereogenic centers, such as VII, XIII to XVI for example, or compounds of Formula I and Ia, can be accomplished by one of several methods, including HPLC with a chiral column, or formation and crystallization of a salt prepared by reaction of the compound with a chiral acid or base. The substituents are the same as in Formula (I) except where defined otherwise. It is apparent that $R^P$ is readily incorporated into the compounds of this invention by starting with the appropriately substituted alkyl pyridylacetate reactant.

Scheme 1

The thiazole tertiary alcohols of Formula I may be prepared in a multi-step sequence from the requisite dialkoxy-aldehyde III and an appropriately substituted thiazole II as presented in Scheme 1 below. Addition of a metalated thiazole, prepared by regioselective metalation of thiazole II with a base such as n-butyllithium in a suitable solvent such as ether or THF, to III provides secondary alcohol IV. Conversion of IV into the corresponding secondary chloride or bromide V is accomplished by reaction with an appropriate halogenating reagent, such as thionyl chloride or thionyl bromide, and an organic base, such as pyridine, diisopropylethylamine or triethylamine, in an organic solvent such as dichloromethane or toluene. Alkylation of the anion derived from deprotonation of an alkyl pyridylacetate with an appropriate base, such as lithium, sodium or potassium bis(trimethylsilyl)amide, with the halide V in an appropriate organic solvent such as THF and/or HMPA (hexamethylphosphoramide), provides the ester VI. Ester VI is decarboxylated by one of several methods to give the pyridine VII.

In one method, heating VI in the presence of aqueous hydroxide, such as sodium hydroxide, in a mixture of protic and aprotic organic solvents, such as methanol or ethanol and THF, followed by acidification of the intermediate carboxylic acid with mineral acid, such a hydrochloric acid, provides VII. Alternatively, heating the carboxylic acid in an organic solvent such as dimethylsulfoxide provides VII.

Removal of the alcohol protecting group, for example by treating with an organic acid such as trifluoroacetic acid in an organic solvent such a dichloromethane (if P=2-(trimethylsilyl)ethoxymethoxy), affords the pyridines of Formula Ia of the present invention. Reaction of Ia with an oxidizing agent, such as m-CPBA (meta-chloroperoxybenzoic acid) or MMPP (monoperoxyphthalic acid, magnesium salt) provides the N-oxides of Formula I of the present invention. Alternatively, oxidation of VII as described above for Ia, followed by deprotection affords the N-oxides of Formula I of the present invention.

Scheme 1

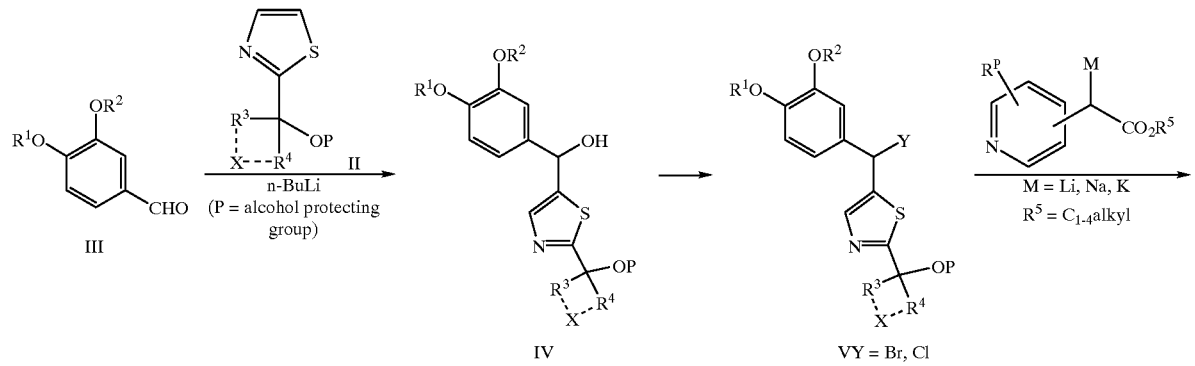

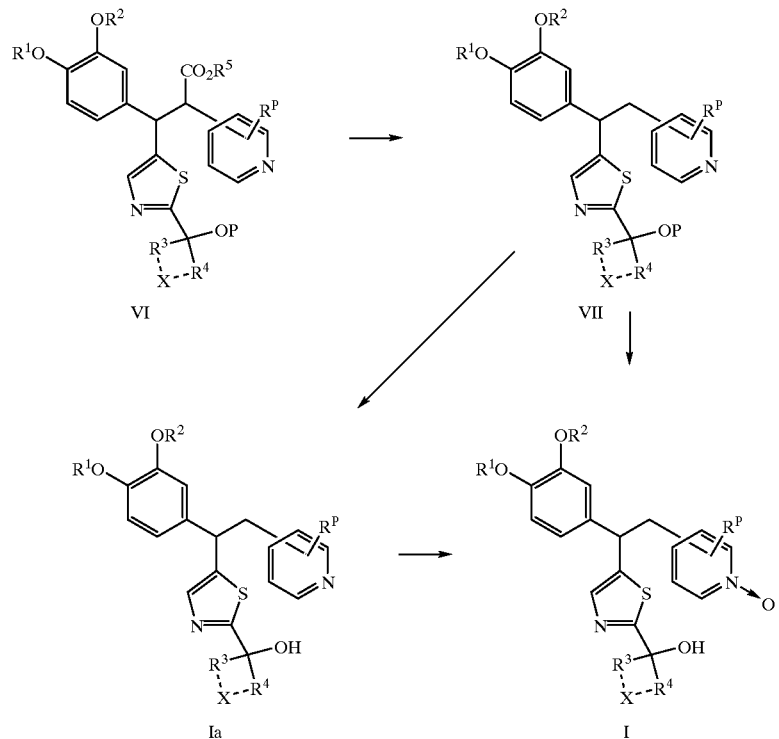

Scheme 2

Alternatively, compounds of Formula I can be prepared using the route described in Scheme 2 below. Alkylation of the anion derived from deprotonation of an alkyl pyridylacetate N-oxide with an appropriate base, such as lithium, sodium or potassium bis(trimethylsilyl)amide, with the secondary halide V in an appropriate organic solvent such as THF and/or HMPA, provides the ester VIII. Decarboxylation and deprotection as described in Scheme 1 provides the N-oxides of Formula I of the present invention.

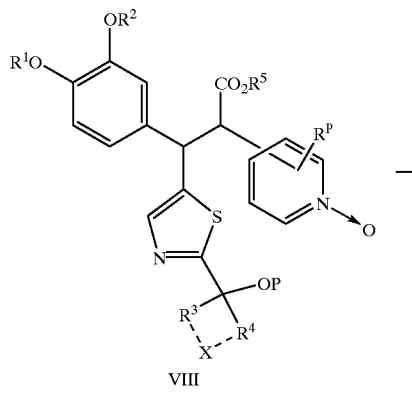

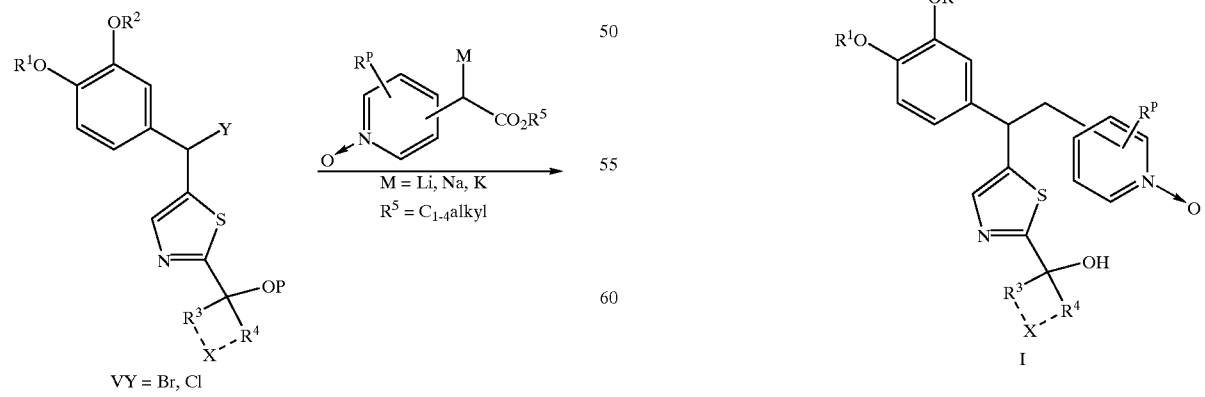

Scheme 3

The thiazole tertiary alcohols of Formula I may also be prepared in a multi-step sequence from the requisite dialkoxyaldehyde III and an appropriately substituted thiazole IX as presented in Scheme 3 below via the intermediacy of the aldehyde XIV. Addition of a metalated thiazole, prepared by regioselective metalation of thiazole IX in a suitable solvent such as ether or THF, to III provides secondary alcohol X. Conversion of X into the corresponding secondary chloride or bromide XI is accomplished by reaction with an appropriate halogenating reagent, such as thionyl chloride or thionyl bromide, and an organic base, such as pyridine, diisopropylethylamine or triethylamine, in an organic solvent such as dichloromethane or toluene. Alkylation of the anion derived from deprotonation of an alkyl pyridylacetate with an appropriate base, such as lithium, sodium or potassium bis(trimethylsilyl)amide, with the halide XI in an appropriate organic solvent such as THF and/or HMPA, provides the ester XII. Ester XII is decarboxylated as described in Scheme 1 above to give XIII. Removal of the aldehyde protecting group by reaction of XIII with an acid, such as hydrochloric acid or p-toluenesulfonic acid, provides aldehyde XIV. Treatment of aldehyde XIV with a nucleophilic reagent, such as an organolithium, organocerium or Grignard reagent, in an organic solvent, such as ether or THF, provides the secondary alcohol XV. Oxidation of XV with an oxidizing agent, such as manganese dioxide or by Swern oxidation, affords ketone XVI. Further reaction of ketone XVI with a second nucleophilic reagent, such as an organolithium, organocerium or Grignard reagent, in an organic solvent such as ether or THF, provides the pyridines of Formula Ia of the present invention. Reaction of Ia with an oxidizing agent, such as m-CPBA or MMPP provides the N-oxides of Formula I of the present invention.

Scheme 3

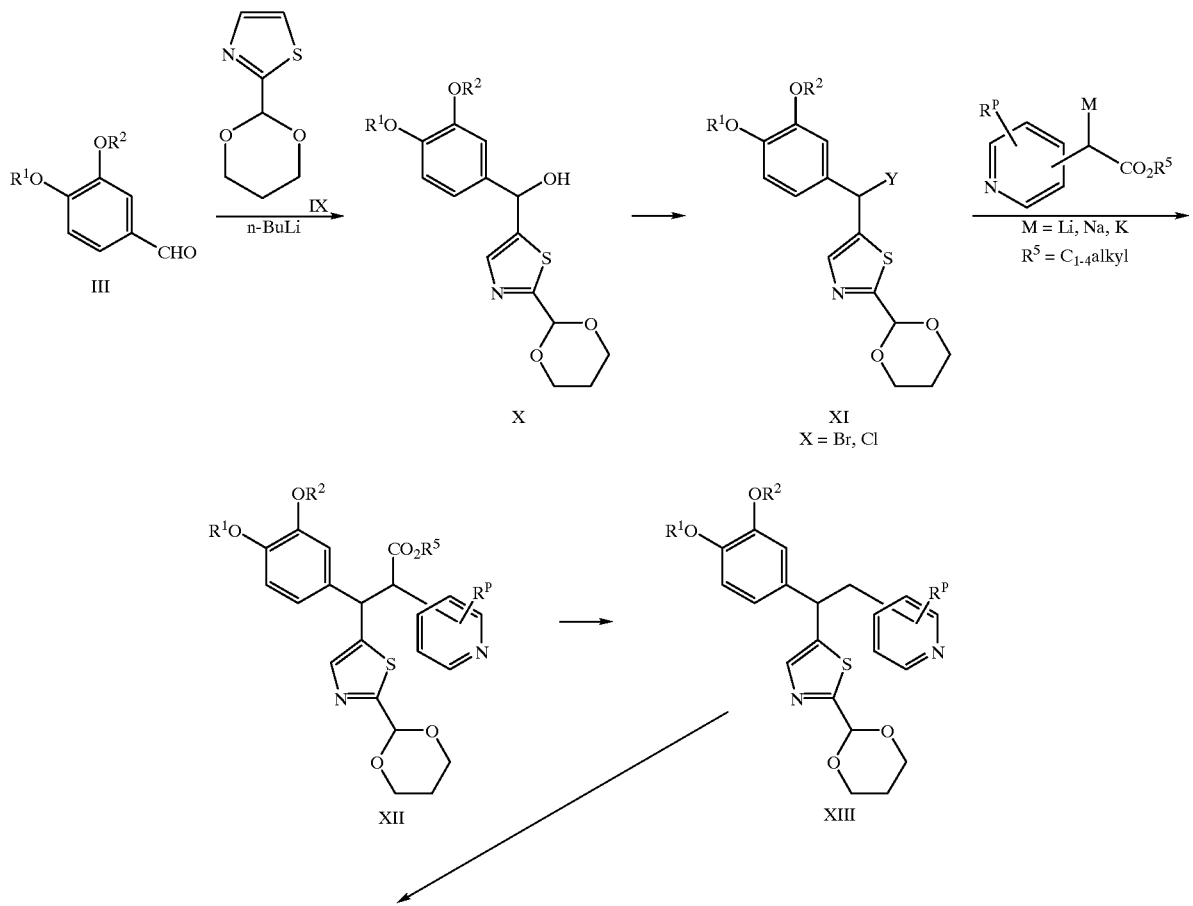

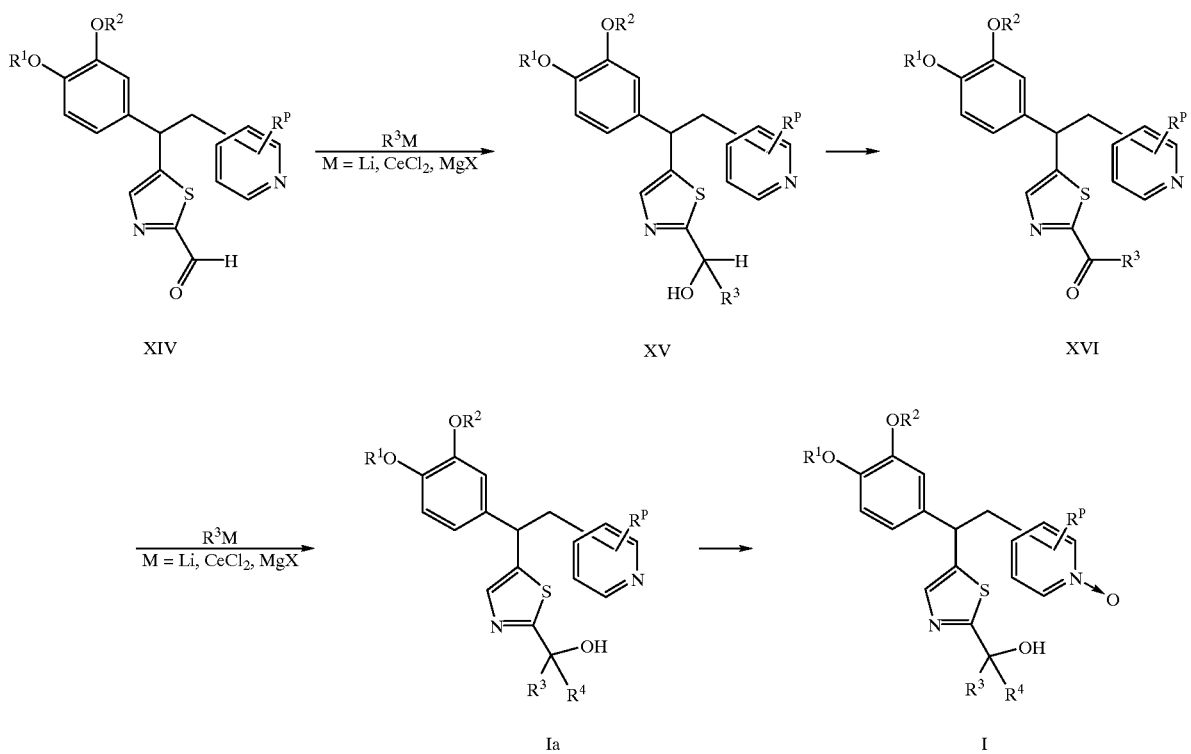

Examples 1–36

Examples 1–36 are summarized in the table below:

| Example | R1 | R2 | R3 | R4 | Pyridine | n |
|---|---|---|---|---|---|---|
| 1 | $CHF_2$ | $CHF_2$ | $CH_3$ | $CH_3$ | 4-Pyr | 1 |
| 2 | $CHF_2$ | $CHF_2$ | $CH_3$ | $CH_3$ | 4-Pyr | 1 |
| 3 | $CHF_2$ | $CHF_2$ | $CF_3$ | H | 4-Pyr | 0 |
| 4 | $CHF_2$ | $CHF_2$ | $CF_3$ | H | 4-Pyr | 1 |
| 5 | $CHF_2$ | $CHF_2$ | $CF_3$ | $CF_3$ | 4-Pyr | 0 |
| 6 | $CHF_2$ | $CHF_2$ | $CF_3$ | $CF_3$ | 4-Pyr | 1 |
| 7 | $CHF_2$ | $CHF_2$ | $CF_3$ | $CH_3$ | 4-Pyr | 1 |
| 8 | $CHF_2$ | $CHF_2$ | Ph | H | 4-Pyr | 1 |
| 9 | $CHF_2$ | $CHF_2$ | Ph | $CH_3$ | 4-Pyr | 1 |
| 10 | $CHF_2$ | $CHF_2$ | Ph | $CF_3$ | 4-Pyr | 1 |
| 11 | $CHF_2$ | $CHF_2$ | Ph | Et | 4-Pyr | 1 |
| 12 | $CHF_2$ | $CHF_2$ | c-Hex | H | 4-Pyr | 0 |
| 13 | $CHF_2$ | $CHF_2$ | c-Hex | $CF_3$ | 4-Pyr | 1 |
| 14 | $CHF_2$ | $CHF_2$ | 4-EtPh | $CH_3$ | 4-Pyr | 1 |
| 15 | $CHF_2$ | $CHF_2$ | 4-EtPh | $CF_3$ | 4-Pyr | 1 |
| 16 | $CHF_2$ | $CHF_2$ | 4-FPh | $CH_3$ | 4-Pyr | 1 |
| 17 | $CHF_2$ | $CHF_2$ | 4-FPh | $CF_3$ | 4-Pyr | 1 |
| 18 | $CHF_2$ | $CHF_2$ | 2-(5-Br)Pyr | $CF_3$ | 4-Pyr | 1 |
| 19 | $CHF_2$ | $CHF_2$ | 3-(6-Br)Pyr | $CF_3$ | 4-Pyr | 1 |
| 20 | $CHF_2$ | $CHF_2$ | —$(CH_2)_3$— | | 4-Pyr | 1 |
| 21 | $CHF_2$ | $CHF_2$ | —$(CH_2)_5$— | | 4-Pyr | 1 |
| 22 | $CHF_2$ | c-but | $CH_3$ | $CH_3$ | 4-Pyr | 1 |
| 23 | $CHF_2$ | c-but | $CH_3$ | $CH_3$ | 4-Pyr | 1 |
| 24 | $CHF_2$ | c-but | $CF_3$ | $CF_3$ | 4-Pyr | 0 |
| 25 | $CHF_2$ | c-but | $CF_3$ | $CF_3$ | 4-Pyr | 1 |
| 26 | $CHF_2$ | c-but | $CH_3$ | $CH_3$ | 3-Pyr | 0 |
| 27 | $CHF_2$ | c-but | $CH_3$ | $CH_3$ | 3-Pyr | 0 |
| 28 | $CHF_2$ | c-but | $CH_3$ | $CH_3$ | 3-Pyr | 1 |
| 29 | $CHF_2$ | c-but | $CH_3$ | $CH_3$ | 3-Pyr | 1 |
| 30 | $CHF_2$ | c-but | $CF_3$ | $CF_3$ | 3-Pyr | 1 |
| 31 | $CHF_2$ | c-but | $CF_3$ | $CF_3$ | 3-Pyr | 1 |
| 32 | $CHF_2$ | c-but | $CF_3$ | $CF_3$ | 2-Pyr | 1 |
| 33 | $CHF_2$ | c-pr | $CH_3$ | $CH_3$ | 4-Pyr | 1 |
| 34 | $CHF_2$ | c-pr | $CF_3$ | $CF_3$ | 3-Pyr | 1 |
| 35 | $CHF_2$ | c-pr | $CF_3$ | $CF_3$ | 3-Pyr | 1 |
| 36 | $CHF_2$ | c-pr | $CF_3$ | $CF_3$ | 3-Pyr | 1 |

In the table above, "c-but" represents cyclobutyl, "c-pr" represents cyclopropyl, "c-pent" represents cyclopentyl, "c-Hex" represents cyclohexyl, "4-Etph" represents 4-ethylphenyl, "4-FPh" represents 4-fluorophenyl, "Ph" represents phenyl, "Pyr" represents pyridyl, "2-(5-Br)Pyr" represents 2-(5-bromo)pyridyl, and "3-(6-Br)Pyr" is represents 3-(6-bromo)pyridyl.

EXAMPLES

All examples are mixtures of stereoisomers, either racemic mixtures (indicated as (±)) or racemic mixtures of diastereomers (indicated as (±/±)) unless stated otherwise. In those cases in which the stereoisomers have been separated, they are so indicated by Enantiomer 1, 2 etc. or Diastereomer 1, 2 etc.

Preparation of Intermediates

Intermediate 1

(±)-4-{2-[3,4-Bis(difluoromethoxy)phenyl]-2-[5-(2-formyl)thiazolyl]ethyl}pyridine

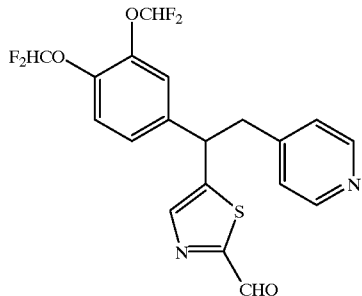

Step 1: 2-(1,3-Dioxan-2-yl)thiazole

A solution of 2-formylthiazole (10 g, 88 mmol), 1,3-propanediol (8 mL) and p-TsOH (100 mg) in benzene (110 mL) was heated at reflux temperature for 15 h with removal of water using a Dean-Stark apparatus. The mixture was cooled to room temperature and washed twice with sat. aq. $NaHCO_3$, twice with water and concentrated. The resulting solid was crystallized from hexane to provide 2-(1,3-Dioxan-2-yl)thiazole as a tan solid (10.4 g).

Step 2: (±)-3,4-Bis(difluoromethoxy)phenyl-5-[2-(1,3-dioxan-2-yl)]thiazolylcarbinol To a solution of n-BuLi (37.2 mL of a 2.5M solution in hexane, 93 mmol) at −65° C. was added a solution of 2-(1,3-dioxan-2-yl)thiazole from Step 1 (17.6 g, 93 mmol) in anhydrous ether (200 mL) over 30 min, maintaining the internal temperature at −65 to −70° C. After a further 20 min, 3,4-bis(difluoromethoxy)benzaldehyde (22.1 g, 93 mmol) in anhydrous ether (150 mL) was added over 30 min. The mixture was stirred at −70° C. for 1 h and then sat. aq. $NH_4Cl$ (200 mL) was added. The mixture was allowed to warm to room temperature and then partitioned with ether and water. The organic layer was dried ($MgSO_4$) and concentrated. Flash chromatography of the residue (silica gel; ethyl acetate/hexane 2:1) provided (±)-3,4-Bis (difluoromethoxy)phenyl-5-[2-(1,3-dioxan-2-yl)] thiazolylcarbinol as a yellow syrup (18.4 g).

Step 3: (±)-4-{2-[3,4-Bis(difluoromethoxy)phenyl]-2-[5-(2-(1,3-dioxan-2-yl))thiazolyl]ethyl}pyridine To a solution of pyridine (10.7 mL, 132 mmol) in toluene (125 mL) at 0° C. was slowly added thionyl bromide (5.12 mL, 66 mmol) and the resulting mixture was stirred at this temperature for 10 min. To this mixture was slowly added, over 10 min, a solution of (±)-3,4-bis(difluoromethoxy) phenyl-5-[2-(1,3-dioxan-2-yl)]thiazolylcarbinol from Step 2 (18 g, 44 mmol) in toluene (75 mL). The mixture was stirred at 0° C. for 45 min and then the solids that were formed were allowed to settle. The supernatant was filtered through a pad of silica gel pre-wetted with ethyl acetate. The solids were washed with ethyl acetate and filtered as well. The combined filtrates were concentrated at a bath temperature <40° C. to provide the crude bromide that was used immediately.

To a solution of ethyl 4-pyridylacetate (26.9 mL, 176 mmol) in THF (250 mL) and HMPA (30.6 mL, 176 mmol) at 0° C. was added sodium bis(trimethylsilyl)amide (176 mL of a 1M solution in THF, 176 mmol). The resulting mixture was stirred for 45 min and then a THF (104 mL) solution of the bromide prepared above was added over 20 min and then stirred for 15 h at 25° C. The stirred mixture was poured into sat. $NH_4Cl$ (500 mL) and extracted twice with ethyl acetate. The combined organics were washed successively with water (3×), brine, dried ($MgSO_4$) and concentrated to give a thick oil. This material was dissolved in a mixture of THF/MeOH/1N NaOH (2:1:1, 1 L) and the mixture was heated at reflux for 1 h. The volatiles were removed on the rotovap, water (250 mL) was added, and then 1N HCl was slowly added, bringing the pH to approximately 5. The mixture was extracted three times with ethyl acetate and the combined organics were washed with water (3×), dried ($MgSO_4$) and concentrated. Flash chromatography of the residue (silica gel; ethyl acetate/ethanol 95:5) provided (±)-4-{2-[3,4-Bis(difluoromethoxy)phenyl]-2-[5-(2-(1,3-dioxan-2-yl))thiazolyl]ethyl}pyridine as a yellow syrup (15.2 g).

Step 4: (±)-4-{2-[3,4-Bis(difluoromethoxy)phenyl]-2-[5-(2-formyl)thiazolyl]ethyl}pyridine A mixture of (±)-4-{2-[3,4-bis(difluoromethoxy)phenyl]-2-[5-(2-(1,3-dioxan-2-yl))thiazolyl]ethyl}pyridine from Step 3 (15 g, 31 mmol) and 2N HCl (150 mL) in THF (200 mL) was heated at reflux for 20 h. The mixture was cooled to room temperature, diluted with water (500 mL) and then the pH was adjusted to 8 by the addition of 2.5N NaOH. The mixture was extracted with ether (3×) and the combined organics were washed with water (2×), brine, dried ($MgSO_4$) and concentrated. Flash chromatography of the residue (silica gel; ethyl acetate) provided the (±)-4-{2-[3,4-Bis (difluoromethoxy)phenyl]-2-[5-(2-formyl)thiazolyl] ethyl}pyridine as an amber syrup (10.1 g).

Thiazole 1

2-{1-methyl-1-[(2-trimethylsilylethoxy)methoxy]ethyl}thiazole

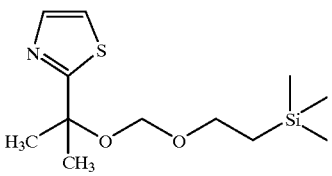

Step 1: 2-[(1-Hydroxy-1-methyl)ethyl]thiazole

To a solution of thiazole (5 g, 58.8 mmol) in anhydrous ether at −78° C. was slowly added over 5 min n-BuLi (40.4 mL of a 1.65M solution in hexane, 64.2 mmol). The resulting mixture was stirred for 20 min and then acetone (5.6 mL, 76.4 mmol) was slowly added. After 25 min, the mixture was poured into 25% aq. $NH_4OAc$ and the resulting mixture was extracted with ethyl acetate (5×). The combined organics were washed with brine, dried ($MgSO_4$) and concentrated. The residual oil (8.9 g) was used as such in the next reaction.

Step 2: 2-{1-Methyl-1-[(2-trimethylsilylethoxy)methoxy]ethyl}thiazole

To a solution of the alcohol 2-[(1-Hydroxy-1-methyl) ethyl]thiazole from Step 1 (8.9 g, 59 mmol) and Hunig's base (26 mL, 148 mmol) in dichloromethane (75 mL) at room temperature was added 2-(trimethylsilyl) ethoxymethyl chloride (12.5 mL, 70.8 mmol). The resulting solution was stirred at room temperature for 1 h, at 50° C. for 3.5 h and finally at room temperature for 15 h. The mixture was poured into 25% aq. NH₄OAc (200 mL) and the resulting mixture was extracted with ethyl acetate (3×). The combined organics were washed with brine, dried (MgSO₄) and concentrated. Flash chromatography of the residue (silica gel; hexane/ethyl acetate 9:1) provided the 2-{1-Methyl-1-[(2-trimethylsilylethoxy)methoxy]ethyl}thiazole product as a yellow liquid (9.6 g).

Thiazole 2

2-{1-trifluoromethyl-1-[(2-trimethylsilylethoxy) methoxy]-2,2,2-trifluoroethyl}thiazole

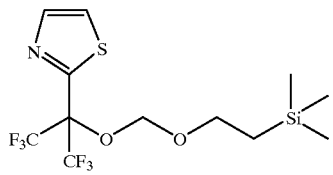

Step 1: 2-[(1-Hydroxy-1-trifluoromethyl)-2,2,2-trifluoroethyl]thiazole

To a solution of n-BuLi (425 mL of a 1.3M solution in hexane, 552 mmol) in anhydrous ether (400 mL) at −78° C. was slowly added over 45 min a solution of thiazole (42.7 g, 502 mmol) in anhydrous ether (400 mL). The resulting mixture was stirred for 15 min and then hexafluoroacetone was bubbled into the mixture for 30 min with the bath temperature maintained between −60 to −70° C. The mixture was allowed to warm to room temperature and then poured into 25% aq. NH₄OAc. The resulting mixture was extracted with ether and then the aqueous phase was acidified to ~pH 4 with conc. HCl. The aqueous phase was extracted with ether (2×). The combined organics were washed with brine, dried (Na₂SO₄) and concentrated at <40° C. The residual liquid was distilled at ~10 mm/Hg and the fractions distilling from 50 to 100° C. was collected. The 2-[(1-Hydroxy-1-trifluoromethyl)-2,2,2-trifluoroethyl]thiazole compound (93 g) was obtained as a liquid and used as such in the next reaction.

Step 2: 2-{1-Trifluoromethyl-1-[(2-trimethylsilylethoxy)methoxy]-2,2,2-trifluoroethyl}thiazole To a solution of the alcohol from Step 1 (93 g, 382 mmol) and Hunig's base (133 mL, 764 mmol) in dichloromethane (1.2 L) at 0° C. was added 2-(trimethylsilyl)ethoxymethyl chloride (88 mL, 497 mmol) over 15 min. The resulting solution was stirred at room temperature for 15 h. The mixture diluted with ether (1 L) and then was poured into 25% aq. NH₄OAc (500 mL). The phases were separated and the aqueous phase was extracted with ether. The combined organics were washed with brine, dried (Na₂SO₄) and concentrated. Flash chromatography of the residue (silica gel; hexane/ethyl acetate 95:5 to 9:1) provided 2-{1-Trifluoromethyl-1-[(2-trimethylsilylethoxy)methoxy]-2,2,2-trifluoroethyl}thiazole as a yellow liquid (99 g).

Thiazole 3

2-{1-trifluoromethyl-1-[(2-trimethylsilyethoxy) methoxy]ethyl}thiazole

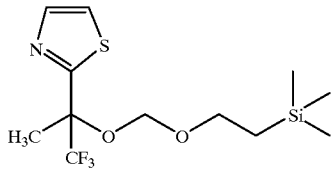

Step 1: 2-[(1-Hydroxy-1-trifluoromethyl)ethyl]thiazole

To a solution of n-BuLi (107 mL of a 1.2 M solution in hexane, 129 mmol) in anhydrous ether (100 mL) at −78 ° C. was slowly added a solution of thiazole (10 g, 117 mmol) in anhydrous ether (100 mL). The resulting mixture was stirred for 20 min and then 1,1,1-trifluoroacetone (12.5 mL, 140 mmol) was added over 5 min. The mixture was stirred for 1 h at −78° C. and then allowed to warm for 15 min. Sat. aq. NH₄Cl was added and the phases were separated. The aqueous phase was acidified to ~pH 1 with 6N HCl and was extracted with ether. The combined organics were washed with brine, dried (Na₂SO₄) and concentrated. The residual liquid (12 g) was used as such in the next reaction.

Step 2: 2-{1-Trifluoromethyl-1-[(2-trimethylsilylethoxy)methoxy]ethyl}thiazole

To a solution of the alcohol 2-[(1-Hydroxy-1-trifluoromethyl)ethyl]thiazole from Step 1 (3 g, 15.2 mmol) in DMF (75 mL) at 0° C. was added sodium hydride (170 mg, 16.7 mmol) in two portions. The mixture was stirred at 0° C. for 15 min, at room temperature for 15 min and then 2-(trimethylsilyl)ethoxymethyl chloride (2.7 mL, 15.2 mmol) was added over 5 min. The resulting solution was stirred at room temperature for 1 h and then cooled to 0° C. 25% aq. NH₄OAc was added and the mixture was diluted with ether (300 mL). The phases were separated and the organic phase was washed with water (4×). The combined aqueous were re-extracted with ether. The combined organics were washed with brine, dried (Na₂SO₄) and concentrated. Flash chromatography of the residue (silica gel; hexane/ethyl acetate 85:15 to 4: 1) provided 2-{1-Trifluoromethyl-1-[(2-trimethylsilylethoxy)methoxy] ethyl}thiazole as a yellow liquid (3.4 g).

Thiazole 4

2-{1-[(2-trimethylsilylethoxy)methoxy] cyclobutyl}thiazole

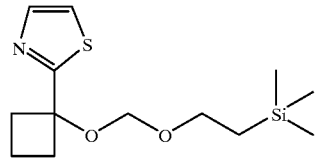

Step 1: 2-[(1-Hydroxy)cyclobutyl]thiazole

To a solution of n-BuLi (36 mL of a 2.5M solution in hexane, 90 mmol) in anhydrous ether (100 mL) at −78° C was slowly added a solution of thiazole (6.35 g, 74.6 mmol) in anhydrous ether (60 mL). The resulting mixture was stirred for 1 h and then cyclobutanone (10.4 g, 148 mmol) in ether (20 mL) was added over 5 min. The mixture was stirred for 2 h at −78° C. and then sat. aq. NH₄Cl was added and the phases were separated. The aqueous phase was extracted with ethyl acetate (3×) and the combined organics were washed with water, brine, dried (MgSO₄) and concentrated. Flash chromatography of the residue (silica gel; hexane/ethyl acetate 4:1 to 7:3) provided 2-[(1-Hydroxy) cyclobutyl]thiazole (5 g).

Step 2: 2-{1-[(2-Trimethylsilylethoxy)methoxy] cyclobutyl}thiazole

To a solution of the alcohol 2-[(1-Hydroxy)cyclobutyl] thiazole from Step 1 (5 g, 32 mmol) and Hunig's base (10.4 mL, 60 mmol) in dichloromethane (100 mL) at 0° C. was added 2-(trimethylsilyl)ethoxymethyl chloride (6.5 mL, 36.7 mmol). The resulting solution was stirred at 0° C. for 1 h, was heated at reflux temperature for 3.5 h and finally was stirred at room temperature for 15 h. Sat. aq. NH₄Cl was added and the resulting mixture was extracted with dichloromethane (3×). The combined organics were washed with water, brine, dried (MgSO₄) and concentrated. Flash chromatography of the residue (silica gel; dichloromethane to dichloromethane/ethyl acetate 95:5) provided 2-{1-[(2-Trimethylsilylethoxy)methoxy]cyclobutyl}thiazole (2 g).

Thiazole 5

2-{1-[(2-trimethylsilylethoxy)methoxy] cyclohexyl}thiazole

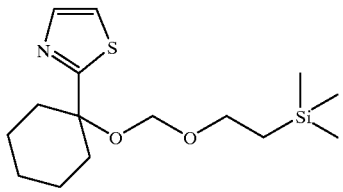

Step 1: 2-[(1-Hydroxy)cyclohexyl]thiazole

To a solution of n-BuLi (22 mL of a 2.5M solution in hexane, 55 mmol) in anhydrous ether (60 mL) at −78° C. was slowly added a solution of thiazole (3.94 g, 46 mmol) in anhydrous ether (30 mL). The resulting mixture was stirred for 1 h and then cyclohexanone (9.6 mL, 93 mmol) in ether (25 mL) was added over 5 min. The mixture was stirred for 2.5 h at −78° C. and then sat. aq. NH₄Cl was added and the phases were separated. The aqueous phase was extracted with ethyl acetate (3×) and the combined organics were washed with water, brine, dried (MgSO₄) and concentrated. Flash chromatography of the residue (silica gel; hexane/ethyl acetate 4:1 to 7:3) provided the 2-[(1-Hydroxy)cyclohexyl]thiazole compound (5.8 g).

Step 2: 2-{1-[(2-Trimethylsilylethoxy)methoxy] cyclohexyl}thiazole

To a solution of the alcohol 2-[(1-Hydroxy)cyclohexyl] thiazole from Step 1 (5.8 g, 32 mmol) and Hunig's base (14 mL, 67 mmol) in dichloromethane (100 mL) at 0° C. was added 2-(trimethylsilyl)ethoxymethyl chloride (6.5 mL, 36.7 mmol). The resulting solution was stirred at 0° C. for 15 min, was heated at reflux temperature for 15 h and then cooled to room temperature. Sat. aq. NH₄Cl was added and the resulting mixture was extracted with dichloromethane (3×). The combined organics were washed with water, brine, dried (MgSO₄) and concentrated. Flash chromatography of the residue (silica gel; hexane/ethyl acetate 7:3) provided 2-{1-[(2-Trimethylsilylethoxy)methoxy] cyclohexyl}thiazole (8 g).

Aldehyde 1

3-cyclproplyoxy-4-difluoromethoxybenzaldehyde

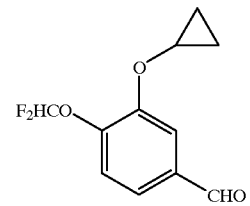

Step 1: 3-(2-Chloro)ethoxy-4-difluoromethoxybenzaldehyde

A mixture of 3-hydroxy-4-difluoromethoxybenzaldehyde (77 g, 409 mmol), 1-bromo-2-chloroethane (176 g, 1.23 mol) and Cs₂CO₃ (146 g, 449 mmol) in DMF (2 L) was stirred at 70° C. for 3 h and at 55° C. for 15 h. The mixture was cooled to room temperature and partitioned between ethyl acetate (1 L) and water (2 L). The aqueous layer was extracted with ethyl acetate (2×) and the combined organics were washed with water, dried (Na₂SO₄) and concentrated. Flash chromatography of the residue (silica gel; hexane/ethyl acetate 4:1 to 7:3) provided the 3-(2-Chloro)ethoxy-4-difluoromethoxybenzaldehyde compound (87 g).

Step 2: 3-(2-Chloro)ethoxy-4-difluoromethoxy-1-(triisopropylsilyloxy)methylbenzene To a solution of the aldehyde 3-(2-Chloro)ethoxy-4-difluoromethoxybenzaldehyde from Step 1 (87 g, 347 mmol) in THF (1 L) and MeOH (200 mL) at 0° C. was added NaBH₄ (15.7 g, 416 mmol) in 4 portions over 20 min. The resulting mixture was stirred at room temperature for 3 h, re-cooled to 0° C., and then sat. aq. NH₄Cl (50 mL) was carefully added over 10 min. The mixture was diluted with ethyl acetate (500 mL). The mixture was partioned between 25% aq. NH₄OAc (1 L) and ethyl acetate (1 L) and the aqueous layer was extracted with ethyl acetate (2×). The combined organics were washed with brine, dried (Na₂SO₄) and concentrated.

The residue was dissolved in dichloromethane (1 L) and 2,6-lutidine (60 mL, 520 mmol) and cooled in an ice bath. Triisopropylsilyl triflate (102 mL, 381 mmol) was slowly added and after addition was complete, the mixture was stirred at room temperature for 2 h. A second aliquot of triisopropylsilyl triflate (16 mL) was added and the mixture was stirred for 15 h. The mixture was cooled to 0° C. and sat. aq. NaHCO₃ (50 mL) was added. Ether (1.5 L) and 25% aq. NH₄OAc (1 L) were added and the aqueous layer was extracted with ether (2×). The combined organics were washed with brine, dried (Na₂SO₄) and concentrated. Flash chromatography of the residue (silica gel; hexane/ethyl acetate 98:2 to 95:5) provided the 3-(2-Chloro)ethoxy-4-difluoromethoxy-1-(triisopropylsilyloxy)methylbenzene compound (124 g).

Step 3: 3-Ethenyloxy-4-difluoromethoxy-1-(triisopropylsilyloxy)methylbenzene

A mixture of the chloride, 3-(2-Chloro)ethoxy-4-difluoromethoxy-1-(triisopropylsilyloxy)methylbenzene, from Step 2 (124 g, 303 mmol), 10N NaOH (300 mL, 3.03 mol) and Bu$_4$NHSO$_4$ (102 g, 303 mmol) in benzene (1.3 L) was heated at 65° C. for 4.5 h. The mixture was cooled to room temperature and was partitioned with 25% aq. NH$_4$OAc (500 mL). The aqueous phase was extracted with ether (2×) and the combined organics were washed with brine, dried (Na$_2$SO$_4$) and concentrated. The residual oil was dissolved in dichloromethane (1 L) and 2,6-lutidine (53 mL, 454 mmol) and cooled in an ice bath. Triisopropylsilyl triflate (98 mL, 363 mmol) was slowly added and after addition was complete, the mixture was stirred at room temperature for 3 h. The mixture was cooled to 0° C. and sat. aq. NaHCO$_3$ (50 mL) was added. Ether (1.5L) and 25% aq. NH$_4$OAc (500 mL) were added and the aqueous layer was extracted with ether (2×). The combined organics were washed with brine, dried (Na$_2$SO$_4$) and concentrated. Flash chromatography of the residue (silica gel; hexane/ethyl acetate 98:2 to 95:5) provided 3-Ethenyloxy-4-difluoromethoxy-1-(triisopropylsilyloxy)methylbenzene (67 g).

Step 4: 3-Cyclopropyloxy-4-difluoromethoxy-1-(triisopropylsilyloxy)methylbenzene To a solution of the alkene, 3-Ethenyloxy-4-difluoromethoxy-1-(triisopropylsilyloxy)methylbenzene, from Step 3 (67 g, 179 mmol) and chloroiodomethane (78 mL, 1.07 mol) in dichloromethane (1.5 L) at 5° C. (ice bath) was added diethyl zinc (55 mL, 537 mmol) in 5 mL portions over 1.2 h. During the addition, the internal temperature was maintained at <20° C. After the addition was complete, the mixture was stirred for 15 min and then the cooling bath was removed and stirring was continued for a further 2.5 h. The mixture was re-cooled to 5° C. (ice bath) and MeOH (2 mL) was added over 15 min, followed by the addition of water (30 mL) over 15 min and finally, the addition of 6N HCl (5 mL). The mixture was partitioned between ether (1 L) and water (500 mL). The aqueous layer was extracted with ether (500 mL) and the combined organics were washed with brine, dried (Na$_2$SO$_4$) and concentrated. Flash chromatography of the residue (silica gel; hexane/ethyl acetate 98:2 to 95:5) provided 3-Cyclopropyloxy-4-difluoromethoxy-1-(triisopropylsilyloxy)methylbenzene (71 g).

Step 5: 3-Cyclopropyloxy-4-difluoromethoxybenzyl alcohol

To a solution of the silyl ether, 3-Cyclopropyloxy-4-difluoromethoxy-1-(triisopropylsilyloxy)methylbenzene, from Step 4 (70 g, 179 mmol) in THF (700 mL) at room temperature was added TBAF (215 mL of a 1M solution in THF, 215 mmol) and the resulting mixture was stirred for 17 h. The mixture was partitioned between 25% aq. NH$_4$OAc (500 mL) and ethyl acetate (1 L) and the aqueous layer was extracted with ethyl acetate (2×). The combined organics were washed with brine, dried (Na$_2$SO$_4$) and concentrated. Flash chromatography of the residue (silica gel; hexane/ethyl acetate 3:2 to 1:1) provided the 3-Cyclopropyloxy-4-difluoromethoxybenzyl alcohol compound (41 g).

Step 6: 3-Cyclopropyloxy-4-difluoromethoxybenzaldehyde

To a solution of the 3-Cyclopropyloxy-4-difluoromethoxybenzyl alcohol from Step 5 (41 g, 179 mmol) in dichloromethane (1.2 L) was added MnO$_2$ (220 g, 2.15 mol) in four portions over 2 days. When TLC indicated the reaction was complete, the mixture was diluted with ethyl acetate and filtered through Celite® (available from Aldrich Chemical Company, Inc., Milwaukee, Wis.), washing extensively with a succession of ethyl acetate, dichloromethane, EtOH and toluene. The combined filtrates were concentrated. Flash chromatography of the residue (silica gel; hexane/ethyl acetate 3:1 to 7:3) provided the 3-Cyclopropyloxy-4-difluoromethoxybenzaldehyde compound (31 g).

Example 1

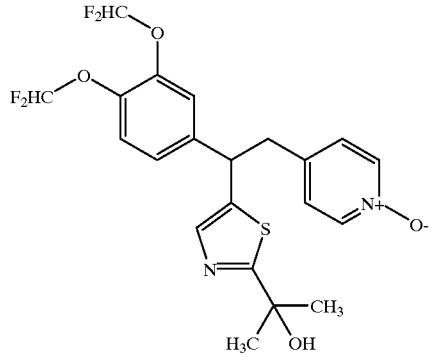

(±)-4-{2-[3,4-Bis(difluoromethoxy)phenyl]-2-{5-[2-(1-hydroxy-1-methyl)ethyl]thiazolyl}ethyl}pyridine N-oxide Example 1 was prepared by the following procedure:

Step 1: (±)-3,4-Bis(difluoromethoxy)phenyl-5-{2-(1-methyl-1-[(2-trimethylsilylethoxy)methoxy]ethyl}thiazolylcarbinol To a solution of n-BuLi (5.6 mL of a 2.5M solution in hexane, 14 mmol) in anhydrous ether (50 mL) at −78° C. was added a solution of Thiazole 1 (3.8 g, 14 mmol) in anhydrous ether (30 mL). After 70 min, a solution of 3,4-bis(difluoromethoxy)benzaldehyde (2.8 g, 11.7 mmol) in anhydrous ether (20 mL) was added. The resulting mixture was stirred at −78° C. for 2.5 h and then sat. aq. NH$_4$Cl was added. The mixture was allowed to warm to room temperature and then partitioned with ethyl acetate and water. The aqueous phase was extracted with ethyl acetate (3×) and the combined organics were washed with water, brine, dried (MgSO$_4$) and concentrated. Flash chromatography of the residue (silica gel; hexane/ethyl acetate 4:1 to 7:3) provided the (±)-3,4-Bis(difluoromethoxy)phenyl-5-{2-(1-methyl-1-[(2-trimethylsilylethoxy)methoxy]ethyl}thiazolylcarbinol product (3.85 g).

Step 2: (±)-4-{2-[3,4-Bis(difluoromethoxy)phenyl]-2-[5-(2-(1-methyl-1-[(2-trimethylsilylethoxy)methoxy]ethyl)thiazolyl]ethyl}pyridine To a solution of Hunig's base (1.7 mL, 9.8 mmol) in toluene (8 mL) at 0° C. was slowly added thionyl chloride (0.35 mL, 4.8 mmol) and the resulting mixture was stirred at this temperature for 5 min. To this mixture was slowly added a solution of (±)-3,4-bis(difluoromethoxy)phenyl-5-{2-(1-methyl-1-[(2-trimethylsilylethoxy)methoxy]ethyl}thiazolylcarbinol from Step 1 (1.6 g, 3.2 mmol) in toluene (10 mL). The mixture was stirred at 0° C. for 45 min and then mixture was filtered through a pad of silica gel pre-wetted with ether, eluting with ether/hexane (4:1). The filtrate was concentrated to provide the crude chloride that was used immediately.

To a solution of ethyl 4-pyridylacetate (2.12 g, 12.8 mmol) in THF (20 mL) and HMPA (2.2 mL, 12.6 mmol) at room temperature was added sodium bis(trimethylsilyl)amide (12.7 mL of a 1M solution in THF, 12.7 mmol). The resulting mixture was stirred for 30 min and then a THF (10 mL) solution of the crude chloride prepared above was added and then stirred for 15 h at 25° C. Sat. aq. NH$_4$Cl was added, the layers were separated and the aqueous phase was extracted with ethyl acetate (3×). The combined organics were washed successively with water (3×), brine, dried (MgSO$_4$) and concentrated to give a thick oil.

This material was dissolved in a mixture of THF/MeOH/water (2:2:1, 20 mL), LiOH (1.5 g) was added and the mixture was heated at reflux for 1.5 h. 1N HCl was slowly added, bringing the pH to approximately 6. The mixture was extracted three times with ethyl acetate and the combined organics were washed with water, brine, dried (MgSO$_4$) and concentrated. Flash chromatography of the residue (silica gel; ethyl acetate/hexane 4:1) provided the (±)-4-{2-[3,4-Bis(difluoromethoxy)phenyl]-2-[5-(2-(1-methyl-1-[(2-trimethylsilylethoxy)methoxy]ethyl)thiazolyl]ethyl}pyridine product as an oil (745 mg).

Step 3: (±)-4-{2-[3,4-Bis(difluoromethoxy)phenyl]-2-[5-(2-(1-hydroxy-1-methyl)ethyl)thiazolyl]ethyl}pyridine To a solution of the protected alcohol from Step 2 (722 mg, 1.23 mmol) in dichloromethane (20 mL) was added TFA (3.8 mL, 49.3 mmol) and the mixture was stirred at 0° C. for 2.5 h. Sat. aq. NH$_4$OAc was added and the mixture was extracted with ethyl acetate (3×). The combined organics were washed with water, brine, dried (MgSO$_4$) and concentrated. Flash chromatography of the residue (silica gel; ethyl acetate) provided the (±)-4-{2-[3,4-Bis(difluoromethoxy)phenyl]-2-[5-(2-(1-hydroxy-1-methyl)ethyl)thiazolyl]ethyl}pyridine as an oil (394 mg).

Step 4: (±)-4-{2-[3,4-Bis(difluoromethoxy)phenyl]-2-[5-(2-(1-hydroxy-1-methyl)ethyl)thiazolyl]ethyl}pyridine N-oxide A mixture of the pyridine from Step 3 (192 mg, 0.42 mmol) and MMPP (209 mg, 0.42 mmol) in dichloromethane (12 mL) and MeOH (1 mL) was stirred at room temperature for 22 h. The mixture was filtered through Celite® and the filtrate was concentrated. Chromatography of the residue (silica gel; dichloromethane/EtOH 4:1) provided the title (±)-4-{2-[3,4-Bis(difluoromethoxy)phenyl]-2-[5-(2-(1-hydroxy-1-methyl)ethyl)thiazolyl]ethyl}pyridine N-oxide compound as a colorless foam (112 mg).

$^1$HNMR (400 MHz, acetone-d$_6$): δ1.51 (s, 6H), 3.45 (m, 2H), 4.75 (t, 1H), 4.95 (br s, 1H), 6.95 (t, 1H), 6.96 (t, 1H), 7.19 (d, 2H), 7.30 (dd, 2H), 7.38 (s, 1H), 7.48 (s, 1H), 7.94 (d, 2H).

Example 2

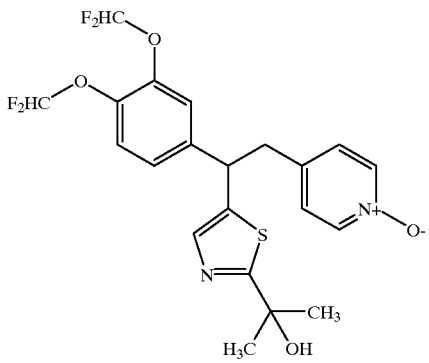

Chiral 4-{2-[3,4-Bis(difluoromethoxy)phenyl]-2-{5-[2-(1-hydroxy-1-methyl)ethyl]thiazole}ethyl}pyridine N-oxide Example 2 was prepared by the following procedure:

Step 1: (±)-4-{2-[3,4-Bis(difluoromethoxy)phenyl]-2-[5-(2-(1-hydroxy)ethyl)thiazolyl]ethyl}pyridine To a solution of Intermediate 1 (5.87 g, 13.8 mmol) in dichloromethane (170 mL) at 0° C. was added MeMgCl (20 mL of a 3M solution in THF, 60 mmol) in three portions over 1 h. After a further 20 min, sat. aq. NH$_4$Cl was added and the mixture was extracted with ethyl acetate (3×). The combined organics were washed with water, brine, dried (MgSO$_4$) and concentrated. Flash chromatography of the residue (silica gel; acetone/dichloromethane 3:2) provided (±)-4-{2-[3,4-Bis(difluoromethoxy)phenyl]-2-[5-(2-(1-hydroxy)ethyl)thiazolyl]ethyl}pyridine as an oil (5.11 g).

Step 2: (±)-4-{2-[3,4-Bis(difluoromethoxy)phenyl]-2-[5-(2-acetyl)thiazolyl]ethyl}pyridine A mixture of the alcohol, (±)-4-{2-[3,4-Bis(difluoromethoxy)phenyl]-2-[5-(2-(1-hydroxy)ethyl)thiazolyl]ethyl}pyridine, from Step 1 (5.07 g, 11.5 mmol) and MnO$_2$ (11 g, 126.5 mmol) in dichloromethane (100 mL) was stirred at room temperature for 48 h. The mixture was filtered through Celite®, washing with dichloromethane, and the filtrate was concentrated. Flash chromatography of the residue (silica gel; acetone/dichloromethane 1:3) provided (±)-4-{2-[3,4-Bis(difluoromethoxy)phenyl]-2-[5-(2-acetyl)thiazolyl]ethyl}pyridine as an oil (4.87 g).

Step 3: Resolution of (±)-4-{2-[3,4-Bis(difluoromethoxy)phenyl]-2-[5-(2-acetyl)thiazolyl]ethyl}pyridine A solution of (±)-4-{2-[3,4-bis(difluoromethoxy)phenyl]-2-[5-(2-acetyl)thiazolyl]ethyl}pyridine (Step 2; 4.87 g) in EtOE/hexane (21 mL, 2:3) was injected (3×7 mL). onto a Chiralpak® AD (available from Chiral Technologies, Inc., Exton, Pa.) preparative (5cm×50 cm) HPLC column (eluting with hexane/ethanol 3:1 at 55 mL/min with UV detection at 270 nm). The enantiomers were separated with the faster eluting enantiomer having a retention time of ~38 min (Enantiomer 1) and the slower eluting enantiomer (Enantiomer 2) having a retention time of ~66 min. The eluants were concentrated to provide the enantiomers as brown gums: Enantiomer 1 (2.2 g) and Enantiomer 2 (2.3 g).

Step 4: Chiral 4-{2-[3,4-Bis(difluoromethoxy)phenyl]-2-[5-(2-(1-hydroxy-1-methyl)ethyl)thiazolyl]ethyl}pyridine A mixture of CeCl$_3$ (288 mg, 1.17 mmol; dried at 140° C. for 15 h) in THF (12 mL) was heated at reflux for 3 h and then cooled to 0° C. MeMgCl (1.7 mL of a 3M solution in THF, 5.1 mmol) was added and the mixture was stirred for 2 h. A solution of Enantiomer 2 (Step 3, 400 mg, 0.91 mmol) in toluene (4 mL) was added dropwise and the mixture was stirred for 1 h. Sat. aq. NH₄Cl was added and the mixture was extracted with ethyl acetate (3×). The combined organics were washed with water, brine, dried (MgSO₄) and concentrated. Flash chromatography of the residue (silica gel; acetone/dichloromethane 1:1) provided the Chiral 4-{2-[3,4-Bis(difluoromethoxy)phenyl]-2-[5-(2-(1-hydroxy-1-methyl)ethyl)thiazolyl]ethyl}pyridine product as an oil (383 mg).

Step 5: Chiral 4-{2-[3,4-Bis(difluoromethoxy) phenyl]-2-[5-(2-(1-hydroxy-1-methyl)ethyl) thiazolyl]ethyl}pyridine N-oxide A mixture of the pyridine from Step 4 (383 mg, 0.84 mmol) and MMPP (415 mg, 0.89 mmol) in dichloromethane (25 mL) and MeOH (25 mL) was stirred at room temperature for 48 h. The mixture was filtered through Celite® and the filtrate was washed with sat. aq. NaHCO₃, water, brine, dried (MgSO₄) and concentrated. Chromatography of the residue (silica gel; ethyl acetate/EtOH 65:35) provided the title Chiral 4-{2-[3,4-Bis(difluoromethoxy)phenyl]-2-[5-(2-(1-hydroxy-1-methyl)ethyl)thiazolyl]ethyl}pyridine compound as a colorless foam (306 mg).

¹HNMR (400 MHz, acetone-d₆): δ1.51 (s, 6H), 3.45 (m, 2H), 4.75 (t, 1H), 4.95 (br s, 1H), 6.95 (t, 1H), 6.96 (t, 1H), 7.19 (d, 2H), 7.30 (dd, 2H), 7.38 (s, 1H), 7.48 (s, 1H), 7.94 (d, 2H).

Example 3

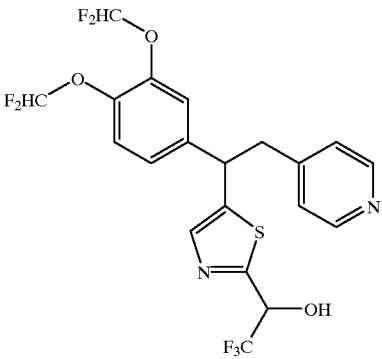

(±/±)-4-{2-[3,4-Bis(difluoromethoxy)phenyl]-2-[5-(2-(1-hydroxy-2,2,2-trifluoro)ethyl)thiazolyl] ethyl}pyridine Example 3 was prepared by the following procedure. To a mixture of Intermediate 1 (1.24 g, 2.9 mmol) and trimethyl (trifluoromethyl)silane (0.9 mL, 6.5 mmol) in THF (15 mL) at 0° C. was added TBAF (0.13 mL of a 1M solution in THF, 0.13 mmol). After 1 h, 1M HCl (10 mL) was added and the mixture was stirred for 1.5 h at room temperature. The mixture was basified with sat. aq. Na₂CO₃ and then extracted with ethyl acetate (3×). The combined organics were dried (MgSO₄) and concentrated. Chromatography of the residue (silica gel; acetone/toluene 3:7 to 1:1) provided the title compound as a colorless foam (892 mg).

¹HNMR (400 MHz, acetone-d₆): δ3.51 (m, 2H), 4.90 (t, 1H), 5.43 (m, 1H), 6.64 (br s, 1H), 6.94 (t, 1H), 6.95 (t, 1H), 7.12–7.41 (m, 5H), 7.66 (d, 1H), 8.38 (m, 2H).

Example 4

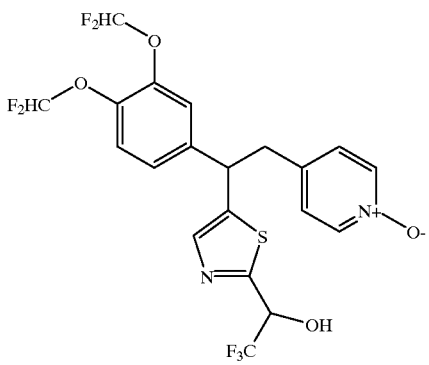

(±/±)-4-{2-[3,4-Bis(difluoromethoxy)phenyl]-2-[5-(2-(1-hydroxy-2,2,2-trifluoro)ethyl)thiazolyl] ethyl}pyridine N-oxide Example 4 was prepared by the following procedure. A mixture of the pyridine from Example 3 (166 mg, 0.34 mmol) and MMPP (99 mg, 0.35 mmol) in dichloromethane (12 mL) and MeOH (3 mL) was stirred at room temperature for 48 h. An additional 25 mg of MMPP was added and the mixture was heated at reflux temperature for 5 h. The mixture was filtered through Celite®, 1N NaOH was added and the mixture was extracted with ethyl acetate (3×). The combined organics were dried (MgSO₄) and concentrated. Chromatography of the residue (silica gel; dichloromethane/MeOH 9:1) provided the title compound as a colorless foam (106 mg).

¹HNMR (400 MHz, acetone-d₆): δ3.51 (m, 2H), 4.87 (t, 1H), 5.43 (m, 1H), 6.89 (br s, 1H), 6.96 (t, 2H), 7.22 (d, 2H), 7.33 (m, 2H), 7.41 (d, 1H), 7.68 (m, 1H), 7.96 (d, 2H).

Example 5

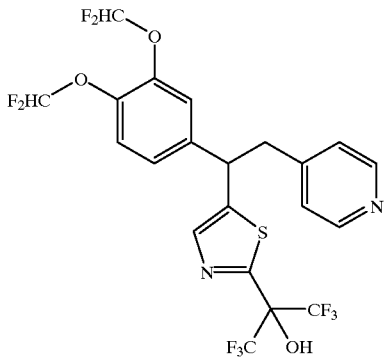

(±)-4-{2-[3,4-Bis(difluoromethoxy)phenyl]-2-{5-[2-(1-hydroxy-1-trifluoromethyl-2,2,2-trifluoro)ethyl] thiazolyl}ethyl}pyridine Example 5 was prepared by following the procedures described in Example 1, Steps 1 to 3, but substituting Thiazole 2 for Thiazole 1. Flash chromatography silica gel; toluene/acetone 7:3 to 3:2 provided the title product as a foam (208 mg).

¹HNMR (400 MHz, acetone-d6): δ3.55 (m, 2H), 4.96 (t, 1H), 6.94 (t, 1H), 6.96 (t, 1H), 7.20 (d, 2H), 7.30 (d, 1H), 7.36 (d, 1H), 7.42 (s, 1H), 7.81 (s, 1H), 8.20 (br s, 1H), 8.38 (d, 2H).

Example 6

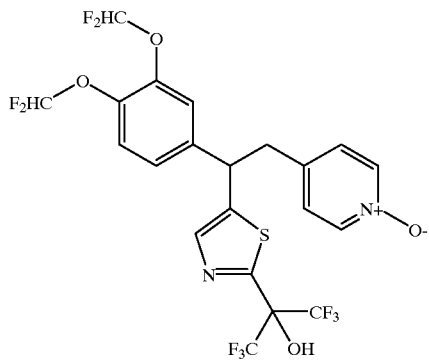

(±)-4-{2-[3,4-Bis(difluoromethoxy)phenyl]-2-{5-[2-(1-hydroxy-1-trifluoromethyl-2,2,2-trifluoro)ethyl]thiazolyl}ethyl}pyridine N-oxide Example 6 was prepared by following the procedures described in Example 1, Step 4, but substituting Example 5 for the pyridine from Example 1, Step 3. The title compound (flash chromatography silica gel; dichloromethane/MeOH 9:1) was obtained as a foam (100 mg).

$^1$HNMR (400 MHz, acetone-$d_6$): δ3.55 (m, 2H), 4.91 (t, 1H), 6.95 (t, 2H), 7.22 (d, 2H), 7.32 (d, 1H), 7.37 (d, 1H), 7.42 (s, 1H), 7.80 (s, 1H), 7.96 (d, 2H), 8.50(br s, 1H).

Example 7

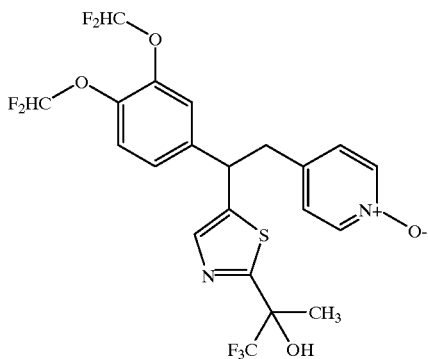

(±/±)-4-{2-[3,4-Bis(difluoromethoxy)phenyl]-2-{5-[2-(1-hydroxy-1-trifluoromethyl)ethyl]thiazolyl}ethyl}pyridine N-oxide Example 7 was prepared by the following procedure:

Step 1: (±/±)-3,4-Bis(difluoromethoxy)phenyl-5-{2-(1-trifluoromethyl-1-[(2-trimethylsilylethoxy)methoxy]ethyl}thiazolylcarbinol To a solution of Thiazole 3 (3.4 g, 10.4 mmol) in anhydrous THF (30 mL) at −78° C. was added n-BuLi (8.7 mL of a 1.2M solution in hexane, 10.4 mmol) over 10 min. After 30 min, a solution of 3,4-bis(difluoromethoxy)benzaldehyde (2.7 g, 10.4 mmol) in anhydrous THF (30 mL) was added via cannula. The mixture was stirred at −78° C. for 1 h, the cooling bath was removed and then, after 15 min, sat. aq. NH$_4$Cl was added. The mixture was partitioned with ethyl acetate and water. The aqueous phase was extracted with ethyl acetate (3×) and the combined organics were washed with brine, dried (Na$_2$SO$_4$) and concentrated. Flash chromatography of the residue (silica gel; hexane/ethyl acetate 7:3 to 3:2) provided (±/±)-3,4-Bis(difluoromethoxy)phenyl-5-{2-(1-trifluoromethyl-1-[(2-trimethylsilylethoxy)methoxy]ethyl}thiazolylcarbinol (5.66 g).

Step 2: (±/±)-4-{2-[3,4-Bis(difluoromethoxy)phenyl]-2-[5-(2-(1-trifluoromethyl-1-[(2-trimethylsilylethoxy)methoxy]ethyl)thiazolyl]ethyl}pyridine To a solution of pyridine (1.6 mL, 19.8 mmol) in toluene (50 mL) at 0° C. was slowly added thionyl bromide (1 mL, 12.9 mmol) and the resulting mixture was stirred at this temperature for 5 min. To this mixture was slowly added a solution of the alcohol, (±/±)-3,4-Bis(difluoromethoxy)phenyl-5-{2-(1-trifluoromethyl-1-[(2-trimethylsilylethoxy)methoxy]ethyl}thiazolylcarbinol, from Step 1 (5.6 g, 9.9 mmol) in toluene (50 mL). The mixture was stirred at room temperature for 1 h and then concentrated to provide the crude bromide that was used immediately.

To a solution of ethyl 4-pyridylacetate (6.5 g, 39.6 mmol) in TF (200 mL) and HMPA (6.8 mL, 39.6 mmol) at room temperature was added potassium bis(trimethylsilyl)amide (79 mL of a 0.5M solution in toluene, 39.6 mmol). The resulting mixture was stirred for 30 min and then a THF (50 mL) solution of the crude bromide prepared above was added and then stirred for 2 h at 25° C. 25% aq. NH$_4$OAc and ethyl acetate were added, the layers. were separated and the aqueous phase was extracted with ethyl acetate. The combined organics were washed with brine, dried (Na$_2$SO$_4$) and concentrated to give a thick oil. This material was dissolved in a mixture of THF/MeOH/water (3:1:1, 300 mL), 2N NaOH (60 mL) was added and the mixture was heated at 65° C. for 3 h. After cooling to room temperature, 6N HCl was slowly added, bringing the pH to approximately 6. The mixture was concentrated and partitioned with ethyl acetate and 25% aq. NH$_4$OAc. The aqueous phase was extracted with ethyl acetate and the combined organics were washed with brine, dried (Na$_2$SO$_4$) and concentrated. Flash chromatography of the residue (silica gel; ethyl acetate/hexane 3:2 to 4:1) provided (±/±)-4-{2-[3,4-Bis(difluoromethoxy)phenyl]-2-[5-(2-(1-trifluoromethyl-1-[(2-trimethylsilylethoxy)methoxy]ethyl)thiazolyl]ethyl}pyridine as an oil (4 g).

Step 3: (±/±)-4-{2-[3,4-Bis(difluoromethoxy)phenyl]-2-[5-(2-(1-hydroxy-1-trifluoromethyl)ethyl)thiazolyl]ethyl}pyridine To a solution of the protected alcohol, (±/±)-4-{2-[3,4-Bis(difluoromethoxy)phenyl]-2-[5-(2-(1-trifluoromethyl-1-[(2-trimethylsilylethoxy)methoxy]ethyl)thiazolyl]ethyl}pyridine, from Step 2 (200 mg, 0.31 mmol) in dichloromethane (3 mL) was added TFA (trifluoroacetic acid) (0.5 mL) and the mixture was stirred at room temperature for 15 min. The mixture was concentrated and then partitioned with sat. aq. NH$_4$OAc and ethyl acetate. The aqueous phase was extracted with ethyl acetate and the combined organics were washed with brine, dried (Na$_2$SO$_4$) and concentrated. Flash chromatography of the residue (silica gel; dichloromethane/EtOH 9:1) provided (±/±)-4-{2-[3,4-Bis(difluoromethoxy)phenyl]-2-[5-(2-(1-hydroxy-1-trifluoromethyl)ethyl)thiazolyl]ethyl}pyridine as an oil (115 mg).

Step 4: (±/±)-4-{2-[3,4-Bis(difluoromethoxy)phenyl]-2-[5-(2-(1-hydroxy-1-trifluoromethyl)ethyl)thiazolyl]ethyl}pyridine N-oxide A mixture of the (±/±)-4-{2-[3,4-Bis(difluoromethoxy)phenyl]-2-[5-(2-(1-hydroxy-1-trifluoromethyl)ethyl)

thiazolyl]ethyl}pyridine from Step 3 (115 mg, 0.23 mmol) and MMPP (222 mg, 0.45 mmol) in dichloromethane (5 mL) and MeOH (0.5 mL) was heated at 50° C. for 30 min and then additional MMPP (0.5 eq) and MeOH (0.25 mL) was added. The mixture was stirred at 50° C. for 30 min and then at room temperature for 15 h. The mixture was concentrated. Flash chromatography of the residue (silica gel; dichloromethane/MeOH/10% NH$_4$OH 8:1:1) provided the title compound as a colorless foam (117 mg).

$^1$HNMR (500 MHz, acetone-d$_6$): δ1.78 (s, 3H), 3.50 (m, 2H), 4.84 (m, 1H), 6.5 (d, 1H), 6.95 (t, 1H), 6.96 (t, 1H), 7.21 (d, 2H), 7.33 (m, 2H), 7.40 (d, 1H), 7.66 (d, 1H), 7.95 (d, 2H).

Example 8

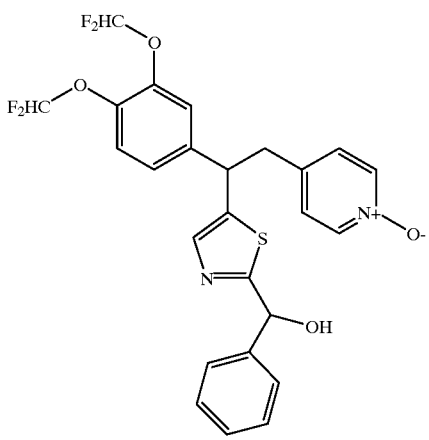

(±/±)-4-{2-[3,4-Bis(difluoromethoxy)phenyl]-2-[5-(2-phenylmethanol)thiazolyl]ethyl}pyridine N-oxide Example 8 was prepared by the following procedure:

Step 1: (±/±)-4-{2-[3,4-Bis(difluoromethoxy) phenyl]-2-[5-(2-phenylmethanol)thiazolyl] ethyl}pyridine To a solution of Intermediate 1 (1.48 g, 3.5 mmol) in dichloromethane (38 mL) at 0° C. was added dropwise PhMgCl (5.2 mL of a 2M solution in THF, 10.4 mmol). After 30 min, a second aliquot of PhMgCl (2 mL) was added. After a further 30 min, sat. aq. NH$_4$Cl was added and the mixture was extracted with ethyl acetate (3×). The combined organics were washed with water, brine, dried (MgSO$_4$) and concentrated. Chromatography of the residue (silica gel; dichloromethane/acetone 7:3 to 3:2) provided (±/±)-4-{2-[3,4-Bis(difluoromethoxy)phenyl]-2-[5-(2-phenylmethanol) thiazolyl]ethyl}pyridine as a colorless oil (1.32 g).

Step 2: (±/±)-4-{2-[3,4-Bis(difluoromethoxy) phenyl]-2-[5-(2-phenylmethanol)thiazolyl] ethyl}pyridine N-oxide Following the procedures described in Example 1, Step 4, but substituting the (±/±)-4-{2-[3,4-Bis(difluoromethoxy) phenyl]-2-[5-(2-phenylmethanol)thiazolyl]ethyl}pyridine from Step 1 (65 mg, 0.13 mmol) for the pyridine from Example 1, Step 3, the (±/±)-4-[2-[3,4-Bis(difluoromethoxy)phenyl]-2-{5-(2-phenylmethanol) thiazolyl]ethyl}pyridine N-oxide title compound (chromatography silica gel; dichloromethane/EtOH 7:3) was obtained as an oil (33 mg).

$^1$HNMR (500 MHz, acetone-d$_6$): δ3.43 (m, 2H), 4.76 (m, 1H), 5.71 (br s, 1H), 5.95 (s, 1H), 6.94 (t, 2H), 7.17 (br s, 2H), 7.24–7.49 (m, 4H), 7.93 (m, 2H).

Example 9

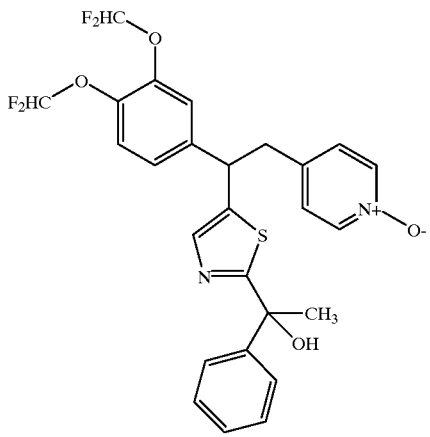

(±/±)-4-{2-[3,4-Bis(difluoromethoxy)phenyl]-2-[5-(2-(1-hydroxy-1-phenyl)ethyl)thiazolyl] ethyl}pyridine N-oxide Example 9 was prepared by the following procedure:

Step 1: (±)-4-{2-[3,4-Bis(difluoromethoxy)phenyl]-2-[5-(2-benzoyl)thiazolyl]ethyl}pyridine To a solution of oxalyl chloride (0.45 mL, 5.2 mmol) in dichloromethane (20 mL) at −78° C. was added DMSO (0.74 mL, 10 mmol). After 5 min, a solution of the alcohol (1.30 g, 2.58 mmol) from Step 1 of Example 8 in dichloromethane (20 mL) was added and the mixture was stirred for 2 h. Triethylamine (3 mL, 22 mmol) was added and after 1.5 h, the mixture was warmed to room temperature. Water was added and the mixture was extracted with ethyl acetate (3×). The combined organics were washed with water, brine, dried (MgSO$_4$) and concentrated. Flash chromatography of the residue (silica gel; hexane/ethyl acetate 35:65 to 3:7) provided (±)-4-{2-[3,4-Bis(difluoromethoxy)phenyl]-2-[5-(2-benzoyl)thiazolyl]ethyl}pyridine as a colorless oil (869 mg).

Step 2: (±/±)-4-{2-[3,4-Bis(difluoromethoxy) phenyl]-2-[5-(2-(1-hydroxy-1-phenyl)ethyl) thiazolyl]ethyl}pyridine To a solution of the ketone, (±)-4-{2-[3,4-Bis (difluoromethoxy)phenyl]-2-[5-(2-benzoyl)thiazolyl] ethyl}pyridine, from the present Step 1 (413 mg, 0.82 mmol) in dichloromethane (20 mL) at −78° C., was added dropwise MeMgBr (0.8 mL of a 3M solution in ether, 2.4 mmol). After 15 min, a second aliquot of MeMgBr (0.2 mL) was added. After a further 30 min, 25% aq. NH$_4$OAc was added and the mixture was extracted with dichloromethane (3×). The combined organics were washed with brine, dried (MgSO$_4$) and concentrated. Flash chromatography of the residue (silica gel; ethyl acetate/hexane 9:1 to 1:0) provided (±/±)-4-{2-[3,4-Bis(difluoromethoxy)phenyl]-2-[5-)2-(1-hydroxy-1-phenyl)ethyl)thiazolyl]ethyl}pyridine as a colorless oil (332 mg).

Step 3: (±/±)-4-{2-[3,4-Bis(difluoromethoxy)phenyl]-2-[5-(2-(1-hydroxy-1-phenyl)ethyl)thiazolyl]ethyl}pyridine N-oxide Following the procedures described in Example 1, Step 4, but substituting the (±/±)-4-{2-[3,4-Bis(difluoromethoxy)phenyl]-2-[5-(2-(1-hydroxy-1-phenyl)ethyl)thiazolyl]ethyl}pyridine from Step 2 (293 mg, 0.57 mmol) for the pyridine from Example 1, Step 3, the title (±/±)-4-{2-[3,4-Bis(difluoromethoxy)phenyl]-2-[5-(2-(1-hydroxy-1-phenyl)ethyl)thiazolyl]ethyl}pyridine N-oxide compound (chromatography silica gel; dichloromethane/MeOH 9:1) was obtained as a white foam (163 mg).

$^1$HNMR (400 MHz, acetone-$d_6$): δ1.92 and 1.93 (s each, 3H), 3.42 (m, 2H), 4.72 (m, 1H), 5.70 (br s, 1H), 6.94 (app t, 2H), 7.11–7.37 (m, 8H), 7.49 (d, 1H), 7.57 (m, 2H), 7.92 (m, 2H).

Example 10

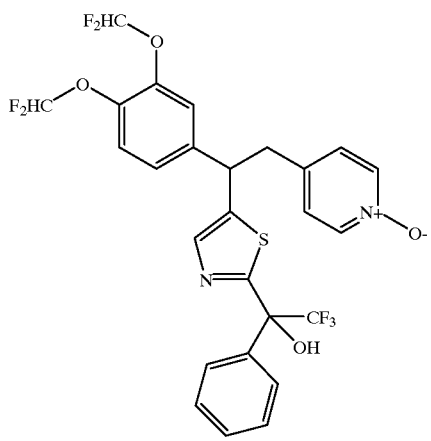

(±/±)-4-{2-[3,4-Bis(difluoromethoxy)phenyl]-2-[5-(2-(1-hydroxy-1-phenyl-2,2,2-trifluoro)ethyl)thiazolyl]ethyl}pyridine N-oxide Example 10 was prepared by following the procedures described in Examples 3 and 4, but substituting the ketone from Example 9, Step 1 (450 mg, 1.06 mmol) for Intermediate 1. The title compound was obtained (chromatography silica gel; dichloromethane/MeOH 9:1) as a yellow foam (80 mg).

$^1$HNMR (400 MHz, acetone-$d_6$): δ3.49 (m, 2H), 4.83 (m, 1H), 6.94 (app t, 2H), 7.17–7.35 (m, 4H), 7.40 (m, 4H), 7.69–7.78 (m, 3H), 7.92 (d, 2H).

Example 11

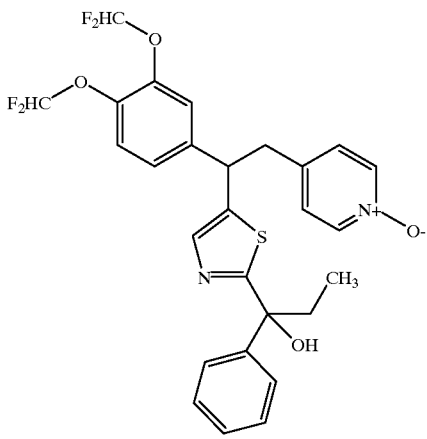

(±/±)-4-{2-[3,4-Bis(difluoromethoxy)phenyl]-2-[5-(2-(1-hydroxy-1-phenyl)propyl)thiazolyl]ethyl}pyridine N-oxide Example 11 was prepared by following the procedures described in Example 9, Steps 2 and 3, but substituting EtMgBr (1M in THF) for MeMgBr. The title compound was obtained (chromatography silica gel; dichloromethane/MeOH 9:1) as a foam (80 mg).

$^1$HNMR (400 MHz, acetone-$d_6$): δ0.79 (t, 3H), 2.34 (q, 2H), 3.40 (m, 2H), 4.70 (m, 1H), 5.36 (m, 1H), 6.93 (app t, 2H), 7.11–7.35 (m, 8H), 7.51 (d, 1H), 7.61 (m, 2H), 7.91 (m, 2H).

Example 12

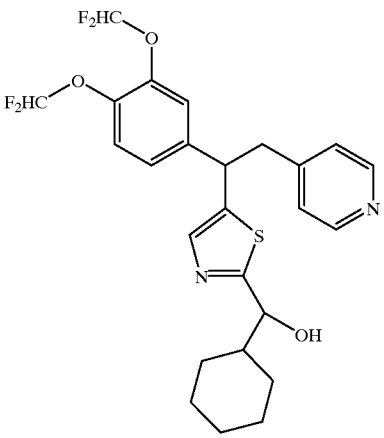

(±/±)-4-{2-[3,4-Bis(difluoromethoxy)phenyl]-2-[5-(2-cyclohexylmethanol)thiazolyl]ethyl}pyridine Example 12 was prepared by the following procedure. To a solution of Intermediate 1 (740 mg, 1.74 mmol) in dichloromethane (20 mL) at 0° C. was added dropwise cyclohexylmagnesium chloride (2.6 mL of a 2M solution in ether, 5.2 mmol). After 1 h, sat. aq. NH$_4$Cl was added and the mixture was extracted with ethyl acetate (3×). The combined organics were washed with water, brine, dried (MgSO$_4$) and concentrated. Flash chromatography of the residue (silica gel; dichloromethane/MeOH 96:4) provided the title compound as a colorless oil (462 mg).

$^1$HNMR (400 MHz, acetone-d$_6$): δ1.15 (m, 5H), 1.5–1.8 (m, 6H), 3.45 (m, 2H), 4.60 (m, 1H), 4.80 (m, 1H), 5.01 (m, 1H), 6.94 (app t, 2H), 7.16–7.50 (m, 6H), 8.35 (m, 2H).

Example 13

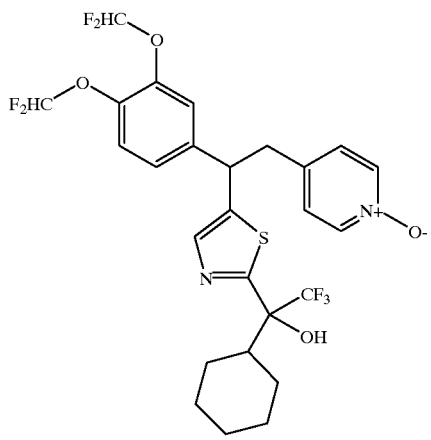

(±/±)-4-{2-[3,4-Bis(difluoromethoxy)phenyl]-2-[5-(2-(1-hydroxy-1-cyclohexyl-2,2,2-trifluoromethyl)ethyl)thiazolyl]ethyl}pyridine N-oxide Example 13 was prepared by the following procedure:

Step 1: (±)-4-{2-[3,4-Bis(difluoromethoxy)phenyl]-2-[5-(2-(cyclohexylcarbonyl)thiazolyl]ethyl}pyridine Following the procedures described in Example 9, Step 1, but substituting the alcohol from Example 12 (446 mg, 0.87 mmol) for the alcohol from Example 8, Step 1, (±)-4-{2-[3,4-Bis(difluoromethoxy)phenyl]-2-[5-(2-(cyclohexylcarbonyl)thiazolyl]ethyl}pyridine (chromatography silica gel; toluene/acetone 4:1 to 3:1) was obtained as an oil (314 mg).

Step 2: (±/±)-4-{2-[3,4-Bis(difluoromethoxy)phenyl]-2-[5-(2-(1-hydroxy-1-cyclohexyl-2,2,2-trifluoromethyl)ethyl)thiazolyl]ethyl}pyridine N-oxide Following the procedures described in Examples 3 and 4, but substituting the ketone from the present Step 1 (295 mg, 0.58 mmol) for Intermediate 1, the title compound was obtained (chromatography silica gel; dichloromethane/MeOH 9:1) as a foam (97 mg).

$^1$HNMR (400 MHz, acetone-d$_6$): δ1.1–1.4 (m, 6H), 1.55–1.95 (m, 4H), 2.3 (m, 1H), 3.50 (m, 2H), 4.82 (m, 1H), 6.06 (m, 1H), 6.96 (app t, 2H), 7.19 (m, 2H), 7.32 (m, 2H), 7.39 (s, 1H), 7.64 (d, 1H), 7.94 (d, 2H).

Example 14

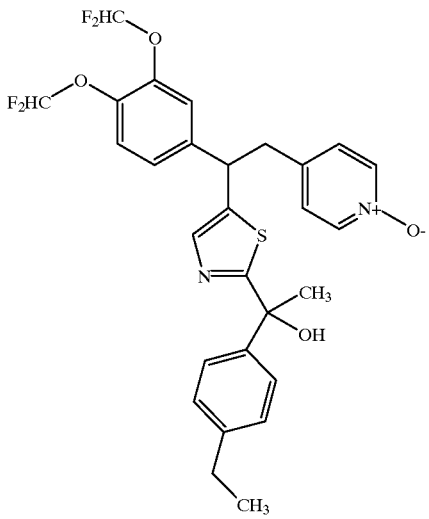

(±/±)-4-{2-[3,4-Bis(difluoromethoxy)phenyl]-2-[5-(2-(1-hydroxy-1-(4-ethyl)phenyl)ethyl)thiazolyl]ethyl}pyridine N-oxide Example 14 was prepared by the following procedure:

Step 1: (±/±)-4-{2-[3,4-Bis(difluoromethoxy)phenyl]-2-[5-(2-(4-ethylphenyl)methanol)thiazolyl]ethyl}pyridine To a solution of Intermediate 1 (426 mg, 1 mmol) in dichloromethane (10 mL) at 0° C. was added dropwise 4-ethylphenylmagnesium bromide (7.2 mL of a 0.42M solution in THF, 3 mmol). After 30 min, a second aliquot of 4-ethylphenylmagnesium bromide (2.5 mL) was added. After a further 1 h, the mixture was warmed to room temperature and sat. aq. NH$_4$Cl was added. The mixture was extracted with ether (2×). The combined organics were washed with brine (2×), dried (MgSO$_4$) and concentrated. Chromatography of the residue (silica gel; dichloromethane/acetone 7:3) provided (±/±)-4-{2-[3,4-Bis(difluoromethoxy)phenyl]-2-[5-(2-(4-ethylphenyl)methanol)thiazolyl]ethyl}pyridine as a yellow syrup (290 mg).

Step 2: (±)-4-{2-[3,4-Bis(difluoromethoxy)phenyl]-2-[5-(2-(4-ethyl)benzoyl)thiazolyl]ethyl}pyridine A mixture of the alcohol from Step 1 (280 mg, 0.53 mmol), MnO$_2$ (274 mg, 3.2 mmol) and Celite® (500 mg) in dichloromethane (15 mL) was stirred at room temperature for 24 h. A second aliquot of MnO$_2$ (137 mg) was added and stirring continued for a further 3 h. The mixture was filtered through Celite®, washing with dichloromethane, and the filtrate was concentrated. Flash chromatography of the residue (silica gel; acetone/dichloromethane 3:7) provided (±)-4-{2-[3,4-Bis(difluoromethoxy)phenyl]-2-[5-(2-(4-ethyl)benzoyl)thiazolyl]ethyl}pyridine as a yellow syrup (236 mg).

Step 3: (±/±)-4-{2-[3,4-Bis(difluoromethoxy)phenyl]-2-[5-(2-(1-hydroxy-1-(4-ethyl)phenyl)ethyl)thiazolyl]ethyl}pyridine To a solution of the ketone from Step 2 (236 mg, 0.45 mmol) in dichloromethane (5 mL) at 0° C. was added dropwise MeMgCl (0.52 mL of a 3M solution in THF, 1.56 mmol). After 15 min, sat. aq. NH₄Cl and ethyl acetate were added. The aqueous phase was extracted with ethyl acetate (3×). The combined organics were dried (MgSO₄) and concentrated. Flash chromatography of the residue (silica gel; dichloromethane/acetone 7:3) provided (±/±)-4-{2-[3,4-Bis(difluoromethoxy)phenyl]-2-[5-(2-(1-hydroxy-1-(4-ethyl)phenyl)ethyl)thiazolyl]ethyl}pyridine as a yellow syrup (228 mg).

Step 4: (±/±)-4-{2-[3,4-Bis(difluoromethoxy)phenyl]-2-[5-(2-(1-hydroxy-1-(4-ethyl)phenyl)ethyl)thiazolyl]ethyl}pyridine N-oxide Following the procedures described in Example 1, Step 4, but substituting the pyridine from the present Step 3 (198 mg, 0.36 mmol) for the pyridine from Example 1, Step 3, the title compound (chromatography silica gel; dichloromethane/MeOH 92.5:7.5) was obtained as a white foam (169mg).

¹HNMR (400 MHz, acetone-d₆): δ1.16 (m, 3H), 1.91 and 1.92 (s each, 3H), 2.57 (m, 2H), 3.42 (m, 2H), 4.73 (m, 1H), 5.54 (m, 1H), 6.94 (app t, 2H), 7.11–7.18 (m, 4H), 7.24–7.36 (m, 3H), 7.45–7.50 (m, 3H), 7.91 (m, 2H).

Example 15

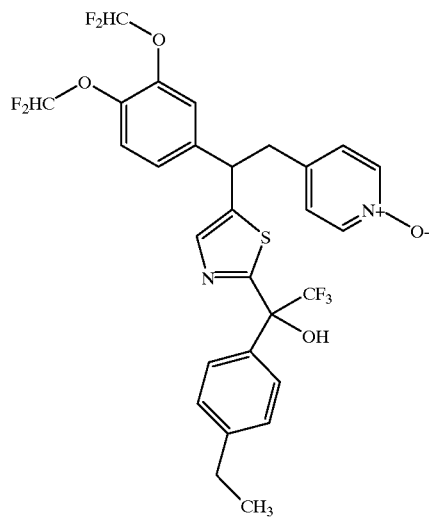

(±/±)-4-{2-[3,4-Bis(difluoromethoxy)phenyl]-2-[5-(2-(1-hydroxy-1-4-ethyl)phenyl-2,2,2-trifluoro)ethyl)thiazolyl]ethyl}pyridine N-oxide Example 15 was prepared by following the procedures described in Examples 3 and 4, but substituting the ketone from Example 14, Step 2 (210 mg, 0.4 mmol) for Intermediate 1. The title compound was obtained (chromatography silica gel; dichloromethane/MeOH 9:1) as a white foam (117 mg).

¹NNMR (400 MHz, acetone-d₆): δ1.20 (m, 3H), 2.63 (m, 2H), 3.48 (m, 2H), 4.82 (m, 1H), 6.92 (app t, 2H), 7.10–7.35 (m, 7H), 7.40 (s, 1H), 7.61–7.74 (m, 3H), 7.93 (d, 2H).

Example 16

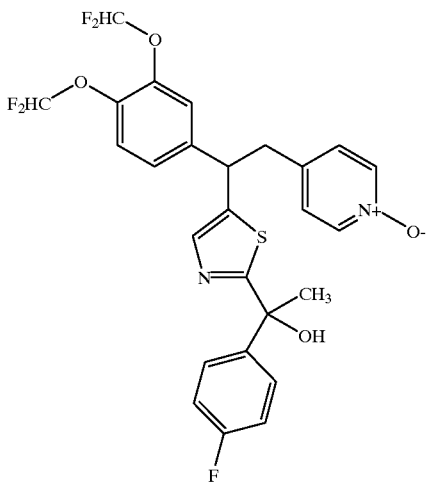

(±/±)-4-{2-[3,4-Bis(difluoromethoxy)phenyl]-2-[5-(2-(1-hydroxy-1-(4-fluoro)phenyl)ethyl)thiazolyl]ethyl}pyridine N-oxide Example 16 was prepared by following the procedures described in Examples 14, but substituting 4-fluorophenylmagnesium bromide for 4-ethylphenylmagnesium bromide. The title compound was obtained (chromatography silica gel; dichloromethane/MeOH 9:1) as a white foam (100 mg).

¹HNMR (400 MHz, acetone-d₆): δ1.91 (m, 3H), 3.46 (m, 2H), 4.73 (m, 1H), 5.78 (m, 1H), 6.92 (app t, 2H), 7.05 (m, 2H), 7.17 (m, 2H), 7.25–7.38 (m, 3H), 7.51 (d, 1H), 7.60 (m, 2H), 7.92 (m, 2H).

Example 17

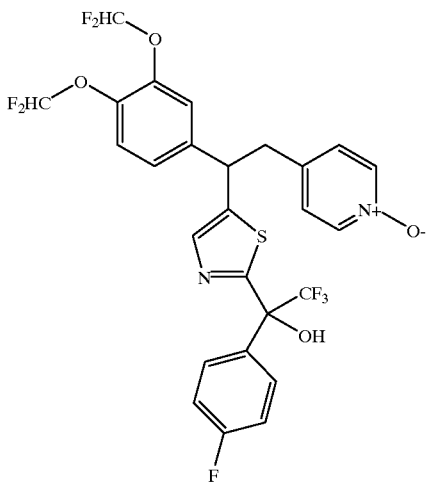

(±/±)-4-{2-[3,4-Bis(difluoromethoxy)phenyl]-2-[5-(2-(1-hydroxy-1-(4-fluoro)phenyl-2,2,2-trifluoro)ethyl)thaizolyl]ethyl}pyridine N-oxide Example 17 was prepared by the following procedure:

Step 1: (±)-4-{2-[3,4-Bis(difluoromethoxy)phenyl]-2-[5-(2-(4-fluoro)benzoyl)thiazolyl]ethyl}pyridine Following the procedures described in Examples 14, Steps 1 and 2, but substituting 4-fluorophenylmagnesium bromide for 4-ethylphenylmagnesium bromide, (±)-4-{2-[3,4-Bis(difluoromethoxy)phenyl]-2-[5-(2-(4-fluoro)benzoyl)thiazolyl]ethyl}pyridine was obtained (chromatography silica gel; hexane/ethyl acetate 2:3 to 3:7) as a white foam (443 mg).

Step 2: (±/±)-4-{2-[3,4-Bis(difluoromethoxy)phenyl]-2-[5-(2-(1-hydroxy-1-(4-fluoro)phenyl-2,2,2-trifluoro)ethyl)thiazolyl]ethyl}pyridine N-oxide Following the procedures described in Examples 3 and 4, but substituting the ketone from the present Step 1 (300 mg, 0.58 mmol) for Intermediate 1, the title compound was obtained (chromatography silica gel; dichloromethane/EtOH 9:1) as a foam (100 mg).

$^1$HNMR (400 MHz, acetone-$d_6$): δ3.49 (m, 2H), 4.83 (m, 1H), 6.94 (app t, 2H), 7.12–7.23 (m, 4H), 7.30 (m, 2H), 7.40 (m, 2H), 7.71 (m, 1H), 7.82 (m, 2H), 7.93 (d, 2H).

Example 18

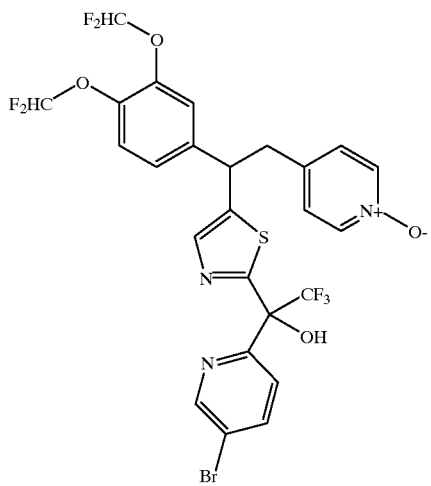

(±/±)-4-{2-[3,4-Bis(difluoromethoxy)phenyl]-2-[5-(2-(1-hydroxy-1-(5-bromopyridin-2-yl)-2,2,2-trifluoro)ethyl)thiazolyl]ethyl}pyridine N-oxide
Example 18 was prepared by the following procedure:

Step 1: (±/±)-4-{2-[3,4-Bis(difluoromethoxy)phenyl]-2-[5-(2-(5-bromopyridin-2-yl)methanol)thiazolyl]ethyl}pyridine To a solution/suspension of 2,5-dibromopyridine (427 mg, 1.8 mmol) in toluene (20 mL) at −78° C. was slowly added n-BuLi (0.72 mL of a 2.3M solution in hexane, 1.65 mmol) and the resulting mixture was stirred at this temperature for 3.5 h. To this mixture was added a solution of Intermediate 1 (639 mg, 1.5 mmol) in toluene (5 mL). After 75 min, sat. aq. NH$_4$Cl was added and the mixture was warmed to room temperature. The mixture was extracted with ethyl acetate (2×) and the combined organics were washed with water (3×), dried (MgSO$_4$), concentrated and used as such in the subsequent reaction below.

Step 2: (±)-4-{2-[3,4-Bis(difluoromethoxy)phenyl]-2-[5-(2-(5-bromopyridin-2-yl)keto)thiazolyl]ethyl}pyridine A mixture of the alcohol from the present Step 1, MnO$_2$ (1.96 g, 22.5 mmol) and Celite® (3 g) in dichloromethane (30 mL) was stirred at room temperature for 24 h. The mixture was filtered through Celite®, washing with dichloromethane, and the filtrate was concentrated. Flash chromatography of the residue (silica gel; ethyl acetate) provided (±)-4-{2-[3,4-Bis(difluoromethoxy)phenyl]-2-[5-(2-(5-bromopyridin-2-yl)keto)thiazolyl]ethyl}pyridine as an oil (247 mg).

Step 3: (±/±)-4-{2-[3,4-Bis(difluoromethoxy)phenyl]-2-[5-(2-(1-hydroxy-1-(5-bromopyridin-2-yl)-2,2,2-trifluoro)ethyl)thiazolyl]ethyl}pyridine N-oxide Following the procedures described in Examples 3 and 4, but substituting the ketone from the present Step 2 (235 mg, 0.40 mmol) for Intermediate 1, the title compound was obtained (chromatography silica gel; dichloromethane/EtOH 9:1) as a yellow foam (32 mg).

$^1$HNMR (400 MHz, acetone-$d_6$): δ3.40–3.57 (m, 2H), 4.84 (m, 1H), 6.94 (app t, 2H), 7.16–7.34 (m, 5H), 7.39 (s, 1H), 7.76 (d, 1H), 7.91–7.95 (m, 2H), 8.13 (m, 1H), 8.21–8.25 (m, 1H), 8.77 (s, 1H).

Example 19

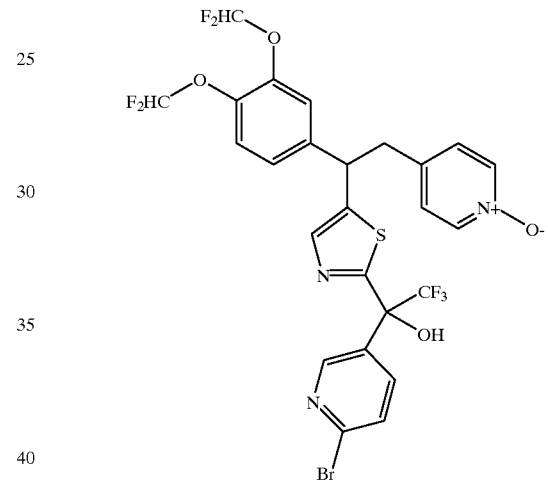

(±/±)-4-{2-[3,4-Bis(dilfuoromethoxy)phenyl]-2-[5-(2-(1-hydroxy-1-(6-bromopyridin-3-yl)-2,2,2-trifluoro)ethyl)thiazolyl]ethyl}pyridine N-oxide
Example 19 was prepared by the following procedure:

Step 1: (±/±)-4-{2-[3,4-Bis(difluoromethoxy)phenyl]-2-[5-(2-(6bromopyridin-3-yl)methanol)thiazolyl]ethyl}pyridine To a solution/suspension of 2,5-dibromopyridine (1.66 g, 7 mmol) in ether (50 mL) at −78° C. was slowly added n-BuLi (2.6 mL of a 2.3M solution in hexane, 6 mmol) and the resulting mixture was stirred at this temperature for 1.5 h. To this mixture was added a solution of Intermediate 1 (2.13 g, 5 mmol) in ether (20 mL). The mixture was stirred at −78° C. for 2 h and then warmed to 0° C. After 3.5 h, sat. aq. NH$_4$Cl (75 mL) was added and the mixture was warmed to room temperature. The mixture was partitioned with ethyl acetate and water and the organic phase was dried (MgSO$_4$), concentrated and used as such in the subsequent reaction.

Step 2: (±/±)-4-{2-[3,4-Bis(difluoromethoxy)phenyl]-2-[5-(2-(1-hydroxy-1-(6-bromopyridin-3-yl)-2,2,2-trifluoro)ethyl)thiazolyl]ethyl}pyridine N-oxide Following the procedures described in Example 18, Steps 2 and 3, but substituting the alcohol obtained from the present Step 1 for the alcohol from Example 18, Step 1, the title compound was obtained (chromatography silica gel; dichloromethane/MeOH 9:1) as a white foam (374 mg).

¹HNMR (400 MHz, acetone-d₆): δ3.41–3.56 (m, 2H), 4.87 (m, 1H), 6.95 (app t, 2H), 7.20 (m, 2H), 7.28–7.35 (m, 2H), 7.40 (s, 1H), 7.69 (m, 1 H), 7.75 (s, 1H), 7.82 (br s, 1H), 7.92 (m, 2H), 8.12 (m, 1H), 8.76 (s, 1H).

Example 20

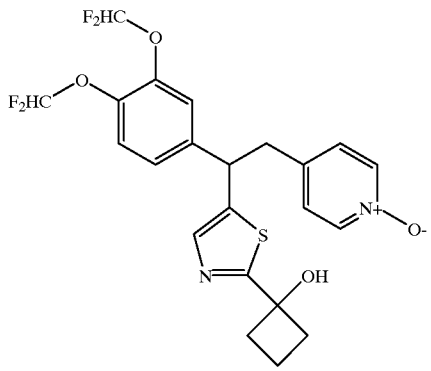

(±)-4-{2-[3,4-Bis(difluoromethoxy)phenyl]-2-{5-[2-(1-hydroxy)cyclobutyl]thiazolyl}ethyl}pyridine N-oxide Example 20 was prepared by following the procedures described in Example 1, but substituting Thiazole 4 for Thiazole 1. The title compound was obtained (chromatography silica gel; dichloromethane/MeOH 92:8) as a white solid (164 mg, m.p. 151–153° C.).

¹HNMR (400 MHz, acetone-d₆): δ1.89 (m, 2H), 2.22 (m, 2H), 2.55 (m, 2H), 3.47 (m, 2H), 4.78 (m, 1H), 5.42 (br s, 1H), 6.95 (app t, 1H), 6.96 (t, 1H), 7.21 (m, 2H), 7.30 (m, 2H), 7.38 (s, 1H), 7.53 (s, 1 H), 7.95 (d, 2H).

Example 21

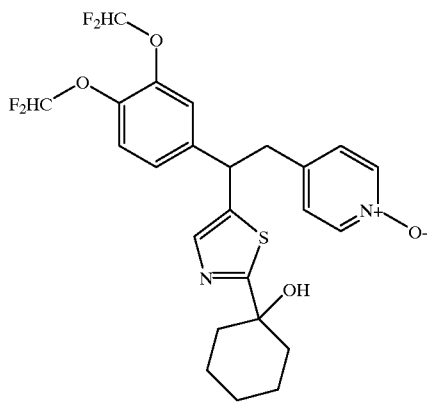

(±)-4-{2-[3,4-Bis(difluoromethoxy)phenyl]-2-{5-[2-1-hydroxy)cyclohexyl]thiazolyl}ethyl}pyridine N-oxide Example 21 was prepared by following the procedures described in Example 1, but substituting Thiazole 5 for Thiazole 1. The title compound was obtained (chromatography silica gel; dichloromethane/MeOH 9:1) as a foam (144 mg).

¹HNMR (400 MHz, acetone-d₆): δ1.30 (m, 1H), 1.50–1.80 (m, 7H), 1.90 (m, 2H), 3.44 (m, 21H), 4.75 (m, 2H), 6.95 (app t, 2H), 7.20 (m, 2H), 7.29 (m, 2H), 7.37 (s, 11), 7.48 (s, 1 H), 7.94 (d, 2H).

Example 22

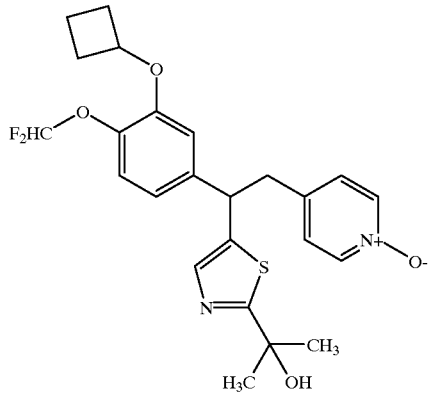

(±)-4-{2-[(3-cyclobutyloxy-4-difluoromethoxy)phenyl]-2-{5-[2-(1-hydroxy-1-methyl)ethyl]thaizolyl}ethyl}pyridine N-oxide Example 22 was prepared by the following procedure:

Step 1: (±)-(3-Cyclobutyloxy-4-difluoromethoxy)phenyl-5-{2-(1-methyl-1-[(2-trimethylsilylethoxy)methoxy]ethyl}thiazolylcarbinol To a solution of Thiazole 1 (1.0 g, 3.66 mmol) in anhydrous ether (10 mL) at −78° C. was added n-BuLi (2.3 mL of a 1.6M solution in hexane, 3.66 mmol). After 40 min, a solution of 3-cyclobutyloxy-4-difluoromethoxybenzaldehyde (886 mg, 3.66 mmol) in anhydrous ether (2 mL) was added. The mixture was stirred at −78° C. for 35 min and then 25% aq. NH₄OAc was added. The mixture was allowed to warm to room temperature and then partitioned with ethyl acetate and water. The aqueous phase was extracted with ethyl acetate and the combined organics were washed with brine, dried (MgSO₄) and concentrated. Flash chromatography of the residue (silica gel; hexane/ethyl acetate 65:35) provided (±)-(3-Cyclobutyloxy-4-difluoromethoxy)phenyl-5-{2-(1-methyl-1-[(2-trimethylsilylethoxy)methoxy]ethyl}thiazolylcarbinol as an amber oil (1.2 g).

Step 2: (±)-4-{2-[(3-Cyclobutyloxy-4-difluoromethoxy)phenyl]-2-[5-(2-(1-methyl-1-[(2-trimethyislylethoxy)methoxy]ethyl)thiazolyl]ethyl}pyridine To a solution of pyridine,(0.47 mL, 5.82 mmol) in toluene (2 mL) at room temperature was slowly added thionyl chloride (0.20 mL, 2.79 mmol) and the resulting mixture was stirred for 10 min. To this mixture was slowly added a solution of the alcohol from the present Step 1 (1.2 g, 2.33 mmol) in toluene (2 mL). The mixture was stirred for 25 min to give a precipitate. The liquid was decanted and the residual solid washed with toluene. The combined organics were concentrated to provide the crude chloride as an amber oil that was used immediately.

To a solution of ethyl 4-pyridylacetate (1.15 g, 7 mmol) in THF (10 mL) and HMPA (1.21 mL, 7 mmol) at room temperature was added potassium bis(trimethylsilyl)amide

47

(14 mL of a 0.5M solution in toluene, 7 mmol). The resulting mixture was stirred for 30 min and then a THF (5 mL) solution of the crude chloride prepared above was added and then stirred for 17 h at 25° C. Then, 25% aq. NH₄OAc was added, the layers were separated and the aqueous phase was extracted with ethyl acetate. The combined organics were washed successively with brine, dried (MgSO₄) and concentrated to give a thick orange oil. This material was dissolved in a mixture of THF/MeOH/water (3:1:1, 25 mL), LiOH (557 mg) was added and the mixture was heated at 70° C. for 1 h. After cooling to room temperature, 1N HCl (25 mL) was slowly added. The mixture was extracted three times with ethyl acetate and the combined organics were washed with brine, dried (MgSO₄) and concentrated. Flash chromatography of the residue (silica gel; ethyl acetate/hexane 3:1) provided (±)-4-{2-[(3-Cyclobutyloxy-4-difluoromethoxy)phenyl]-2-[5-(2-(1-methyl-1-[(2-trimethylsilylethoxy)methoxy]ethyl)thiazolyl]ethyl}pyridine as an orange oil (892 mg).

Step 3: (±)-4-{2-[(3-Cyclobutyloxy-4-difluoromethoxy)phenyl]2-[5-(2-(1-methyl-1-[(2-trimethylsilylethoxy)methoxy]ethyl)thiazolyl]ethyl}pyridine N-oxide A mixture of the (±)-4-{2-[(3-Cyclobutyloxy-4-difluoromethoxy)phenyl]-2-[5-(2-(1-methyl-1-[(2-trimethylsilylethoxy)methoxy]ethyl)thiazolyl]ethyl}pyridine from Step 2 (892 mg, 1.51 mmol) and MMPP (747 mg, 1.51 mmol) in dichloromethane (9 mL) and MeOH (1 mL) was stirred at room temperature for 16 h. The mixture was partitioned with ethyl acetate and sat. aq. NaHCO₃. The aqueous phase was extracted with ethyl acetate and the combined organics were washed with brine, dried (MgSO₄) and concentrated. Flash chromatography of the residue (silica gel; dichloromethane/MeOH 9:1) provided (±)-4-{2-[(3-Cyclobutyloxy-4-difluoromethoxy)phenyl]-2-[5-(2-(1-methyl-1-[(2-trimethylsilylethoxy)methoxy]ethyl)thiazolyl]ethyl}pyridine N-oxide as a pale yellow foam (782 mg).

Step 4: (±)-4-{2-[(3-Cyclobutyloxy-4-difluoromethoxy)phenyl]-2-{5-[2-(1-hydroxy-1-methyl)ethyl]thiazolyl}ethyl}pyridine N-oxide To a solution of the protected alcohol, (±)-4-{2-[(3-Cyclobutyloxy-4-difluoromethoxy)phenyl]-2-[5-(2-(1-methyl-1-[(2-trimethylsilylethoxy)methoxy]ethyl)thiazolyl]ethyl}pyridine N-oxide, from Step 3 (782 mg, 1.29 mmol) in dichloromethane (10 mL) at 0° C. was added TFA (1 mL) and the mixture was stirred at 0° C. for 20 min. The mixture was warmed to room temperature and then stirred for an additional 5 h. 25% aq. NH₄OAc was added and the mixture was extracted with ethyl acetate. The organics were washed with brine, dried (MgSO₄) and concentrated. Flash chromatography of the residue (silica gel; dichloromethane/MeOH 9:1) provided the title product as an off white solid (520 mg).

¹HNMR (400 MHz, acetone-d₆): δ1.51 (s, 6H), 1.67 (m, 1H), 1.81 (m, 1H), 2.0–2.2 (m, 2H), 2.35–2.50 (m, 2H), 3.42 (m, 2H), 4.66 (t, 1H), 4.74 (m, 1H), 4.91 (br s, 1H), 6.84 (t, 1H), 6.92 (m, 1H), 6.97 (m, 1H), 7.08 (d, 1H), 7.18 (d, 2H), 7.48 (s, 1H), 7.97 (d, 2H).

48

Example 23

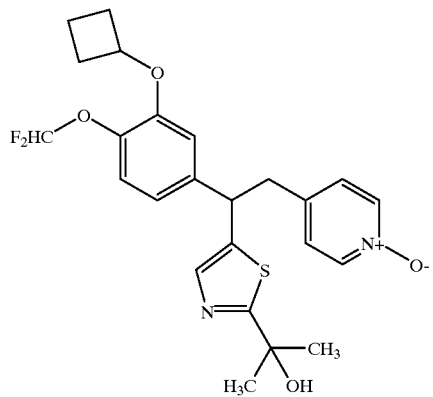

Chiral 4-{2-[3-cyclobutyloxy-4-difluoromethoxy) phenyl]-2-{5-[2-(1-hydroxy-1methyl)ethyl] thiazolyl}ethyl}pyridine N-oxide Example 23 was prepared by the following procedure:

Step 1: Resolution of (±)-4-{2-[(3-Cyclobutyloxy-4-difluoromethoxy)phenyl]-2-[5-(2-(1-methyl-1-[(2-trimethylsilylethoxy)methoxy]ethyl)thiazolyl] ethyl}pyridine A solution of (±)-4-{2-[(3-Cyclobutyloxy-4-difluoromethoxy)phenyl]-2-[5-(2-(1-methyl-1-[(2-trimethylsilylethoxy)methoxy]ethyl)thiazolyl]ethyl}pyridine (Example 22, Step 2; 2.3 g) in isopropanol/hexane (30 mL, 1:4) was injected (5×6 mL) onto a Chiralpak® AD preparative (5 cm×50 cm) HPLC column (eluting with hexane/isopropanol 96:4 at 75 mL/min with UV detection at 280 nm). The enantiomers were separated with the faster eluting enantiomer having a retention time of ~46 min (Enantiomer 1) and the slower eluting enantiomer (Enantiomer 2) having a retention time of ~51 min. The eluants were concentrated to provide the enantiomers as off-white gums: Enantiomer 1 (761 mg) and Enantiomer 2 (547 mg).

Step 2: Chiral 4-{2-[(3-Cyclobutyloxy-4-difluoromethoxy)phenyl]-2-{5-[2-(1-hydroxy-1-methyl)ethyl]thiazolyl}ethyl}pyridine N-oxide Following the procedures described in Example 22, Steps 3 and 4, but substituting chiral pyridine from the present Step 1 (Enantiomer 1; 750 mg, 1.27 mmol) for the racemic pyridine from Example 22, Step 2, the title compound was obtained (chromatography silica gel; chloroform/EtOH 9:1 to 4:1) as a white foam (473 mg).

¹NMR (500 MHz, acetone-d₆): δ1.52 (s, 6H), 1.68 (m, 1H), 1.81 (m, 1H), 2.0–2.2 (m, 2H), 2.38–2.50 (m, 2H), 3.36–3.47 (m, 2H), 4.66 (t, 1H), 4.75 (m, 1H), 4.90 (br s, 1H), 6.83 (t, 1H), 6.92 (m, 1H), 6.96 (m, 1H), 7.08 (d, 1H), 7.17 (d, 2H), 7.47 (s, 1H), 7.97 (d, 2H).

Example 24

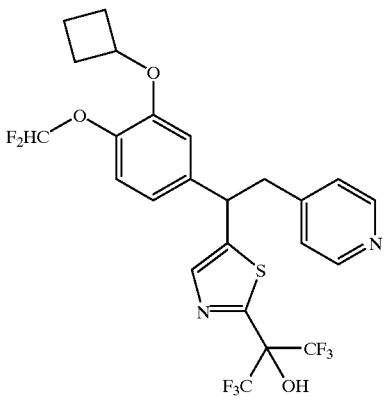

(±)-4-{2-[(3-cyclobutyloxy-4-difluoromethoxy)
phenyl]-2-{5-[2-(1-hydroxy-1-trifluoromethyl-2,2,2-
trifluoro)ethyl]thiazolyl}ethyl}pyridine Example 24 was prepared by following the procedures described in Example 5, but substituting 3-cyclobutyloxy-4-difloromethoxybenzaldehyde for 3,4-bis(difluoromethoxy)benzaldehyde, the title compound (chromatography silica gel; toluene/acetone 7:3) was obtained as a foam (277 mg).

$^1$HNMR (500 MHz, acetone-$d_6$): δ1.66 (m, 1H), 1.80 (m, 1H), 2.0–2.2 (m, 2H), 2.30–2.50 (m, 2H), 3.40–3.53 (m, 2H), 4.70 (m, 1H), 4.78 (t, 1H), 6.83 (t, 1H), 6.94 (m, 2H), 7.06 (d, 1H), 7.16 (d, 2H), 7.68 (s, 1H), 8.37 (br s, 2H).

Example 25

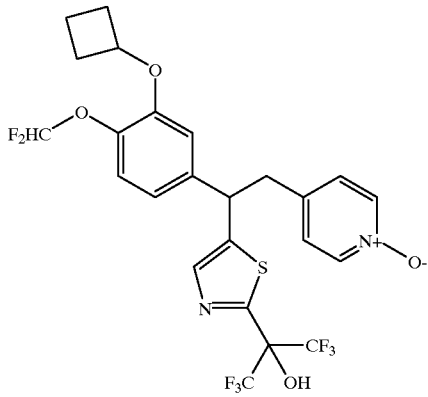

(±)-4-{2[(3-cyclobutyloxy-4-difluoromethoxy)
phenyl]-2-{5-[2-(1-hydroxy-1-trifluoromethyl-2,2,2-
trifluoro)ethyl]thiazolyl}ethyl}pyridine N-oxide Example 25 was prepared by following the procedures described in Example 6, but substituting Example 24 (203 mg, 0.35 mmol) for Example 5. The title compound (chromatography silica gel; dichloromethane/MeOH 93:7) was obtained as a white foam (100 mg).

$^1$HNMR (400 MHz, acetone-$d_6$): δ1.67 (m, 1H), 1.81 (m, 1H), 2.0–2.2 (m, 2H), 2.30–2.50 (m, 2H), 3.45–3.59 (m, 2H), 4.75 (m, 1H), 4.81 (t, 1H), 6.85 (t, 1H), 6.94–7.0 (m, 2H), 7.10 (d, 1H), 7.19 (d, 2H), 7.81 (s, 1H), 7.97 (br d, 2H), 8.45 (br s, 1H).

Example 26 and 27

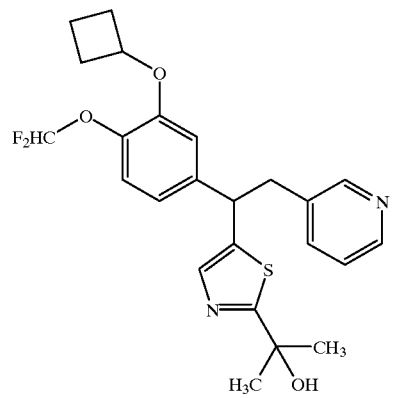

Chiral 3-{2-[(3-cyclobutyloxy-4-difluoromethoxy)
phenyl]-2-{5-[2-(1-hydroxy-1methyl)ethyl]
thaizolyl}ethyl}pyridine Examples 26 and 27 were prepared by the following precedure:

Step 1: (±)-3-{2-[(3-Cyclobutyloxy-4-
difluoromethoxy)phenyl]-2-{5-[2-(1-hydroxy-1-
methyl)ethyl]thiazolyl]ethyl}pyridine To a solution of pyridine (1.8 mL, 22.2 mmol) in toluene (50 mL) at 0° C. was slowly added thionyl chloride (0.78 mL, 10.7 mmol) and the resulting mixture was stirred at room temperature for 15 min. To this mixture was slowly added a solution of the alcohol from Example 22, Step 1 (4.6 g, 8.9 mmol), in toluene (25 mL). The mixture was stirred for 20 min to give a precipitate. The mixture was filtered and the residual solid washed with toluene. The combined organics were concentrated to provide the crude chloride as an amber oil that was used immediately.

To a solution of ethyl 3-pyridylacetate (4.4 g, 26.7 mmol) in THF (110 mL) and HMPA (4.6 mL, 26.7 mmol) at room temperature was added potassium bis(trimethylsilyl)amide (53.4 mL of a 0.5M solution in toluene, 7 mmol). The resulting mixture was stirred for 20 min and then a THF (20 mL) solution of the crude chloride prepared above was added and then stirred for 17 h at 25° C. The mixture was poured into 25% aq. NH$_4$OAc, the layers were separated and the aqueous phase was extracted with ethyl acetate (3×). The combined organics were washed successively with water (3×), dried (MgSO$_4$) and concentrated. Flash chromatography of the residue (silica gel; ethyl acetate/hexane 1:1 to 3:2) provided the esters as a yellow oil (2.5 g).

This material (2.5 g, 3.8 mmol) was dissolved in a mixture of THF/MeOH/water (3:1:1, 30 mL), 2N LiOH (5.7 mL, 11.4 mmol) was added and the mixture was heated at 70° C. for 30 min and then stirred at room temperature for 15 h. 4N HCl (25 mL) was slowly added, bringing the mixture to ~pH 5. The mixture was concentrated and then extracted three times with ethyl acetate. The combined organics were washed with water (3×), dried (MgSO$_4$) and concentrated to give the acid (2.1 g). The acid was dissolved in DMSO (10 mL) and heated at 150° C. for 7 h and then stirred at room temperature for 15 h. Water (50 mL) and brine (5 mL) were added and the mixture was extracted with dichloromethane (3×). The combined organics were washed with water (3×), dried (MgSO$_4$) and concentrated. Flash chromatography of the residue (silica gel; ethyl acetate/EtOH 1:0 to 9:1) provided the title product as an oil (855 mg).

Step 2: Resolution of (±)-3-{2-[(3-Cyclobutyloxy-4-difluoromethoxy)phenyl]-2-{5-[2-(1-hydroxy-1-methyl)ethyl]thiazolyl]ethyl}pyridine A solution of the material from the present Step 1 (855 mg) in EtOH/hexane (5 mL, 2:3) was injected onto a Chiralpak® AD preparative (5 cm×50 cm) HPLC column (eluting with hexane/EtOH 85:15 at 80 mL/min with UV detection at 280 nm). The enantiomers were separated with the faster eluting enantiomer having a retention time of ~25 min (Enantiomer 1) and the slower eluting enantiomer (Enantiomer 2) having a retention time of ~34 min. The eluants were concentrated to provide the enantiomers as white foams: Enantiomer 1 (Example 26, 400 mg) and Enantiomer 2 (Example 27, 385 mg).

$^1$HNMR (500 MHz, acetone-d$_6$) for both enantiomers: δ1.52 (s, 6H), 1.67 (m, 1H), 1.81 (m, 1H), 2.0–2.2 (m, 2H), 2.34–2.50 (m, 2H), 3.34–3.49 (m, 2H), 4.63 (t, 1H), 4.73 (m, 1H), 4.86 (s, 1H), 6.82 (t, 1H), 6.90–6.95 (m, 2H), 7.07 (d, 1H), 7.18 (m, 1H), 7.46 (s, 1H), 7.55 (d, 1H), 8.42 (m, 1H), 8.47 (s, 1H).

Example 28

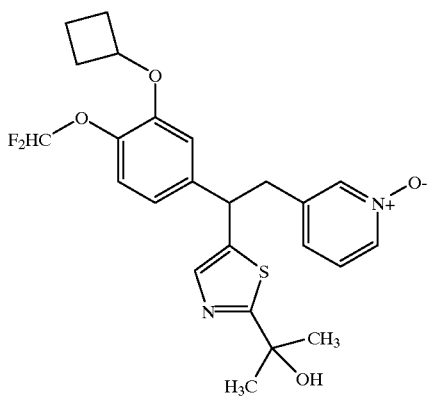

Chiral 3-{2-[(3-cyclobutyloxy-4-difluoromethoxy)phenyl]-2-{5-[2-(1-hydroxy-1-methyl)ethyl]thiazolyl}ethyl}pyridine N-oxide Example 28 was prepared by the following procedure. A mixture of Example 26 (Enantiomer 1; 400 mg, 0.87 mmol) and MMPP (430 mg, 0.87 mmol) in dichloromethane (9 mL) and MeOH (0.9 mL) was stirred at room temperature for 16 h. The mixture was partitioned with dichloromethane and sat. aq. NaHCO$_3$. The aqueous phase was extracted with dichloromethane and the combined organics were washed with brine, dried (MgSO$_4$) and concentrated. Flash chromatography of the residue (silica gel; dichloromethane/EtOH 9:1 to 4:1) provided the title compound as a white foam (280 mg).

$^1$HNMR (500 MHz, acetone-d$_6$): δ1.52 (s, 6H), 1.66 (m, 1H), 1.81 (m, 1H), 2.0–2.2 (m, 2H), 2.37–2.50 (m, 2H), 3.33–3.47 (m, 2H), 4.69 (t, 1H), 4.75 (m, 1H), 4.93 (br s, 1H), 6.82 (t, 1H), 6.93–7.00 (m, 2H), 7.09 (t, 2H), 7.20 (t, 1H), 7.49 (s, 1H), 7.92 (d, 1H), 8.02 (s, 1H).

Example 29

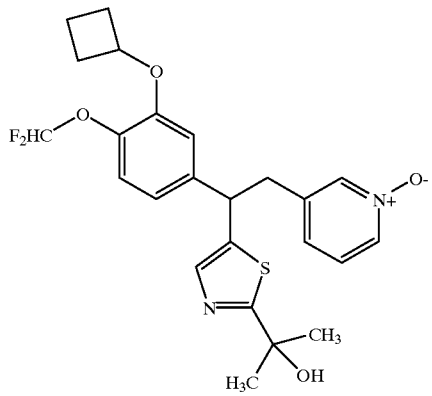

Chiral 3-{2-[(3-cyclobutyloxy-4-difluoromethoxy)phenyl]-2-{5-[2-(1hydroxy-1methyl)ethyl]thiazolyl}ethyl}pyridine N-oxide Example 29 was prepared by following the procedures described in Example 28, but substituting Example 27 (Enantiomer 2; 385 mg, 0.84 mmol) for Example 26. The title compound (chromatography silica gel; dichloromethane/EtOH 9:1 to 4:1) was obtained as a white foam (310 mg).

$^1$HNMR (500 MHz, acetone-d$_6$): δ1.52 (s, 6H), 1.66 (m, 1H), 1.81 (m, 1H), 2.0–2.2 (m, 2H), 2.37–2.50 (m, 2H), 3.33–3.47 (m, 2H), 4.69 (t, 1H), 4.75 (m, 1H), 4.93 (br s, 1H), 6.82 (t, 1H), 6.93–7.00 (m, 2H), 7.09 (t, 2H), 7.20 (t, 1H), 7.49 (s, 1H), 7.92 (d, 1H), 8.02 (s, 1H).

Examples 30 and 31

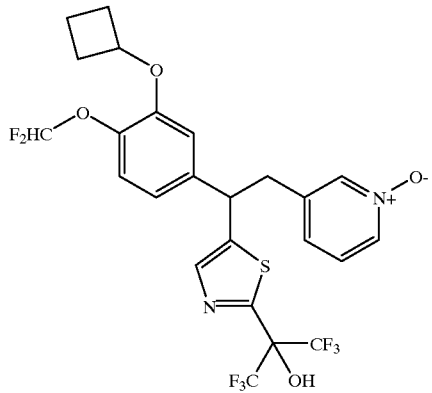

Chiral 3-{2-[(3-cyclobutyloxy-4-difluoromethoxy)phenyl]-2-{5-[2-(1-hydroxy-1-trifluoromethyl-2,2,2-trifluoro)ethyl]thiazolyl}ethyl}pyridine N-oxide Examples 30 and 31 were prepared by the following procedure:

Step 1: (±)-(3-Cyclobutyloxy-4-difluoromethoxy)phenyl-5-{2-(1-trifluoromethyl-1-[(2-trimethylsilylethoxy)methoxy]-2,2,2-trifluoroethyl}thiazolylcarbinol To a solution n-BuLi (8.5 mL of a 1.6M solution in hexane, 13.6 mmol) in anhydrous ether (20 mL) at −78° C.

was added a solution of Thiazole 2 (5.17 g, 13.55 mmol) in anhydrous ether (10 mL). After 1.5 h, this mixture was added to a solution of 3-cyclobutyloxy-4-difluoromethoxybenzaldehyde (2.17 g, 8.97 mmol) in anhydrous ether (30 mL) at −78° C. The mixture was stirred at −78° C. for 2 h and then sat. aq. NH$_4$Cl was added. The mixture was extracted with ethyl acetate and the organics were washed with brine, dried (Na$_2$SO$_4$) and concentrated. Flash chromatography of the residue (silica gel; hexane/ethyl acetate 95:5 to 7:3) provided (±)-(3-Cyclobutyloxy-4-difluoromethoxy)phenyl-5-{2-(1-trifluoromethyl-1-[(2-trimethylsilylethoxy)methoxy]-2,2,2-trifluoroethyl}thiazolylcarbinol as a yellow oil (4.99 g).

Step 2: (±)-3-{2-[(3-Cyclobutyloxy-4-difluoromethoxy)phenyl]-2-{5-[2-(1-hydroxy-1-trifluoromethyl-2,2,2-trifluoro)ethyl]thiazolyl}ethyl}pyridine N-oxide To a solution of pyridine (2 mL, 26.7 mmol) in toluene (5 mL) at 0° C. was slowly added thionyl bromide (1 mL, 12.9 mmol) and the resulting mixture was stirred for 10 min. To this mixture was slowly added a solution of the alcohol from the present Step 1 (4.99 g, 8.0 mmol) in toluene (15 mL). The mixture was warmed to room temperature and stirred for 45 min to give a precipitate. The mixture was added directly to a silica gel column and eluted with hexane/ethyl acetate (4:1) to provide the crude bromide as a pale yellow oil (3.67 g) that was used immediately.

To a solution of ethyl 3-pyridylacetate N-oxide (2.4 g, 13.25 mmol) in THF (80 mL) and HMPA (2.4 mL, 13.8 mmol) at 0° C. was added potassium bis(trimethylsilyl)amide (27 mL of a 0.5M solution in toluene, 13.5 mmol). The resulting mixture was warmed to room temperature and stirred for 1.5 h. The mixture was re-cooled to 0° C. and then a THF (10 mL) solution of the crude bromide prepared above (2.97 g, 4.33 mmol) was added. After stirring for 17 h at 25° C., the mixture was poured into sat. aq. NH$_4$Cl, the layers were separated and the aqueous phase was extracted with ethyl acetate. The combined organics were washed with brine, dried (Na$_2$SO$_4$) and concentrated. Flash chromatography of the residue (silica gel; dichloromethane/EtOH 98:2 to 95:5) provided the esters as a yellow oil (3.2 g).

This material (3.2 g, 3.7 mmol) was dissolved in a mixture of THF/MeOH/water (3:1:1, 35 mL), 1.7N LiOH (7 mL, 11.9 mmol) was added and the mixture was heated at 60° C. for 5 h. A second aliquot of 1.7N LiOH (7 mL) was added and heating was continued for a further 4 h. The mixture was cooled to room temperature and then 2N HCl (14 mL) was slowly added. The mixture was concentrated and partitioned between ethyl acetate and water. The aqueous phase was extracted with ethyl acetate and the combined organics were washed with brine, dried (Na$_2$SO$_4$) and concentrated to give the acid (2.64 g). The acid was dissolved in DMSO (20 mL) and heated at 110–130° C. for 4.5 h and then stirred at room temperature for 15 h. Water (200 mL) was added and the mixture was extracted with dichloromethane (3×). The combined organics were washed with brine, dried (Na$_2$SO$_4$) and concentrated. Flash chromatography of the residue (silica gel; dichloromethane/MeOH/10% aq. NH$_4$OH 90:5:5) provided (±)-3-{2-[(3-Cyclobutyloxy-4-difluoromethoxy)phenyl]-2-{5-[2-(1-hydroxy-1-trifluoromethyl-2,2,2-trifluoro)ethyl]thiazolyl}ethyl}pyridine N-oxide as a white foam (1.4 g).

Step 3: Resolution of (±)-3-{2-[(3-Cyclobutyloxy-4-difluoromethoxy)phenyl]-2-{5-[2-(1-hydroxy-1-trifluoromethyl-2,2,2-trifluoro)ethyl]thiazolyl}ethyl}pyridine N-oxide A solution of the material from the present Step 2 (1.4 g) in EtOH/hexane (20 mL, 3:7) was injected (4×5 mL) onto a Chiralpak® AD preparative (5 cm×50 cm) HPLC column (eluting with hexane/EtOH 9:1 at 60–80 mL/min with UV detection at 270nm). The enantiomers were separated with the faster eluting enantiomer having a retention time of ~16 min (Enantiomer 1, Example 30) and the slower eluting enantiomer (Enantiomer 2, Example 31) having a retention time of ~19 min. The eluants were concentrated to provide the enantiomers as white foams: Enantiomer 1 (579 mg) and Enantiomer 2 (132 mg).

$^1$HNMR (500 MHz, acetone-d$_6$) for each enantiomer: δ1.65 (m, 1H), 1.81 (m, 1H), 2.0–2.2 (m, 2H), 2.35–2.50 (m, 2H), 3.43–3.57 (m, 2H), 4.76 (m, 1H), 4.87 (t, 1H), 6.85 (t, 1H), 6.96–7.02 (m, 2H), 7.10 (t, 2H), 7.22 (t, 1H), 7.35 (s, 1H), 7.94 (d, 1H), 8.06 (s, 1H), 8.28 (br s, 1H).

Example 32

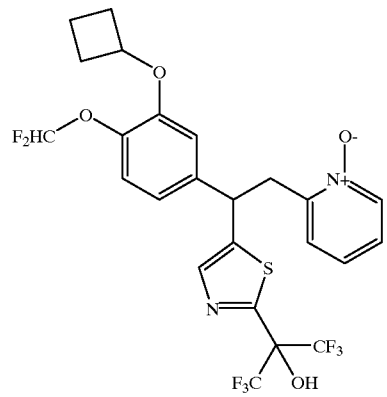

(±)-2-{2[(3-cyclobutyloxy-4-difluoromethoxy)phenyl]-2-{5-[2-(1-hydroxy-1-trifluoromethyl-2,2,2-trifluoro)ethyl]thiazolyl}ethyl}pyridine N-oxide Example 32 was prepared by the following procedure:

Step 1: (±)-2-{2-[(3-Cyclobutyloxy-4-difluoromethoxy)phenyl]-2-{5-[2-(1-trifluoromethyl-1-[(2-trimethylsilylethoxy)methoxy]-2,2,2-trifluoroethyl]thiazolyl}ethyl}pyridine To a solution of diisopropylamine (0.14 mL, 1 mmol) in THF (2 mL) at 0° C. was added n-BuLi (0.62 mL of a 1.6M solution in hexane, 0.99 mmol). After 45 min, the resulting mixture was cooled to −78° C. and ethyl 2-pyridylacetate (0.15 mL, 0.98 mmol) was added. The mixture stirred for 1 h and then a THF (4 mL) solution of the bromide prepared in Example 30, Step 2 (0.22 g, 0.33 mmol) was added. After stirring for 17 h at 25° C., the mixture was poured into 25% aq. NH$_4$OAc. The aqueous phase was extracted with ethyl acetate and the organics were washed with brine, dried (Na$_2$SO$_4$) and concentrated.

This material was dissolved in a mixture of THF/MeOH/water (3:1:1, 10 mL), 1.7N LiOH (2 mL, 3.4 mmol) was added and the mixture was heated at 60° C. for 2.5 h. The mixture was cooled to room temperature and then 2N HCl (2 mL) was slowly added. The mixture was concentrated and partitioned between ethyl acetate and 25% aq. NH$_4$OAc. The aqueous phase was extracted with ethyl acetate and the combined organics were washed with brine, dried (Na$_2$SO$_4$) and concentrated. Flash chromatography of the residue (silica gel; hexane/ethyl acetate 7:3) provided the protected alcohol, (±)-2-{2-[(3-Cyclobutyloxy-4-difluoromethoxy)

phenyl]-2-{5-[2-(1-trifluoromethyl-1-[(2-trimethylsilylethoxy)methoxy]-2,2,2-trifluoroethyl]thiazolyl}ethyl}pyridine, as an oil (169 mg).

Step 2: (±)-2-{2-[(3-Cyclobutyloxy-4-difluoromethoxy)phenyl]-2-{5-[2-(1-hydroxy-1-trifluoromethyl-2,2,2-trifluoro)ethyl]thiazolyl}ethyl}pyridine A mixture of the protected alcohol from the present Step 1 (169 mg, 0.24 mmol) and TBAF (2.5 mL of a 1M solution in THF, 2.5 mmol) in THF (3 mL) was heated at 60° C. for 17 h. 25% aq. NH$_4$OAc was added, the mixture was extracted with ethyl acetate and the combined organics were washed with brine, dried (Na$_2$SO$_4$) and concentrated. Flash chromatography of the residue (silica gel; hexane/ethyl acetate 1:1) provided (±)-2-{2-[(3-Cyclobutyloxy-4-difluoromethoxy)phenyl]-2-{5-[2-(1-hydroxy-1-trifluoromethyl-2,2,2-trifluoro)ethyl]thiazolyl}ethyl}pyridine as an oil (107 mg).

Step 3: (±)-2-{2-[(3-Cyclobutyloxy-4-difluoromethoxy)phenyl]-2-{5-[2-(1-hydroxy-1-trifluoromethyl-2,2,2-trifluoro)ethyl]thiazolyl}ethyl}pyridine N-oxide A mixture of (±)-2-{2-[(3-Cyclobutyloxy-4-difluoromethoxy)phenyl]-2-{5-[2-(1-hydroxy-1-trifluoromethyl-2,2,2-trifluoro)ethyl]thiazolyl}ethyl}pyridine from the present Step 2 (107 mg, 0.19 mmol) and MMPP (185 mg, 0.37 mmol) in dichloromethane (5 mL) and MeOH (0.5 mL) was stirred at room temperature for 2 h. A second aliquot of MMPP (185 mg) was added and the mixture was stirred for 48 h. The mixture was filtered through Celite® and concentrated. Flash chromatography of the residue (silica gel; dichloromethane/MeOH/10% aq. NH$_4$OH 95:2.5:2.5), followed by a second chromatography of the mixed fractions (silica gel; ethyl acetate/EtOH 95:5) provided the title compound as a white foam (26 mg).

$^1$HNMR (500 MHz, acetone-d$_6$): δ1.65 (m, 1H), 1.80 (m, 1H), 1.95–2.18 (m, 2H), 2.32–2.48 (m, 2H), 3.60 (m, 1H), 3.75 (m, 1), 4.63 (m, 1H), 5.28 (t, 1H), 6.83 (t, 1H), 6.90–7.97 (m, 2H), 7.09 (d, 2H), 7.15 (m, 2H), 7.29 (m, 1H), 7.80 (s, 1H), 8.23 (d, 1H), 8.70 (br s, 1H).

Example 33

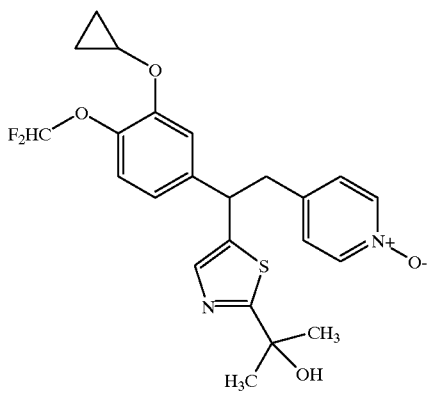

(±)-4-{2-[(3-cyclopropyloxy-4-difluoromethoxy)phenyl]-2-{5-[2-(1-hydroxy-1-methyl)ethyl]thiazolyl}ethyl}pyridine N-oxide Example 33 was prepared by following the procedures described in Example 22, but substituting 3-cyclopropyloxy-4-difluoromethoxybenzaldehyde for 3-cyclobutyloxy-4-difluoromethoxybenzaldehyde. The title compound (chromatography silica gel; dichloromethane/EtOH 7:3) was obtained as a white foam (126 mg).

$^1$HNMR (400 MHz, acetone-d$_6$): δ0.60–0.85 (m, 4H), 1.52 (s, 6H), 3.36–3.50 (m, 2H), 3.88 (m, 1H), 4.69 (t, 1H), 4.95 (s, 1H), 6.76 (t, 1H), 6.95 (m, 1H), 7.07 (d, 1H), 7.18 (d, 2H), 7.41 (m, 1H), 7.48 (s, 1H), 7.96 (d, 2H).

Example 34

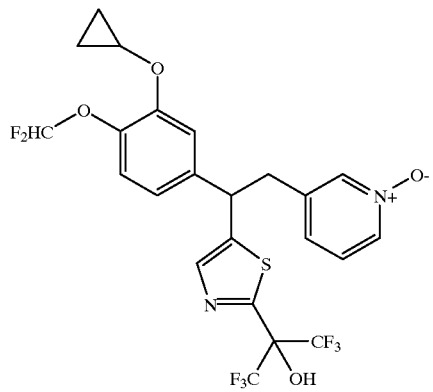

(±)-3-{2-[(3-cyclopropyloxy-4-difluoromethoxy)phenyl]-2-{5-[2-(1-hydroxy-1-trifluoromethyl-2,2,2-trifluoro)ethyl]thiazolyl}ethyl}pyridine N-oxide Example 34 was prepared by the following procedure:

Step 1: (±)-(3-Cyclopropyloxy-4-difluoromethoxy)phenyl-5-{2-(1-trifluoromethyl-1-[(2-trimethylsilylethoxy)methoxy]-2,2,2-trifluoroethyl}thiazolylcarbinol To a solution n-BuLi (13 mL of a 1.6M solution in hexane, 20.8 mmol) in anhydrous ether (40 mL) at −78° C. was added a solution of Thiazole 2 (8.07 g, 21.2 mmol) in anhydrous ether (25 mL). After 1.5 h, this mixture was added to a solution of 3-cyclopropyloxy-4-difluoromethoxybenzaldehyde (3.03 g, 13.3 mmol) in anhydrous ether (30 mL) at −78° C. The mixture was stirred at −78° C. for 1.75 h and then sat. aq. NH$_4$Cl was added. The mixture was extracted with ethyl acetate and the organics were washed with brine, dried (Na$_2$SO$_4$) and concentrated. Flash chromatography of the residue (silica gel; hexane/ethyl acetate 9:1 to 7:3) provided the alcohol, (±)-(3-Cyclopropyloxy-4-difluoromethoxy)phenyl-5-{2-(1-trifluoromethyl-1-[(2-trimethylsilylethoxy)methoxy]-2,2,2-trifluoroethyl}thiazolylcarbinol, as a yellow oil (7.05 g).

Step 2: (±)-3-{2-[(3-Cyclopropyloxy-4-difluoromethoxy)phenyl]-2-{5-[2-(1-hydroxy-1-trifluoromethyl-2,2,2-trifluoro)ethyl]thiazolyl}ethyl}pyridine N-oxide To a solution of pyridine (1.6 mL, 19.8 mmol) in toluene (5 mL) at 0° C. was slowly added thionyl bromide (0.84 mL, 10.8 mmol) and the resulting mixture was stirred for 5 min. To this mixture was slowly added a solution of the alcohol from the present Step 1 (4.38 g, 7.2 mmol) in toluene (10 mL). The mixture was warmed to room temperature and stirred for 45 min. The mixture was added directly to a silica gel column and eluted with hexamethyl acetate (95:5 to 7:3) to provide the crude bromide as a yellow oil (2.59 g) that was used immediately.

To a suspension of ethyl 3-pyridylacetate N-oxide (2 g, 11.0 mmol) in THF (60 mL) and HMPA (2 mL, 11.5 mmol) at 0° C. was added potassium bis(trimethylsilyl)amide (22 mL of a 0.5M solution in toluene, 11.0 mmol). The resulting mixture was warmed to room temperature and stirred for 1.5 h. The mixture was re-cooled to 0° C. and then a THF (10 mL) solution of the crude bromide prepared above (2.37 g, 3.5 mmol) was added. After stirring for 17 h at 25° C., the mixture was poured into sat. aq. NH$_4$Cl, the layers were separated and the aqueous phase was extracted with ethyl acetate. The combined organics were washed with brine, dried (Na$_2$SO$_4$) and concentrated. Flash chromatography of the residue (silica gel; dichloromethane/EtOH 98:2 to 95:5) provided the esters as a white foam (2.35 g).

This material (2.35 g, 3.5 mmol) was dissolved in a mixture of THF/MeOH/water (3:1:1, 33 mL). Next, 1.7N LiOH (6.5 mL, 11.1 mmol) was added and the resulting mixture was heated at 60° C. for 2.5 h. The mixture was cooled to room temperature and then 2N HCl (6.5 mL) was slowly added. The mixture was concentrated and partitioned between ethyl acetate and water. The aqueous phase was extracted with ethyl acetate and the combined organics were washed with brine, dried (Na$_2$SO$_4$) and concentrated to give a yellow solid (2.4 g). This material was dissolved in DMSO (30 mL) and heated at 130° C. for 2 h. Water (300 mL) was added and the mixture was extracted with dichloromethane (3×). The combined organics were washed with brine, dried (Na$_2$SO$_4$) and concentrated. Flash chromatography of the residue (silica gel; dichloromethane/MeOH/10% aq. NH$_4$OH 90:2.5:2.5 to 90:5:5) provided the title product as a white foam (1.66 g).

$^1$HNMR (50 MHz, acetone-d$_6$): δ0.60–0.88 (m, 4H), 3.48 (m, 1H), 3.58 (m, 1H), 3.90 (m, 1H), 4.90 (t, 1H), 6.79 (t, 1H), 7.01 (m, 1H), 7.12 (m, 2H), 7.22 (m, 1H), 7.49 (s, 1H), 7.86 (s, 1H), 7.95 (d, 1H), 8.09 (s, 1H), 8.33 (br s, 1H).

Examples 35 and 36

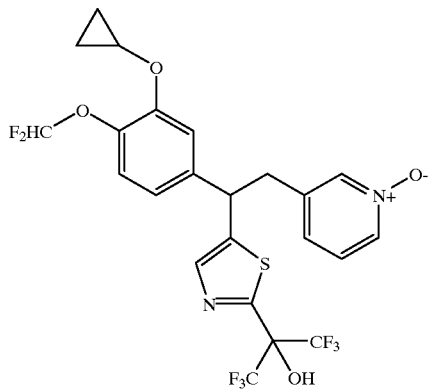

Chiral 3-{2-[(3-cyclopropyloxy-4-difluoromethoxy)phenyl]-2-{5-[2-(1-hydroxy-1-trifluoromethyl-2,2,2-trifluoro)ethyl]thiazolyl}ethyl}pyridine N-oxide Examples 35 and 36 were prepared by the following procedure. A solution of the material from Example 34 (1.66 g) in EtOH/hexane (20 mL, 3:7) was injected (4×5 mL) onto a Chiralpak® AD preparative (5 cm×50 cm) HPLC column (eluting with hexane/EtOH 9:1 at 80 ml/min with UV detection at 270 nm). The enantiomers were separated with the faster eluting enantiomer having a retention time of ~16 min (Enantiomer 1, Example 35) and the slower eluting enantiomer (Enantiomer 2, Example 36) having a retention time of ~19 min. The eluants were concentrated to provide the enantiomers as white foams: Enantiomer 1 (652 mg) and Enantiomer 2 (134 mg).

$^1$HNMR (500 MHz, acetone-d$_6$) for each: δ0.60–0.88 (m, 4H), 3.48 (m, 1H), 3.58 (m, 1H), 3.90 (m, 1H), 4.90 (t, 1H), 6.79 (t, 1H), 7.01 (m, 1H), 7.12 (m, 2H), 7.22 (m, 1H), 7.49 (s, 1H), 7.86 (s, 1H), 7.95 (d, 1H), 8.09 (s, 1H), 8.33 (br s, 1H).

Other variations or modifications, which will be obvious to those skilled in the art, are within the scope and teachings of this invention. This invention is not to be limited except as set forth in the following claims.

What is claimed is:

1. A compound represented by Formula (I):

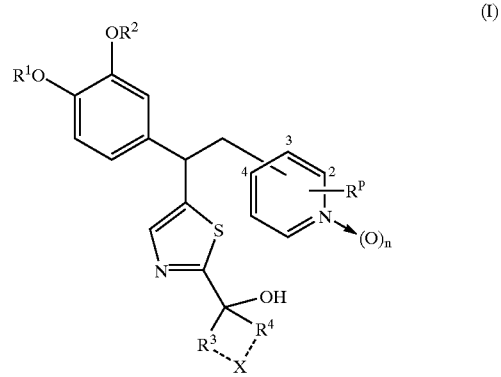

or a pharmaceutically acceptable salt thereof, wherein
   $R^1$ is $C_{1-6}$alkyl or $C_{3-6}$cycloalkyl, optionally substituted with 1–4 independent halogen;
   $R^2$ is $C_{1-6}$alkyl or $C_{3-6}$cycloalkyl, optionally substituted with 1–4 independent halogen;
   $R^3$ is $C_{1-4}$alkyl, $C_{3-6}$cycloalkyl, heteroaryl, or phenyl, any of which optionally substituted independently with 1–4 independent halogen or $C_{1-6}$alkyl;
   $R^4$ is H or $C_{1-4}$alkyl, said alkyl optionally substituted with 1–4 independent halogen;
   $R^P$ is H, halogen, nitrile, or a $C_{1-6}$alkyl group, said alkyl optionally substituted with 1–4 independent halogen;
   n is 0 or 1; and
   when $R^3$ and $R^4$ are connected to each other through X, then $R^3$ and $R^4$ are each $C_1$alkyl, and X is $C_{0-4}$alkyl.

2. The compound according to claim 1, or a pharmaceutically acceptable salt thereof, wherein
   $R^1$ is $C_{1-6}$alkyl, optionally substituted with 1–4 independent halogen;
   $R^2$ is $C_{1-6}$alkyl or $C_{3-6}$cycloalkyl, optionally substituted with 1–4 independent halogen;
   $R^3$ is $C_{1-4}$alkyl, $C_{3-6}$cycloalkyl, heteroaryl, or phenyl, any of which optionally substituted independently with 1–4 independent halogen or Cl-6alkyl;
   $R^4$ is H or $C_{1-4}$alkyl, said alkyl optionally substituted with 1–4 independent halogen;
   $R^P$ is H, halogen, nitrile, or a $C_{1-6}$alkyl group, said alkyl optionally substituted with 1–4 independent halogen;
   n is 0 or 1; and
   when $R^3$ and $R^4$ are connected to each other through X, then $R^3$ and $R^4$ are each $C_1$alkyl, and X is $C_{0-4}$alkyl.

3. The compound according to claim 1, or a pharmaceutically acceptable salt thereof, wherein R$^1$ is C$_{1-6}$alkyl, optionally substituted with 1–4 independent halogen;

R$^2$ is C$_{1-6}$alkyl, optionally substituted with 1–4 independent halogen;

R$^3$ is C$_{1-4}$alkyl, C$_{3-6}$cycloalkyl, heteroaryl, or phenyl, any of which optionally substituted independently with 1–4 independent halogen or C$_{1-6}$alkyl;

R$^4$ is H or C$_{1-4}$alkyl, said alkyl optionally substituted with 1–4 independent halogen;

R$^P$ is H, halogen, nitrile, or a C$_{1-6}$alkyl group, said alkyl optionally substituted with 1–4 independent halogen;

n is 0 or 1; and when R$^3$ and R$^4$ are connected to each other through X, then R$^3$ and R$^4$ are each C$_1$alkyl, and X is C$_{0-4}$alkyl.

4. The compound according to claim 1, or a pharmaceutically acceptable salt thereof, wherein R$^1$ is C$_{1-6}$alkyl, optionally substituted with 1–4 independent halogen;

R$^2$ is C$_{1-6}$alkyl, optionally substituted with 1–4 independent halogen;

R$^3$ is C$_{1-4}$alkyl, optionally substituted independently with 1–4 independent halogen or C$_{1-6}$alkyl;

R$^4$ is H or C$_{1-4}$alkyl, said alkyl optionally substituted with 1–4 independent halogen;

R$^P$ is H, halogen, nitrile, or a C$_{1-6}$alkyl group, said alkyl optionally substituted with 1–4 independent halogen; and n is 0 or 1.

5. The compound according to claim 1, or a pharmaceutically acceptable salt thereof, wherein R$^1$ is C$_{1-6}$alkyl, optionally substituted with 1–4 independent halogen;

R$^2$ is C$_{1-6}$alkyl, optionally substituted with 1–4 independent halogen;

R$^3$ is C$_{3-6}$cycloalkyl, optionally substituted independently with 1–4 independent halogen or C$_{1-6}$alkyl;

R$^4$ is H or C$_{1-4}$alkyl, said alkyl optionally substituted with 1–4 independent halogen;

R$^P$ is H, halogen, nitrile, or a C$_{1-6}$alkyl group, said alkyl optionally substituted with 1–4 independent halogen; and n is 0 or 1.

6. The compound according to claim 1, or a pharmaceutically acceptable salt thereof, wherein R$^1$ is C$_{1-6}$alkyl, optionally substituted with 1–4 independent halogen;

R$^2$ is C$_{1-6}$alkyl, optionally substituted with 1–4 independent halogen;

R$^3$ is heteroaryl, optionally substituted independently with 1–4 independent halogen or C$_{1-6}$alkyl;

R$^4$ is H or C$_{1-4}$alkyl, said alkyl optionally substituted with 1–4 independent halogen;

R$^P$ is H, halogen, nitrile, or a C$_{1-6}$alkyl group, said alkyl optionally substituted with 1–4 independent halogen; and n is 0 or 1.

7. The compound according to claim 1, or a pharmaceutically acceptable salt thereof, wherein R$^1$ is C$_{1-6}$alkyl, optionally substituted with 1–4 independent halogen;

R$^2$ is C$_{1-6}$alkyl, optionally substituted with 1–4 independent halogen;

R$^3$ is phenyl, optionally substituted independently with 1–4 independent halogen or C$_{1-6}$alkyl;

R$^4$ is H or C$_{1-4}$alkyl, said alkyl optionally substituted with 1–4 independent halogen;

R$^P$ is H, halogen, nitrile, or a C$_{1-6}$alkyl group, said alkyl optionally substituted with 1–4 independent halogen; and n is 0 or 1.

8. The compound according to claim 1, or a pharmaceutically acceptable salt thereof, wherein R$^1$ is C$_{1-6}$alkyl, optionally substituted with 1–4 independent halogen;

R$^2$ is C$_{1-6}$alkyl, optionally substituted with 1–4 independent halogen;

R$^3$ and R$^4$ are connected to each other through X;

R$^3$ and R$^4$ are each C$_1$alkyl;

X is C$_{0-4}$alkyl;

R$^P$ is H, halogen, nitrile, or a C$_{1-6}$alkyl group, said alkyl optionally substituted with 1–4 independent halogen; and n is 0 or 1.

9. The compound according to claim 1, or a pharmaceutically acceptable salt thereof, wherein R$^1$ is C$_{1-6}$alkyl, optionally substituted with 1–4 independent halogen;

R$^2$ is C$_{3-6}$cycloalkyl, optionally substituted with 1–4 independent halogen;

R$^3$ is C$_{1-4}$alkyl, C$_{3-6}$cycloalkyl, heteroaryl, or phenyl, any of which optionally substituted independently with 1–4 independent halogen or C$_{1-6}$alkyl;

R$^4$ is H or C$_{1-4}$alkyl, said alkyl optionally substituted with 1–4 independent halogen;

R$^P$ is H, halogen, nitrile, or a C$_{1-6}$alkyl group, said alkyl optionally substituted with 1–4 independent halogen;

n is 0 or 1; and when R$^3$ and R$^4$ are connected to each other through X, then R$^3$ and R$^4$ are each C$_1$alkyl, and X is C$_{0-4}$alkyl.

10. The compound according to claim 1, or a pharmaceutically acceptable salt thereof, wherein R$^1$ is C$_{1-6}$alkyl, optionally substituted with 1–4 independent halogen;

R$^2$ is C$_{3-6}$cycloalkyl, optionally substituted with 1–4 independent halogen;

R$^3$ is C$_{1-4}$alkyl, optionally substituted independently with 1–4 independent halogen or C$_{1-6}$alkyl;

R$^4$ is H or C$_{1-4}$alkyl, said alkyl optionally substituted with 1–4 independent halogen;

R$^P$ is H, halogen, nitrile, or a C$_{1-6}$alkyl group, said alkyl optionally substituted with 1–4 independent halogen; and n is 0 or 1.

11. The compound according to claim 1, or a pharmaceutically acceptable salt thereof, wherein R$^1$ is C$_{1-6}$alkyl, optionally substituted with 1–4 independent halogen;

R$^2$ is C$_{3-6}$cycloalkyl, optionally substituted with 1–4 independent halogen;

R$^3$ is C$_{3-6}$cycloalkyl, optionally substituted independently with 1–4 independent halogen or C$_{1-6}$alkyl;

R$^4$ is H or C$_{1-4}$alkyl, said alkyl optionally substituted with 1–4 independent halogen;

R$^P$ is H, halogen, nitrile, or a C$_{1-6}$alkyl group, said alkyl optionally substituted with 1–4 independent halogen; and n is 0 or 1.

12. The compound according to claim 1, or a pharmaceutically acceptable salt thereof, wherein R$^1$ is C$_{1-6}$alkyl, optionally substituted with 1–4 independent halogen;

R² is C₃₋₆cycloalkyl, optionally substituted with 1–4 independent halogen;

R³ is heteroalkyl, optionally substituted independently with 1–4 independent halogen or C₁₋₆alkyl;

R⁴ is H or C₁₋₄alkyl, said alkyl optionally substituted with 1–4 independent halogen;

Rᴾ is H, halogen, nitrile, or a C₁₋₆alkyl group, said alkyl optionally substituted with 1–4 independent halogen; and n is 0 or 1.

13. The compound according to claim 1, or a pharmaceutically acceptable salt thereof, wherein R¹ is C₁₋₆alkyl, optionally substituted with 1–4 independent halogen;

R² is C₃₋₆cycloalkyl, optionally substituted with 1–4 independent halogen;

R³ is phenyl, optionally substituted independently with 1–4 independent halogen or C₁₋₆alkyl;

R⁴ is H or C₁₋₄alkyl, said alkyl optionally substituted with 1–4 independent halogen;

Rᴾ is H, halogen, nitrile, or a C₁₋₆alkyl group, said alkyl optionally substituted with 1–4 independent halogen; and n is 0 or 1.

14. The compound according to claim 1, or a pharmaceutically acceptable salt thereof, wherein R¹ is C₁₋₆alkyl, optionally substituted with 1–4 independent halogen;

R² is C₃₋₆cycloalkyl, optionally substituted with 1–4 independent halogen;

R³ and R⁴ are connected to each other through X;

R³ and R⁴ are each C₁alkyl;

X is C₀₋₄alkyl;

Rᴾ is H, halogen, nitrile, or a C₁₋₆alkyl group, said alkyl optionally substituted with 1–4 independent halogen; and n is 0 or 1.

15. The compound according to claim 1, comprising

-continued

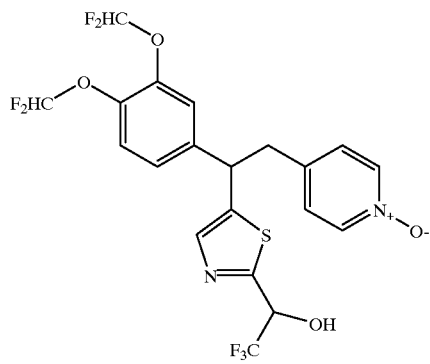

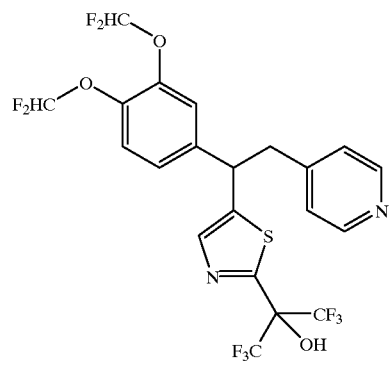

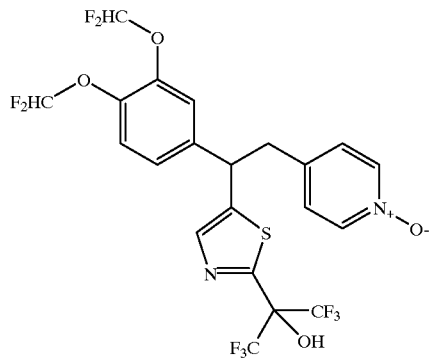

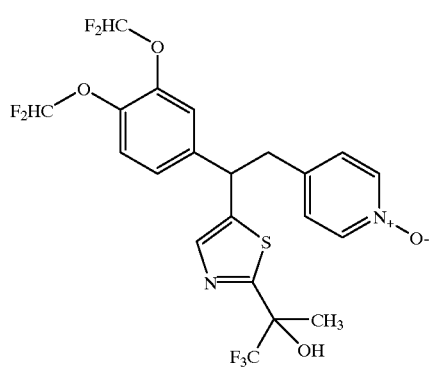

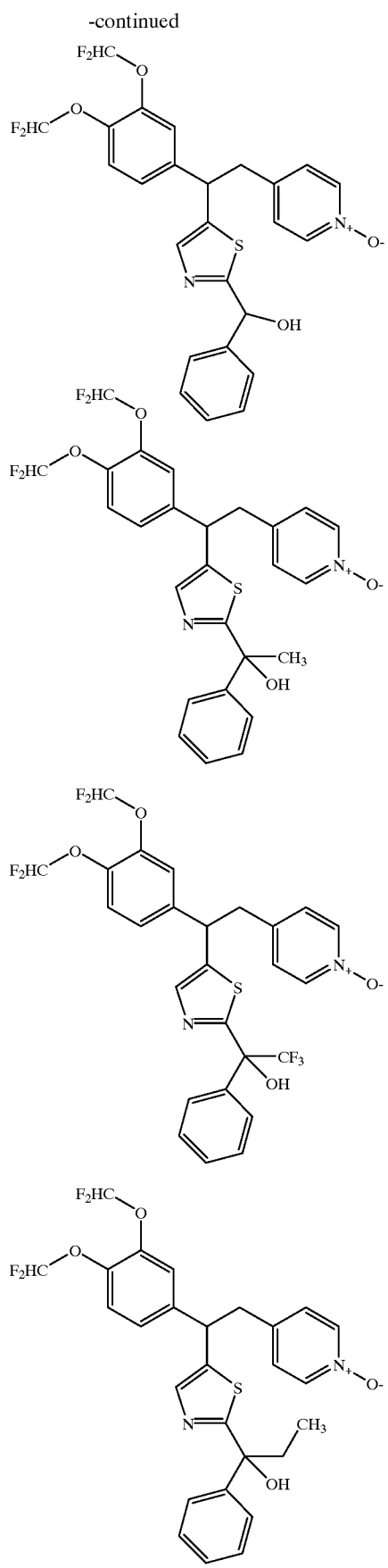
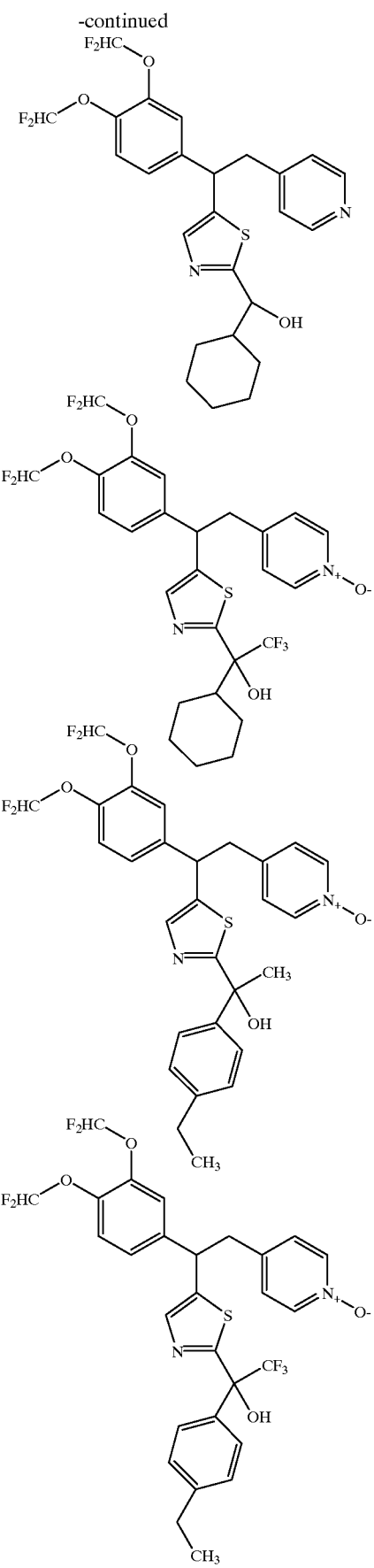

-continued
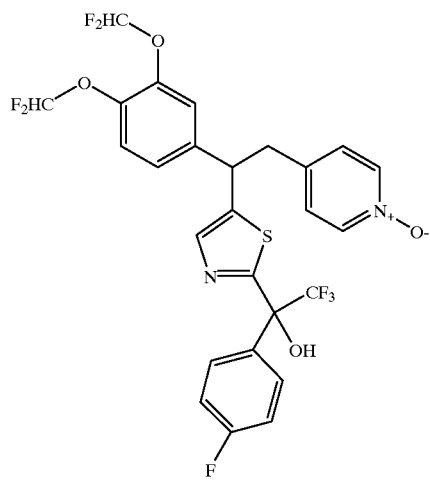
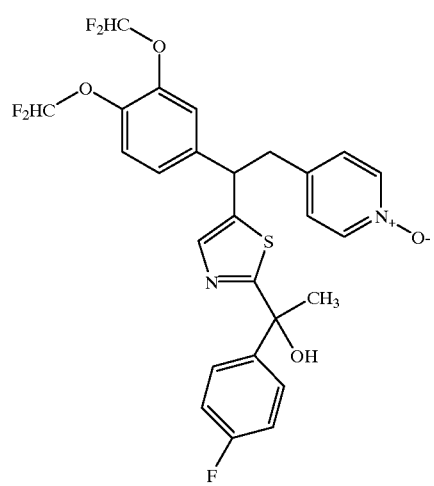
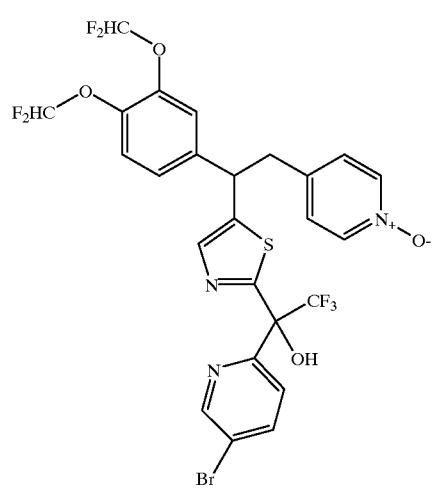
-continued
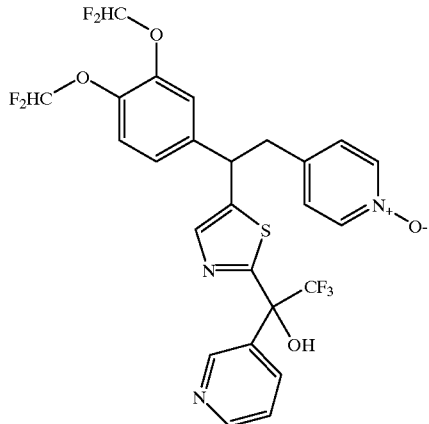
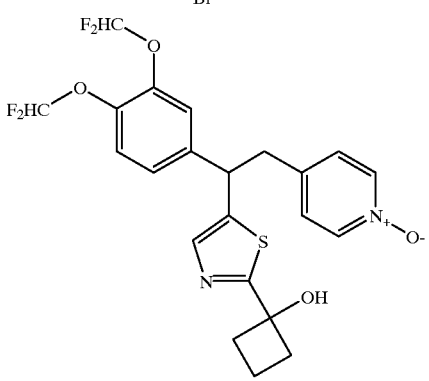
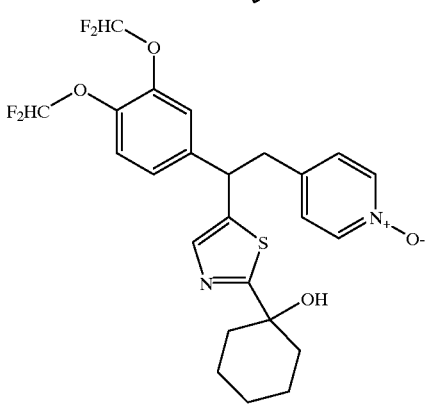
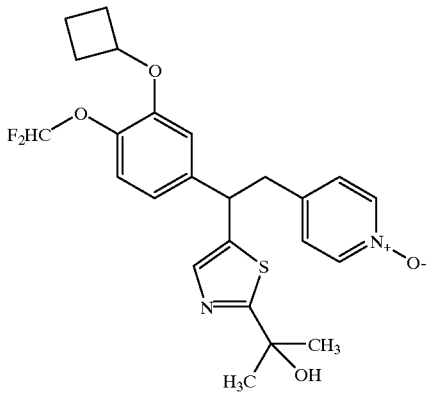

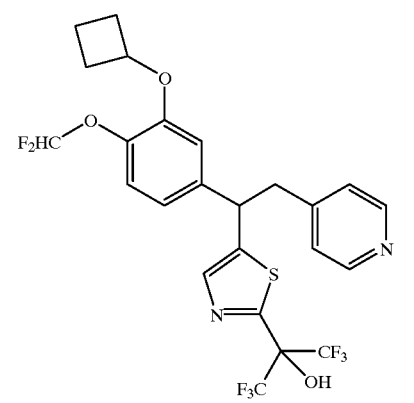
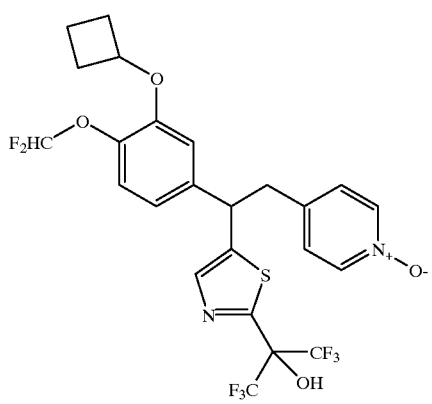
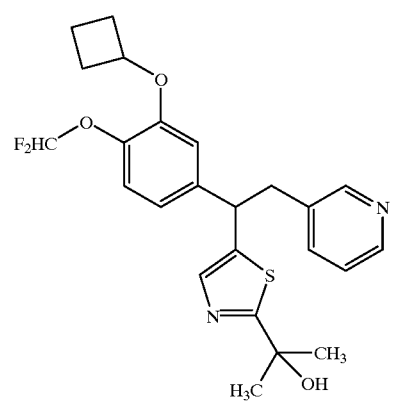
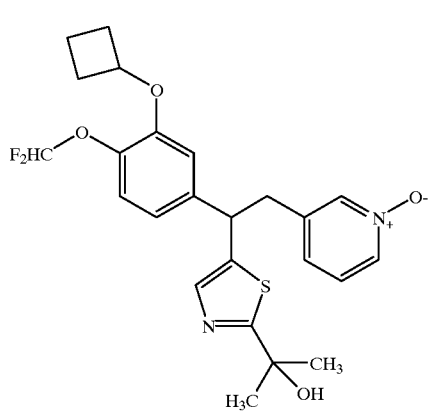
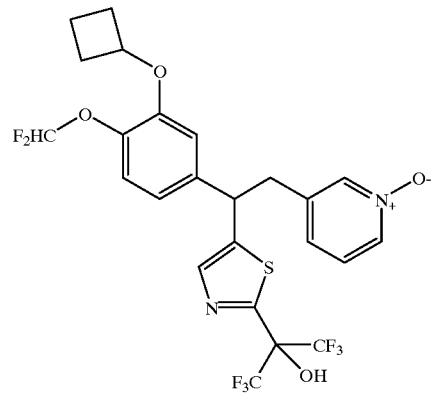
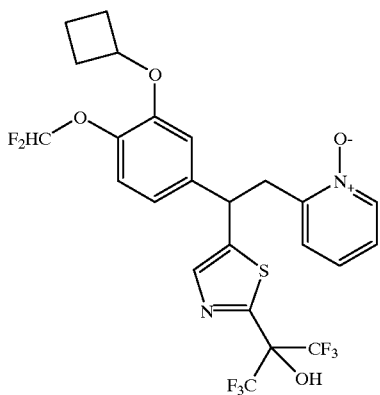
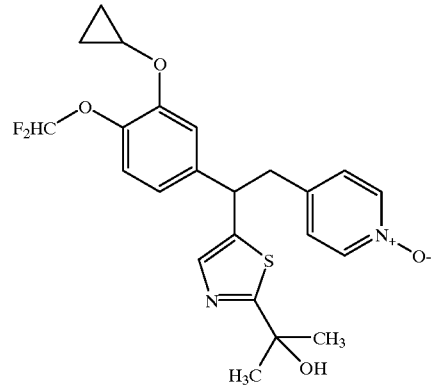
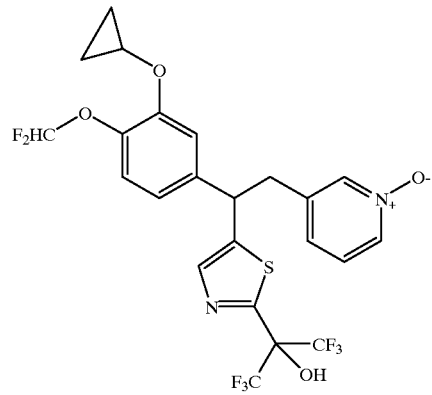
or a pharmaceutically acceptable salt thereof.

16. The compound according to claim 1, comprising (±)-4-{2-[3,4-Bis(difluoromethoxy)phenyl]-2-[5-(2-(1-hydroxy-1-methyl)ethyl)thiazolyl]ethyl}pyridine N-oxide;

Chiral 4-{2-[3,4-Bis(difluoromethoxy)phenyl]-2-[5-(2-(1-hydroxy-1-methyl)ethyl)thiazolyl]ethyl}pyridine N-oxide;

(±/±)-4-{2-[3,4-Bis(difluoromethoxy)phenyl]-2-[5-(2-(1-hydroxy-2,2,2-trifluoro)ethyl)thiazolyl]ethyl}pyridine;

(±/±)-4-{2-[3,4-Bis(difluoromethoxy)phenyl]-2-[5-(2-(1-hydroxy-2,2,2-trifluoro)ethyl)thiazolyl]ethyl}pyridine N-oxide;

(±)-4-{2-[3,4-Bis(difluoromethoxy)phenyl]-2-{5-[2-(1-hydroxy-1-trifluoromethyl-2,2,2-trifluoro)ethyl]thiazolyl}ethyl}pyridine;

(±)-4-{2-[3,4-Bis(difluoromethoxy)phenyl]-2-{5-[2-(1-hydroxy-1-trifluoromethyl-2,2,2-trifluoro)ethyl]thiazolyl}ethyl}pyridine N-oxide;

(±/±)-4-{2-[3,4-Bis(difluoromethoxy)phenyl]-2-{5-[2-(1-hydroxy-1-trifluoromethyl)ethyl]thiazolyl}ethyl}pyridine N-oxide;

(±/±)-4-{2-[3,4-Bis(difluoromethoxy)phenyl]-2-[5-(2-phenylmethanol)thiazolyl]ethyl}pyridine N-oxide;

(±/±)-4-{2-[3,4-Bis(difluoromethoxy)phenyl]-2-[5-(2-(1-hydroxy-1-phenyl)ethyl)thiazolyl]ethyl}pyridine N-oxide;

(±/±)-4-{2-[3,4-Bis(difluoromethoxy)phenyl]-2-[5-(2-(1-hydroxy-1-phenyl-2,2,2-trifluoro)ethyl)thiazolyl]ethyl}pyridine N-oxide;

(±/±)-4-{2-[3,4-Bis(difluoromethoxy)phenyl]-2-[5-(2-(1-hydroxy-1-phenyl)propyl)thiazolyl]ethyl}pyridine N-oxide;

(±/±)-4-{2-[3,4-Bis(difluoromethoxy)phenyl]-2-[5-(2-cyclohexylmethanol)thiazolyl]ethyl}pyridine;

(±/±)-4-{2-[3,4-Bis(difluoromethoxy)phenyl]-2-[5-(2-(1-hydroxy-1-cyclohexyl-2,2,2-trifluoromethyl)ethyl)thiazolyl]ethyl}pyridine N-oxide;

(±/±)-4-{2-[3,4-Bis(difluoromethoxy)phenyl]-2-[5-(2-(1-hydroxy-1-(4-ethyl)phenyl)ethyl)thiazolyl]ethyl}pyridine N-oxide;

(±/±)-4-{2-[3,4-Bis(difluoromethoxy)phenyl]-2-[5-(2-(1-hydroxy-1-(4-ethyl)phenyl-2,2,2-trifluoro)ethyl)thiazolyl]ethyl}pyridine N-oxide;

(±/±)-4-{2-[3,4-Bis(difluoromethoxy)phenyl]-2-[5-(2-(1-hydroxy-1-(4-fluoro)phenyl)ethyl)thiazolyl]ethyl}pyridine N-oxide;

(±/±)-4-{2-[3,4-Bis(difluoromethoxy)phenyl]-2-[5-(2-(1-hydroxy-1-(4-fluoro)phenyl-2,2,2-trifluoro)ethyl)thiazolyl]ethyl}pyridine N-oxide;

(±/±)-4-{2-[3,4-Bis(difluoromethoxy)phenyl]-2-[5-(2-(1-hydroxy-1-(5-bromopyridin-2-yl)-2,2,2-trifluoro)ethyl)thiazolyl]ethyl}pyridine N-oxide;

(±/±)-4-{2-[3,4-Bis(difluoromethoxy)phenyl]-2-[5-(2-(1-hydroxy-1-(6-bromopyridin-3-yl)-2,2,2-trifluoro)ethyl)thiazolyl]ethyl}pyridine N-oxide;

(±)-4-{2-[3,4-Bis(difluoromethoxy)phenyl]-2-{5-[2-(1-hydroxy)cyclobutyl]thiazolyl}ethyl}pyridine N-oxide;

(±)-4-{2-[3,4-Bis(difluoromethoxy)phenyl]-2-{5-[2-(1-hydroxy)cyclohexyl]thiazolyl}ethyl}pyridine N-oxide;

(±)-4-{2-[(3-cyclobutyloxy-4-difluoromethoxy)phenyl]-2-{5-[2-(1-hydroxy-1-methyl)ethyl]thiazolyl}ethyl}pyridine N-oxide;

chiral 4-{2-[(3-cyclobutyloxy-4-difluoromethoxy)phenyl]-2-{5-[2-(1-hydroxy-1-methyl)ethyl]thiazolyl}ethyl}pyridine N-oxide;

(±)-4-{2-[(3-cyclobutyloxy-4-difluoromethoxy)phenyl]-2-{5-[2-(1-hydroxy-1-trifluoromethyl-2,2,2-trifluoro)ethyl]thiazolyl}ethyl}pyridine;

(±)-4-{2-[(3-cyclobutyloxy-4-difluoromethoxy)phenyl]-2-{5-[2-(1-hydroxy-1-trifluoromethyl-2,2,2-trifluoro)ethyl]thiazolyl}ethyl}pyridine N-oxide;

Chiral 3-{2-[(3-cyclobutyloxy-4-difluoromethoxy)phenyl]-2-{5-[2-(1-hydroxy-1-methyl)ethyl]thiazolyl}ethyl}pyridine;

Chiral 3-{2-[(3-cyclobutyloxy-4-difluoromethoxy)phenyl]-2-{5-[2-(1-hydroxy-1-methyl)ethyl]thiazolyl}ethyl}pyridine;

Chiral 3-{2-[(3-cyclobutyloxy-4-difluoromethoxy)phenyl]-2-{5-[2-(1-hydroxy-1-methyl)ethyl]thiazolyl}ethyl}pyridine;

Chiral 3-{2-[(3-cyclobutyloxy-4-difluoromethoxy)phenyl]-2-{5-[2-(1-hydroxy-1-trifluoromethyl-2,2,2-trifluoro)ethyl]thiazolyl}ethyl}pyridine N-oxide;

(±)-2-{2-[(3-cyclobutyloxy-4-difluoromethoxy)phenyl]-2-{5-[2-(1-hydroxy-1-trifluoromethyl-2,2,2-trifluoro)ethyl]thiazolyl}ethyl}pyridine N-oxide;

(±)-4-{2-[(3-cyclopropyloxy-4-difluoromethoxy)phenyl]-2-{5-[2-(1-hydroxy-1-methyl)ethyl]thiazolyl}ethyl}pyridine N-oxide;

(±)-3-{2-[(3-cyclopropyloxy-4-difluoromethoxy)phenyl]-2-{5-[2-(1-hydroxy-1-trifluoromethyl-2,2,2-trifluoro)ethyl]thiazolyl}ethyl}pyridine N-oxide;

chiral 3-{2-[(3-cyclopropyloxy-4-difluoromethoxy)phenyl]-2-{5-[2-(1-hydroxy-1-trifluoromethyl-2,2,2-trifluoro)ethyl]thiazolyl}ethyl}pyridine N-oxide;

or a pharmaceutically acceptable salt thereof.

17. A pharmaceutical composition comprising a therapeutically effective amount of the compound according to claim 1 or a pharmaceutically acceptable salt thereof; and a pharmaceutically acceptable carrier.

* * * * *